(12) United States Patent
Newman et al.

(10) Patent No.: US 10,131,585 B2
(45) Date of Patent: Nov. 20, 2018

(54) HOPANOIDS PRODUCING BACTERIA AND RELATED BIOFERTILIZERS, COMPOSITIONS, METHODS AND SYSTEMS

(71) Applicant: CALIFORNIA INSTITUTE OF TECHNOLOGY, Pasadena, CA (US)

(72) Inventors: Dianne K. Newman, Pasadena, CA (US); Gargi Kulkarni, Pasadena, CA (US); Brittany Jo Belin, Pasadena, CA (US); Eric Geraud, Marseilles (FR); Antonio Molinaro, Napoli (IT); Alba Silipo, Napoli (IT)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

(21) Appl. No.: 15/298,172

(22) Filed: Oct. 19, 2016

(65) Prior Publication Data

US 2017/0107160 A1   Apr. 20, 2017

Related U.S. Application Data

(60) Provisional application No. 62/243,418, filed on Oct. 19, 2015.

(51) Int. Cl.
| | | |
|---|---|---|
| *A01N 43/40* | (2006.01) | |
| *C12N 1/00* | (2006.01) | |
| *C12N 15/52* | (2006.01) | |
| *C12N 15/82* | (2006.01) | |
| *C05F 11/08* | (2006.01) | |
| *C12N 1/20* | (2006.01) | |
| *C12N 1/14* | (2006.01) | |
| *A01N 63/00* | (2006.01) | |

(52) U.S. Cl.
CPC ............... *C05F 11/08* (2013.01); *C12N 1/20* (2013.01); *A01N 63/00* (2013.01); *C12N 1/14* (2013.01); *C12N 15/52* (2013.01); *C12N 15/82* (2013.01); *C12Y 402/01084* (2013.01)

(58) Field of Classification Search
CPC . C12N 1/20; C05F 11/00; C05F 11/08; G01N 33/92
USPC ............ 435/252.2, 320.1, 157, 243; 504/101
See application file for complete search history.

(56) References Cited

U.S. PATENT DOCUMENTS 9,187,381 B1 * 11/2015 Lanz ...................... A01N 63/02

OTHER PUBLICATIONS

Devos et al., (Proteins: Structure, Function and Genetics, 2000, vol. 41: 98-107).*
Whisstock et al., (Quarterly Reviews of Biophysics 2003, vol. 36 (3): 307-340.*
Witkowski et al., (Biochemistry 38:11643-11650, 1999.*
Kisselev L., (Structure, 2002, vol. 10: 8-9.*
Komanieck et al. JBC 2014, 289, pp. 35644-35655.*
Poonia et al. Intl. j. of Eng and Man res 2011 pp. 36-38.*
Battacharjee et al. ( App Microbiol Biotech 2008, pp. 199-209.*
Bravo et al. : Eur J. Biochem 2001,268, 1323-1331.*
Casadaban, M.J. et al., "Analysis of Gene-Control Signals by DNA-Fusion and Cloning in *Escherichia-coli*", Journal of Molecular Biology, 138(2), pp. 179-207, (1980).
Ehrhardt, D.W. et al., "Depolarization of Alfalfa Root Hair Membrane Potential by *Rhizobium meliloti* Nod Factors", 256(5059), pp. 998-1000, (1992).
Kannenberg, E.L. et al., "The Occurrence of Hopanoid Lipids in *Bradyrhizobium* Bacteria", FEMS Microbiology Letters, 127(3), pp. 255-261, (1995).
Leontein, K. et al., "Assignment of Absolute-Configuration of Sugars by g.l.c of Their Acetylated Glycosides Formed from Chiral Alcohols", Carbohydrate Research, 62(2), pp. 359-362, (1978), 5 pages.
Markowitz, V.M. et al., "Comparative Genome Analysis in the Integrated Microbial Genomes (IMG) System", Methods Mol. Biol., 395, pp. 35-56, (2007), 23 pages.
Oldroyd, G.E. et al., "The Rules of Engagement in the Legume-Rhizobial Symbiosis", Annu Rev Genet, 45, pp. 119-144, (2011), 28 pages.
Pearson, W.R. "Searching Protein Sequence Libraries: Comparison of the Sensitivity and Selectivity of the Smith-Waterman and FASTA Algorithms", Genomics, 11(3), pp. 635-650. 16 pages, (1991).
Regensburger, B. et al., "RNA-Polymerase from *Rhizobium japonicum*", Archives of Microbiology, 135(2), pp. 103-109, (1983), 9 pages.
Schafer, A. et al., "Small Mobilizable Multi-Purpose Cloning Vectors Derived from the *Escherichia coli* Plasmids pK18 and pK19: Selection of Defined Deletions in the Chromosome of *Corynebacterium glutamicum*", Gene, 145(1), pp. 69-73, (1994).
Simon, R. et al., "A Broad Host Range Mobilization System for in vivo Genetic-Engineering: Transposon Mutagenesis in Gram-Negative Bacteria", Bio-Technology, 1(9), pp. 784-791, (1983), 10 pages.
Talbot, H.M. et al., "Structural Characterisation of Unsaturated Bacterial Hopanoids by Atmospheric Pressure Chemical Ionisation Liquid Chromatography/Ion Trap Mass Spectrometry", Rapid Communications in Mass Spectrometry, 21, pp. 1613-1622. 10 pages, (2007).
Talbot, H.M. et al., "Characteristic Fragmentation of Bacteriohopanepolyols During Atmospheric Pressure Chemical Ionisation Liquid Chromatography/Ion Trap Mass Spectrometry", Rapid Communications in Mass Spectrometry, 17, pp. 2788-2796. 9 pages, (2003).
Westphal, O. et al., "Bacterial Lipopolysaccharide-Extraction with Phenol-Water and Further Applications of the Procedure", Methods Carbohydr Chem, 43, pp. 83-91, (1965).

* cited by examiner

Primary Examiner — Robert B Mondesi
Assistant Examiner — Mohammad Y Meah
(74) *Attorney, Agent, or Firm* — Steinfl + Bruno LLP

(57) ABSTRACT

Hopanoids, hopanoids-producing nitrogen-fixing bacteria, and related formulations, systems and methods are described herein. In particular, hopanoids alone or in combination with hopanoid-producing nitrogen-fixing bacteria can be used as biofertilizer to stimulate plant growth and yield with enhanced tolerance to diverse stresses found in plant-microbe symbiotic microenvironments.

26 Claims, 14 Drawing Sheets

Specification includes a Sequence Listing.

HOPANOIDS PRODUCING BACTERIA AND RELATED BIOFERTILIZERS, COMPOSITIONS, METHODS AND SYSTEMS

CROSS REFERENCE TO RELATED APPLICATIONS

The present application claims priority to U.S. Provisional Application No. 62/243,418, entitled "Using Hopanoids to Improve Stress Resistance in Biological Nitrogen Fixation" filed on Oct. 19, 2015, which is incorporated herein by reference in its entirety.

STATEMENT OF GOVERNMENT GRANT

This invention was made with government support under Grant No. NNX12AD93G awarded by NASA, under Grant No. CHE1224158 awarded by the National Science Foundation, and under Grant No. 06434 awarded by the Howard Hughes Medical Institute (HHMI). The government has certain rights in the invention.

FIELD

The present disclosure relates to hopanoids, hopanoids producing bacteria and related biofertilizers, microorganisms, compositions, methods and systems comprising hopanoid-producing microorganisms and related formulations, and uses as biofertilizer in agriculture industry.

BACKGROUND

The exploitation of beneficial microbes as a biofertilizer has become of paramount importance in agriculture sector for their potential role in food safety and sustainable crop production.

There remains however a challenge for developing eco-friendly and economically feasible alternatives to chemical fertilizers, which can improve soil fertility, health of the environment, and agricultural productivity particularly under different soil conditions.

SUMMARY

Provided herein are hopanoid-producing bacteria, and related biofertilizers, microorganisms, formulations, and methods which can comprise one or more particular types of hopanoids and/or one or more hopanoid-producing nitrogen-fixing bacteria. In several embodiments, the microorganisms, and related biofertilizers, compositions methods and systems described herein can improve stress-resistance during the progression of plant-microbe symbiosis and in particular of a legume-microbe symbiosis.

According to a first aspect, a biofertilizer for a leguminous plant is described. The biofertilizer essentially consists of one or more nitrogen-fixing rhizobia capable of producing $C_{35}$ hopanoids. In the biofertilizer, the one or more nitrogen-fixing rhizobia capable of producing $C_{35}$ hopanoids are in a form suitable for administration to one or more leguminous plant or seed, and/or for administration to a soil surrounding the one or more leguminous plant or seed. In some embodiments, the biofertilizer is in combination with carrier allowing increased stability, viability and/or effectiveness of the nitrogen-fixing bacteria gas exchange of the one or more nitrogen-fixing rhizobia.

According to a second aspect, a method to provide a biofertilizer for a leguminous plant, is described. The method comprises providing one or more candidate nitrogen fixing rhizobia strains. The method further comprises detecting among the one or more candidate nitrogen fixing rhizobia strains, at least one rhizobia strain capable of producing $C_{35}$ hopanoids. The method further comprises providing the at least one rhizobia strain capable of producing $C_{35}$ hopanoids in a form suitable for administration to a leguminous plant or seed or soil surrounding a leguminous plant or seed, thus providing a biofertilizer for the leguminous plant. In some embodiments, the method further comprises providing the at least one rhizobia strain capable of producing $C_{35}$ hopanoids in combination with carrier allowing increased stability, viability and/or effectiveness of the nitrogen-fixing bacteria gas exchange of the one or more nitrogen-fixing rhizobia.

According to a third aspect, a method to provide a biofertilizer for a leguminous plant, is described. The method comprises genetically engineering a nitrogen fixing rhizobia strain incapable of producing $C_{35}$ hopanoids to introduce $C_{35}$ synthesis genes thus providing a genetically engineered nitrogen fixing rhizobia strains capable of producing $C_{35}$ hopanoids. The method further comprises providing the genetically engineered nitrogen fixing rhizobia strains in a form suitable for administration to a leguminous plant or seed, and/or a soil surrounding leguminous plant or seed thus providing the biofertilizer for the leguminous plant.

According to a fourth aspect, a biofertilizer composition for a leguminous plant is described. The biofertilizer composition comprises one or more biofertilizers essentially consisting of one or more nitrogen-fixing rhizobia capable of producing $C_{35}$ hopanoids and an acceptable vehicle. In some embodiments, the biofertilizer composition can further comprise one or more $C_{35}$ hopanoids. In the biofertilizer composition the one or more biofertilizers and the vehicle are formulated for administration to a leguminous plant and/or for administration to a leguminous seed. In some embodiments the vehicle comprises at least one carrier allowing increased stability, viability and/or effectiveness of the nitrogen-fixing bacteria gas exchange of the one or more nitrogen-fixing rhizobia.

According to a fifth aspect, a biofertilizer composition is described. The biofertilizer composition comprises one or more nitrogen-fixing rhizobia capable of producing $C_{35}$ hopanoids and one or more $C_{35}$ hopanoids. In some embodiments the composition can be formulated for administration to a leguminous plant, a leguminous seed and/or soil surrounding the leguminous plant or leguminous seed. In some embodiments, the biofertilizer composition further comprises one or more carriers allowing increased stability, viability and/or effectiveness of the nitrogen-fixing bacteria gas exchange of the one or more nitrogen-fixing rhizobia.

According to a sixth aspect, a genetically modified nitrogen-fixing *rhizobium* is described. The genetically modified nitrogen-fixing *rhizobium* is a *rhizobium* naturally incapable of producing $C_{35}$ hopanoids and genetically engineered to produce $C_{35}$ hopanoids.

According to a seventh aspect, described herein is a leguminous seed coated and/or inoculated with a biofertilizer, and/or biofertilizer composition herein described, optionally in combination with one or more $C_{35}$ hopanoids. In the leguminous coated and/or inoculated seed, the nitrogen-fixing rhizobia in the biofertilizer and/or biofertilizer composition can be rhizobia naturally capable of producing $C_{35}$ hopanoids and/or rhizobia naturally incapable of producing $C_{35}$ hopanoids and genetically modified to produce $C_{35}$ hopanoids.

According to an eighth aspect, a method of fertilizing leguminous plants is described. The method comprises applying one or more biofertilizer and/or biofertilizer compositions herein described to a leguminous plant or soil surrounding a leguminous plant for a time and under conditions to allow symbiosis of the nitrogen-fixing rhizobia with the leguminous plant. In some embodiments the biofertilizer and/or biofertilizer compositions can be applied in combination with one or more $C_{35}$ hopanoids. In those embodiments, applying the biofertilizer and/or biofertilizer compositions and applying one or more $C_{35}$ hopanoids are performed for a time and under conditions allowing interaction of the one or more $C_{35}$ hopanoids with the nitrogen-fixing rhizobia in the administered biofertilizer and/or biofertilizer compositions.

According to a ninth aspect, a method of fertilizing leguminous plants is described. The method comprises coating and/or inoculating one or more seeds of the leguminous plant with one or more biofertilizer and/or biofertilizer compositions herein described. In some embodiments the method further comprises coating and/or inoculating the one or more seeds of the leguminous plant with one or more $C_{35}$ hopanoids before the coating and/or inoculating the one or more seeds of the leguminous plant with one or more biofertilizer and/or biofertilizer composition.

According to a tenth aspect, a system to fertilize leguminous plants is described. The system comprises one or more biofertilizer and/or biofertilizer compositions herein described and one or more $C_{35}$ hopanoids for simultaneous sequential or combined use in fertilizing a leguminous plant herein described.

According to an eleventh aspect, a system to fertilize a leguminous plant is described. The system comprises one or more leguminous seed coated with one or more biofertilizer and/or biofertilizer composition herein described and one or more $C_{35}$ hopanoids for simultaneous sequential or combined use in fertilizing a leguminous plant herein described.

According to a twelfth aspect, a method of storing a biofertilizer is described herein. The method comprises providing a biofertilizer herein describe, the biofertilizer comprising nitrogen-fixing bacteria that are naturally producing $C_{35}$ hopanoids and/or have been genetically modified to produce $C_{35}$ hopanoids, and storing the biofertilizer formulation at a temperature between 22° C. and 37° C.

According to a thirteenth aspect, a biofertilizer for a soil is described. The biofertilizer essentially consist of one or more nitrogen-fixing rhizobia capable of producing $C_{35}$ hopanoids and capable to fixing nitrogen outside a plant in a form suitable for administration to the soil. Such biofertilizer can be applied to oxygen-poor soils to enrich the soil nitrogen content.

The biofertilizer, biofertilizer compositions, nitrogen-fixing rhizobia, seeds and related methods and systems herein described allow in several embodiments the nitrogen-fixing rhizobia with enhanced tolerance to numerous stresses, including acidic pH, high temperature, high osmolarity, oxidative stress, detergents and antibiotics.

The biofertilizer, biofertilizer compositions, nitrogen-fixing rhizobia, seeds and related methods and systems herein described allow in several embodiments improved viability of the rhizobia used in fertilization of leguminous plants, and/or improvement of the related survive under soil conditions, such as high temperature and low pH, to effectively enhance plant growth and soil life and to improve soil nitrogen content when leguminous plants are used for crop rotation.

The biofertilizer, biofertilizer compositions, nitrogen-fixing rhizobia, seeds and related methods and systems herein described can be used in connection with agronomy, ecology and other applications wherein increased stress-tolerance of rhizobia is desired. Additional exemplary applications would be identifiable by a skilled person upon reading of the present disclosure.

The details of one or more embodiments of the disclosure are set forth in the accompanying drawings and the description below. Other features, objects, and advantages will be apparent from the description and drawings, and from the claims.

BRIEF DESCRIPTION OF DRAWINGS

The accompanying drawings, which are incorporated into and constitute a part of this specification, illustrate one or more embodiments of the present disclosure and, together with the detailed description and the examples, serve to explain the principles and implementations of the disclosure.

DETAILED DESCRIPTION

Figure 1:
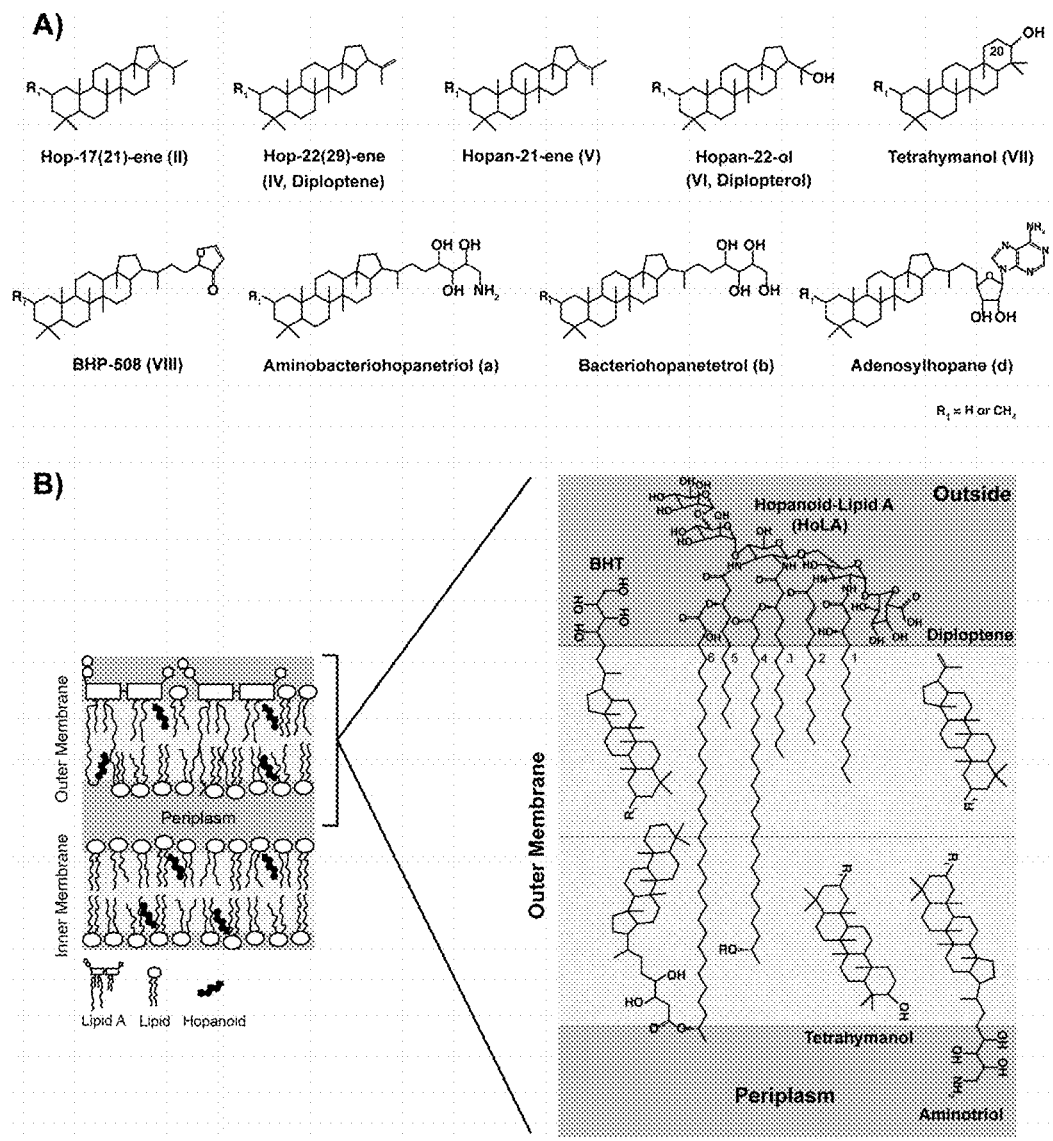
FIG. 1 shows, in panel A, exemplary chemical structures of hopanoids and related molecules and in panel B, the cell envelope of a Gram-negative bacterium consisting of an inner (IM) and an outer membrane (OM). Hopanoids are found within both membranes. They are either "free" or, in the case of $C_{35}$ hopanoids, covalently bound to lipid A (HoLA), which is present in the outer leaflet of the OM. As seen in the expanded view of the OM, *B. diazoefficiens* makes short ($C_{30}$) hopanoids like diploptene and extended ($C_{35}$) hopanoids like bacteriohopanetetrol (BHT) and aminotriol. Penta- and hexa-acylated Lipid A contain 5 and 6 fatty acyl chains, respectively. Hepta-acylated Lipid A contains the $C_{35}$ hopanoid, 34-carboxyl-bacteriohopane-32,33-diol, covalently attached to hexa-acylated Lipid A. *B. diazoefficiens* makes another triterpenoid with a gammacerane skeleton called tetrahymanol. With the exception of HoLA, hopanoid positioning in the inner vs outer leaflet has not been established and example structures are placed randomly. Dark gray and light gray colors represent hydrophilic and hydrophobic regions, respectively.

Provided herein are hopanoids, hopanoid-producing bacteria and related biofertilizers, compositions, methods and systems that in several embodiment stimulate plant growth with enhanced tolerance to stresses encountered during the progression of plant-microbe symbioses.

The term "hopanoids" as used herein indicate bacteriohopanepolyols (BHPs), which is a class of pentacyclic triterpenoids that are found in a variety of bacteria including Gram-positive and Gram-negative bacteria as cell membrane components.

Hopanoids in the sense of the disclosure include in particular amphiphilic BHP comprising a $C_{30}$ pentacyclic triterpene hydrocarbon skeleton, derived from squalene via the enzyme squalene-hopene cyclase, that can be linked via a C—C bond to a $C_5$ sugar moiety derived from ribose. In some hopanoids, the polar moieties of BHP can attach sugars, amino acids or other functionalized units, which can be used for their preservation in the geological record. The apolar ring system of hopanoids in the sense of the disclosure can comprise an extra methyl group at either position 2 (2Me-hopanoids) or position 3 (3Me-hopanoids) located in the A-ring, or by unsaturation and/or attachment to a ribose-derived side chain ($C_{35}$-hopanoids) (see Examples 3 and 4) [3]. Distribution of hopanoids with different chemical structure among bacteria does not appear to follow a systematic pattern. For example, BHPs methylated at C-2 are known to be produced in abundance by cyanobacteria, but not by other bacteria.

Hopanoids producing bacteria, in the sense of the disclosure are bacteria having a gene set allowing production of one or more hopanoids in the sense of the disclosure and in particular a set of genes encoding molecules that catalyze the production of hopanoids using squalene as the beginning molecular substrate, including but not limited to the following genes: hpnP, hpnF (also known as shc), hpnG, hpnH, and hpnO."

Hopanoid-producing bacteria comprise both free-living bacteria and symbiotic bacteria. Examples of free-living bacteria producing hopanoids include *Rhodopseudomonas palustris*, *Bacillus* spp., *Synechococcus* spp., and *Azotobacter* spp. Examples of symbiotic bacteria producing hopanoids include *Bradyrhizobia* spp., *Frankia* spp., *Anabaena* spp., and *Nostoc* spp. For example, hopanoids comprise BHPs localized in the cytoplasmic and outer membranes of various bacteria such as *Alicyclobacillus acidocaldarius*, *Zymomonas mobilis*, *Frankia* sp., and *Streptomyces coelicolor*. In particular, hopanoids have been found in nitrogen-fixing bacteria that form root or stem nodules in symbiosis with various types of plants, where the capacity for hopanoid biosynthesis is statistically enriched in the (meta)genomes of bacteria associated with plants [4]. For example, hopanoids have been found in membranes of plant symbionts of nitrogen-fixing *Bradyrhizobia* (40% of total lipid extract (TLE)) and *Frankia* (87%) genera [5, 6]. Studies have shown that elimination of hopanoid biosynthesis in photosynthetic *Bradyrhizobium* BTAi1 impairs its symbiosis with the legume *Aeschynomene evenia* [7]. Hopanoids have not been found in other plant-associated bacteria, including ~50% of the symbiotic Rhizobiales family. Exemplary hopanoids producing bacteria that are naturally capable of producing hopanoids include strains from *Acetobacter*, *Acidiphilium*, *Azotobacter vinelandii*, *Bacillus amyloliquefaciens*, *Bacillus anthracis*, *Bacillus cereus*, *Burkholderia cenocepacia*, *Bradyrhizobium*, *Burkholderia*, *Frankia*, *Geobacter*, *Methylobacterium*, *Pelobacter*, *Nitrosococcus*, *Rhodopseudomonas*, *Rhodospirillum*, *Synechocystis*, *Streptomyces*, *Zymomonas mobilis* and others identifiable by a person of ordinary skill in the art of microbiology.

In hopanoids producing bacteria in the sense of the disclosure, hopanoids can promote membrane rigidity [8] and confer protection against numerous stresses, including acidic or alkaline pH, high temperature, high osmolarity, oxidative stress, detergents and antibiotics [7, 9-11]. The structural variation of hopanoids, including modification by methylation or the addition of diverse polar head groups, suggests there may be specificity in their structures with regard to localization and/or function. Evidence also suggests that diverse hopanoid types have non-overlapping roles. For example, in *Rhodopseudomonas palustris* [12] and *Burkholderia cenocepacia* [10], $C_{35}$ hopanoids are critical for OM stability, and resistance to low pH, detergent (sodium dodecyl sulfate, SDS) and polymyxin B, respectively. In *R. palustris*, the biosynthesis of 2Me-hopanoids is transcriptionally induced under stress [9], suggesting that 2Me-hopanoids may contribute to stress resistance under certain conditions and organisms. In *Methylococcus capsulatus*, 3Me-hopanoids contribute to late stationary phase survival [13]. In vitro, 2Me-hopanoids rigidify membranes of varied compositions [8]. However, no study has explored whether different hopanoids impact fitness in a natural ecological context. It is unclear whether there are functional distinctions under specific environmental conditions for diverse hopanoid types.

In embodiments herein described, biofertilizer to be used to fertilize plants or soil are hopanoids producing bacteria capable of producing $C_{35}$ hopanoids. The term "$C_{35}$ hopanoids" in the sense of the disclosure include in particular amphiphilic BHP comprising a $C_{30}$ pentacyclic triterpene hydrocarbon skeleton, derived from squalene via the enzyme squalene-hopene cyclase, and are linked via a C—C bond to a $C_5$ sugar moiety derived from ribose In particular, in embodiments herein described, $C_{35}$ hopanoids are compounds of Formula (I):

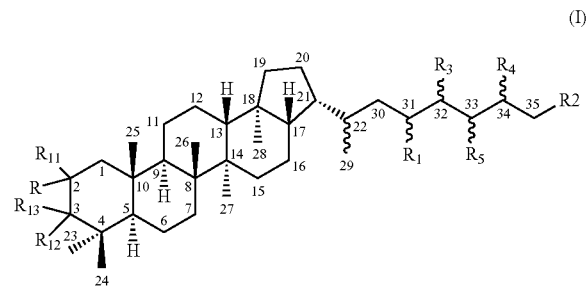

(I)

C22, C31, C33 and C34 have independently R or S chirality;

R, $R_{11}$, $R_{12}$ and $R_{13}$ are independently selected from H, D, methyl, or ethyl groups;

$R_1$, $R_3$, $R_4$, and $R_5$ are selected from H, D, methyl, hydroxymethyl, aminomethyl, hydroxyl, or amino groups, wherein at least three of the $R_1$, $R_3$, $R_4$, and $R_5$ groups each contains hydroxymethyl, aminomethyl, hydroxyl, or amino groups;

$R_2$ is selected from OH, $NH_2$, hydroxymethyl, aminomethyl, formula (II)

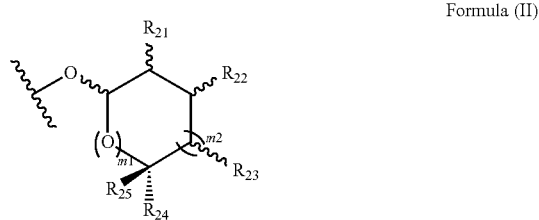

Formula (II)

wherein a wavy line on the ring carbon indicates a R or S chirality of the ring carbon, $m_1$ and $m_2$ are independently 0 or 1;

$R_{21}$, $R_{22}$, $R_{23}$, $R_{24}$ and $R_{25}$ are selected from OH, $NH_2$, hydroxymethyl, or aminomethyl groups wherein $R_{21}$, $R_{22}$, $R_{23}$, $R_{24}$ and $R_{25}$ contain at least one $NH_2$ or aminimethyl groups and one of $R_{24}$ and $R_{25}$ is hydroxymethyl, or aminomethyl groups.

In some embodiments, Formula (II) can be Formula (IIa) or Formula (IIb):

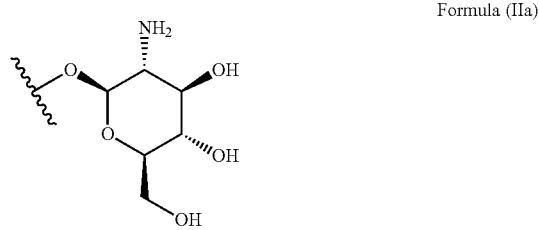

Formula (IIa)

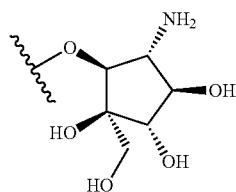

Formula (IIb)

In some embodiments, $R_3$, $R_4$ and $R_5$ are OH. In some embodiments, $R_2$ is $NH_2$. In some particular embodiments, the $C_{35}$ hopanoids are bacteriohopanetetrol (BHT) and aminobacteriohopanetrial shown in FIG. 1A.

In some embodiments, the $C_{35}$ hopanoids comprise aminobacteriohopanetriol, bacteriohopanetriol, 2-methyl bacteriohopanetriol, aminobacteriohopanetriol, bacteriohopanetetrol, 2Me-aminobacteriohopanetriol, adenosylhopane, 2Me-bacteriohopanetetrol.

$C_{35}$ hopanoids are produced in bacteria by a set of genes comprising at least shc, hpnH and hpnG. The set can also comprise hpnO, hpnP, and also hpnC, hpnD and hpnE, depending on the specific C35 produced as will be understood by a skilled person. For example, hnpH is required to generate adenosyl hopane, which is a C35 hopanoid, however, hpnG and hpnO are needed to make aminobacteriohopanetetrol and bacteriohopanetetrol (Welander 2012 [12]). shc, hpnH and hpnG, hpnO, hpnP, hpnC, hpnD and hpnE are conserved among various $C_{35}$ producing bacteria and encodes enzymes forming a hopanoid biosynethtic pathway such as squalene-hopene cyclase (sch), B12 binding radical SAM (hpnH), nucleosidase (hpnG), ornithine-oxo-acid-transaminase (hpnO), B12 binding radical SAM (hpnP), squalene synthase (hpnC), squalene synthase (hpnD), and squalene dependent FAD-dependent desaturase (hpnE) as will be understood by a skilled person. In particular among different C35 producing bacteria strains, each of the proteins encoded by shc, hpnH and hpnG, hpnO, hpnP, hpnC, hpnD or hpnE genes shows a same enzymatic activity in the different strains even if the sequences can differ from strain to strain at a polynucleotide and/or at a protein level. In particular, proteins encoded by each of shc, hpnH and hpnG, hpnO, hpnP, and also hpnC, hpnD and hpnE can have an amino acid sequence identity >55% at a protein level while maintaining the respective enzymatic activity indicated above (see e.g. hpnP as indicated by Ricci et al. [14])

The term "gene" as used herein indicates a polynucleotide encoding for a protein that in some instances can take the form of a unit of genomic DNA within a bacteria, plant or other organisms.

The term "polynucleotide" as used herein indicates an organic polymer composed of two or more monomers including nucleotides, nucleosides or analogs thereof. The term "nucleotide" refers to any of several compounds that consist of a ribose or deoxyribose sugar joined to a purine or pyrimidine base and to a phosphate group and that are the basic structural units of nucleic acids. The term "nucleoside" refers to a compound (as guanosine or adenosine) that consists of a purine or pyrimidine base combined with deoxyribose or ribose and is found especially in nucleic acids. The term "nucleotide analog" or "nucleoside analog" refers respectively to a nucleotide or nucleoside in which one or more individual atoms have been replaced with a different atom or a with a different functional group. Accordingly, the term polynucleotide includes nucleic acids of any length, and in particular DNA RNA analogs and fragments thereof.

The term "protein" as used herein indicates a polypeptide with a particular secondary and tertiary structure that can interact with another molecule and in particular, with other biomolecules including other proteins, DNA, RNA, lipids, metabolites, hormones, chemokines, and/or small molecules. The term "polypeptide" as used herein indicates an organic linear, circular, or branched polymer composed of two or more amino acid monomers and/or analogs thereof. The term "polypeptide" includes amino acid polymers of any length including full-length proteins and peptides, as well as analogs and fragments thereof. A polypeptide of three or more amino acids is also called a protein oligomer, peptide, or oligopeptide. In particular, the terms "peptide" and "oligopeptide" usually indicate a polypeptide with less than 100 amino acid monomers. A protein "sequence" indicates the order of the amino acids that form the primary structure As used herein the term "amino acid", "amino acid monomer", or "amino acid residue" refers to organic compounds composed of amine and carboxylic acid functional groups, along with a side-chain specific to each amino acid. In particular, alpha- or α-amino acid refers to organic compounds composed of amine (—NH2) and carboxylic acid (—COOH), and a side-chain specific to each amino acid connected to an alpha carbon. Different amino acids have different side chains and have distinctive characteristics, such as charge, polarity, aromaticity, reduction potential, hydrophobicity, and pKa. Amino acids can be covalently linked to form a polymer through peptide bonds by reactions between the amine group of a first amino acid and the carboxylic acid group of a second amino acid. Amino acid in the sense of the disclosure refers to any of the twenty naturally occurring amino acids, non-natural amino acids, and includes both D an L optical isomers.

The term "percent identity refers to a quantitative measurement of the similarity between sequences of a polypeptide or a polynucleotide and in particular indicates the amount of characters which match exactly between two different sequences. Widely used similarity searching programs, like BLAST, PSI-BLAST [15], SSEARCH [16] [17], FASTA [18] and the HMMER3 [19] programs produce accurate statistical estimates, ensuring protein sequences that share significant similarity also have similar structures.

In embodiments herein described, hopanoids producing bacteria capable of producing $C_{35}$ hopanoids, and particularly $C_{35}$ hopanoids of Formula (I), are nitrogen-fixing bacteria and, in particular, symbiotic nitrogen fixing bacteria, which can be used to fertilize a plant and/or a soil, as will be understood by a skilled person upon reading of the present disclosure.

The term "nitrogen-fixing bacteria" refers to microorganisms capable of transforming atmospheric nitrogen to fixed nitrogen in inorganic compounds usable by plants. Nitrogen-fixing bacteria are also called diazotrophs; some diazotrophs are capable of performing nitrogen fixation naturally in a free-living state, while others can only fix nitrogen within plant hosts. Examples of diazotrophs include non-symbiotic bacteria, such as the plant-associated soil bacterium *Azotobacter*, as well as symbiotic bacteria including rhizobia (in particular *Bradyrhizobia* spp., *Rhizobiacaea, Phyllobacteria, Sinorhizobia (Ensifer), Mesorhizobia* and *Azorhizobia*), cyanobacteria (*Anabaena* spp., *Nostoc* spp.), *Frankia* spp., and others identifiable by a person of ordinary skill in the art.

The wording "symbiotic bacteria" as used herein indicates bacteria that provide fixed nitrogen to plants via direct plant-microbe association in exchange for nutrients (generally carbon sources) and include the model bacteria *Sinorhizobium meliloti, Rhizobium leguminosarum*, and *Bradyrhizobium diazoefficiens*. During symbiotic nitrogen fixation, nitrogen-fixing bacteria establish a symbiotic relationship with plants in which the plant provides the nitrogen-fixing bacteria with carbohydrates as an energy source and the nitrogen-fixing bacteria provides the plant with nitrogen in the form of ammonium. Examples of plant-microbe symbioses include rhizobia associated with leguminous plants and trees of the *Acacia* and *Parasponia* families, *Frankia* associated with certain dicotyledonous species (actinorhizal plants), certain *Azospirillum* species, associated with cereal grasses, *Nostoc* or *Anabaena* associated with ferns, palms, lichens and hornwort, and many other plant-microbe symbiotic systems identifiable by a person of ordinary skill in the art.

In particular, in embodiments herein described hopanoids producing nitrogen-fixing bacteria capable of producing $C_{35}$ hopanoids are rhizobia that can be used alone or in combination with $C_{35}$ hopanoids to stimulate growth of leguminous plants and/or fertilize a soil.

1 The term "leguminous plants" or "legumes" indicates plants in the family of Fabaceae (or Leguminosae) with taxa such as kudzu, clovers, soybeans, alfalfa, lupines, peanuts and rooibos. Examples of leguminous plants include including *Vicia faba, Arachis hypogaea, Cicer arientum, Dolichos lablab, Lupinus albus, Pisum arvense, Glycine max, Cajanus cajan, Lens esculenta, Vigna radiate, Cyamopsis tetragonoloba, Vigna aconitifolius, Vicia hirsute, Trigonella foenum-graecum, Onobrychis sativa, Coronilla cretica, Ornithopus sativus, Desmodium intortum, Indigofera hirsute, Medicago sativa, Trifolium incarnatum, Lotus pedunculatus, Trifolium agrarium* and *Lotonois bainesii* and others identifiable to a person of ordinary skill in the relevant art. Plants in the legume family can form symbioses with nitrogen-fixing soil bacteria to provide a sustainable nitrogen source to improve fertility in agricultural settings. Most legumes interact optimally with nitrogen-fixing bacteria of a single genus, although the specificities of legumes for bacterial partners are largely uncharacterized. The nitrogen-fixing rhizobia that form symbioses with a given legume are referred to as legume symbionts. Examples of legume symbionts include *Bradyrhizobia, Rhizobiacaea, Phyllobacteria, Sinorhizobia (Ensifer), Mesorhizobia* and *Azorhizobia*.

The term "rhizobia" as used herein indicates a family of Gram-negative soil bacteria that fix nitrogen in association with plants. Rhizobia form an endosymbiotic nitrogen fixing association with roots of legumes and some trees including *Acacia* and *Parasponia*. In particular, rhizobia colonize plant cells within root nodules where they convert atmospheric nitrogen into ammonia and then provide organic nitrogenous compounds such as glutamine or ureides to the plant. The plant in turn provides the bacteria with organic compounds made by photosynthesis. Most of the rhizobia species are in the Rhizobiacae family in the alpha-proteobacteria and are in *Rhizobium, Mesorhizobium, Ensifer*, or *Bradyrhizobium* genera. There are also some other rhizobial species, presumably arisen through lateral gene transfer of symbiotic genes. In general, rhizobia consists of about 98 species in 13 genera, including *Rhizobium, Mesorhizobium, Ensifer, Bradyrhizobium, Burkholderia, Phyllobacterium, Microvirga, Ochrobactrum, Methylobacterium, Cupriavi-*

*dus, Devosia*, and *Shinella*. Detailed taxonomic information about rhizobia are identifiable by a person of ordinary skill in the *Azorhizobium*, art.

In particular, in embodiments here described rhizobia used in biofertilizers, and related seeds compositions, methods and systems are naturally capable of producing $C_{35}$ hopanoids. Exemplary legume symbionts naturally capable of producing $C_{35}$ hopanoids include *Bradyrhizobium* BTAi1, *Bradyrhizobium japonicum, Bradyrhizobium diazoefficiens, Bradyrhizobium* ORS278 and *Methylobacterium nodulans*. Exemplary legume symbionts naturally incapable of producing $C_{35}$ hopanoids but capable of being engineered to produce $C_{35}$ hopanoids include *Rhizobium etli, Rhizobium leguminosarum, Mesorhizobium loti, Sinorhizobium meliloti, Azorhizobium caulinodans*, and *Ochrobactrum anthropi*. The symbiotic relationship between these and other exemplary legume symbionts and their host plants, is shown in Table 1. Table 1 also includes an indication whether the rhizobia strain contains the hpnH gene that is required for the $C_{35}$ biosynthesis.

TABLE 1

Symbiotic relationship between exemplary legume symbionts and their host plants and whether the hpnH gene is present in the rhizobia strain

| Rhizobia | Native host(s) | hpnH present |
|---|---|---|
| (Para)*Burkholderia caribensis* | *Mimosa* spp. | YES |
| (Para)*Burkholderia mimosarum* | *Mimosa* spp. | YES |
| (Para)*Burkholderia nodosa* | *Mimosa* spp. | NO |
| (Para)*Burkholderia phymatum* | *Aspalathus carnosa* | YES |
| *Azorhizobium caulinodans* | *Sesbonia* pp., e.g. *Sesbania rostrata* | NO |
| *Azorhizobium doebereinerae* | *Sesbania virgata* | NO |
| *Bradyrhizobium* BTAi1 | *Aeschynomene indica, Aeschynomene evenia* | YES |
| *Bradyrhizobium canariense* | *Lupinus* spp. | UNKNOWN |
| *Bradyrhizobium cytisi* | *Cytisus villosus* | UNKNOWN |
| *Bradyrhizobium denitrificans* | *Aeschynomene indica* | UNKNOWN |
| *Bradyrhizobium elkanii* | *Glycine soja* | YES |
| *Bradyrhizobium iriomotense* | *Entada koshunensis* | YES |
| *Bradyrhizobium japonicum* | *Glycine Max* | YES |
| *Bradyrhizobium jicamae* | *Pachyrhizus erosus* | YES |
| *Bradyrhizobium liaoningense* | *Glycine* spp. | YES |
| *Bradyrhizobium manausense* | *Vigna unguiculata* | UNKNOWN |
| *Bradyrhizobium neotropicale* | *Centrolobium paraense* | UNKNOWN |
| *Bradyrhizobium* sp. ORS278 | *Aeschynomene evenia, Aeschynomene indica* | YES |
| *Bradyrhizobium* sp. ORS285 | *Aeschynomene afraspera* | YES |
| *Bradyrhizobium pachyrhizi* | *Pachyrhizus erosus* | YES |
| *Bradyrhizobium paxllaeri* | *Phaseolus lunatus* L. | UNKNOWN |
| *Bradyrhizobium retamae* | *Retama* spp. | UNKNOWN |
| *Bradyrhizobium subterraneum* | *Arachis hypogea* L. | UNKNOWN |
| *Bradyrhizobium yuanmingense* | *Lespedeza* spp. | YES |
| *Bradyrhizovbium diazoefficiens* | *Glycine max* | YES |
| *Burkholderia cepacia* | *Mimosa* spp. | YES |
| *Burkholderia sabiae* | *Mimosa* spp. | UNKNOWN |
| *Burkholderia tuberum* | *Aspalathus carnosa* | UNKNOWN |
| *Cupriavidus taiwanensis* | *Mimosa* spp. | YES |
| *Devosia neptuniae* | *Neptunia natans* | UNKNOWN |
| *Mesorhizobium abyssinicae* | *Acacia abyssinica* | UNKNOWN |
| *Mesorhizobium albiziae* | *Albizia kalkora* | UNKNOWN |
| *Mesorhizobium alhagi* | *Alhagi sparsifolia* | NO |
| *Mesorhizobium amorphae* | *Amorpha fruticosa* | NO |
| *Mesorhizobium australicum* | *Biserrula pelecinus* L. | NO |
| *Mesorhizobium camelthorni* | *Alhagi sparsifolia* | UNKNOWN |
| *Mesorhizobium caraganae* | *Caragana* spp. | UNKNOWN |
| *Mesorhizobium chacoense* | *Prosopis alba* | UNKNOWN |
| *Mesorhizobium ciceri* | *Cicer arietinum* L. | NO |
| *Mesorhizobium erdmanii* | *Lotus* spp. | NO |
| *Mesorhizobium gobiense* | *Glycyrrhiza uralensis, Lotus corniculatus, Oxytropis glabra* and *Robinia pseudoacacia* | UNKNOWN |
| *Mesorhizobium hawassense* | *Acacia* spp. | UNKNOWN |
| *Mesorhizobium huakuii* | *Thermopsis lupinoides* | NO |
| *Mesorhizobium jarvisii* | *Lotus* spp. | UNKNOWN |
| *Mesorhizobium loti* | *Lotus* spp., e.g *Lotus japonicus* | NO |
| *Mesorhizobium mediterraneum* | *Cicer arietinum* L. | UNKNOWN |
| *Mesorhizobium metallidurans* | *Anthyllis vulneraria* | NO |
| *Mesorhizobium muleiense* | *Cicer arietinum* L. | UNKNOWN |

TABLE 1-continued

Symbiotic relationship between exemplary legume symbionts and their host plants and whether the hpnH gene is present in the rhizobia strain

| Rhizobia | Native host(s) | hpnH present |
|---|---|---|
| Mesorhizobium opportunistum | Biserrula pelecinus L. | NO |
| Mesorhizobium plurifarium | Acacia spp. | NO |
| Mesorhizobium qingshengii | Astragalus sinicus | UNKNOWN |
| Mesorhizobium robiniae | Robinia pseudoacacia | UNKNOWN |
| Mesorhizobium sangaii | Astragalus spp. | UNKNOWN |
| Mesorhizobium septentrionale | Astragalus adsurgens | UNKNOWN |
| Mesorhizobium shangrilense | Caragana spp. | UNKNOWN |
| Mesorhizobium shonense | Acacia spp. | UNKNOWN |
| Mesorhizobium silamurunense | Caragana spp. | UNKNOWN |
| Mesorhizobium tamadayense | Anagyris latifolia and Lotus berthelotii | UNKNOWN |
| Mesorhizobium tarimense | Glycyrrhiza uralensis, Lotus corniculatus, Oxytropis glabra and Robinia pseudoacacia | UNKNOWN |
| Mesorhizobium temperatum | Astragalus adsurgens | UNKNOWN |
| Mesorhizobium tianshanense | Vicia spp., Trifolium spp. | UNKNOWN |
| Methylobacterium nodulans | Crotalaria spp. | YES |
| Microvirga lotononidis | Listia angolensis | NO |
| Microvirga lupini | Lupinus texensis | NO |
| Microvirga zambiensis | Listia angolensis | UNKNOWN |
| Ochrobactrum_anthropi | Cicer arietinum | |
| Ochrobactrum ciceri | Cicer arietinum | UNKNOWN |
| Ochrobactrum cytisi | Cytisus scoparius | UNKNOWN |
| Ochrobactrum lupini | Lupinus albus | UNKNOWN |
| Phyllobacterium ifriqiyense | Astragalus algerianus, Lathyrus numidicus | UNKNOWN |
| Phyllobacterium leguminum | Argyrolobium uniflorum, Astragalus algerianus | UNKNOWN |
| Phyllobacterium trifolii | Trifolium spp. and Lupinus spp. | UNKNOWN |
| Rhizobium alamii | Medicago ruthenica | NO |
| Rhizobium alkalisoli | Caragana intermedia | UNKNOWN |
| Rhizobium azibense | Phaseolus vulgaris | UNKNOWN |
| Rhizobium calliandrae | Calliandra grandiflora | UNKNOWN |
| Rhizobium cauense | Kummerowia stipulacea | UNKNOWN |
| Rhizobium cellulosilyticum | Medicago sativa | UNKNOWN |
| Rhizobium daejeonense | Medicago sativa | UNKNOWN |
| Rhizobium endophyticum | Phaseolus vulgaris | UNKNOWN |
| Rhizobium etli | Phaseolus vulgaris L. | NO |
| Rhizobium fabae | Vicia faba | UNKNOWN |
| Rhizobium freirei | Phaseolus vulgaris | NO |
| Rhizobium galegae | Galega orientalis | UNKNOWN |
| Rhizobium gallicum | Phaseolus vulgaris | NO |
| Rhizobium giardinii | Phaseolus vulgaris | NO |
| Rhizobium grahamii | Dalea leporina, Leucaena leucocephala and Clitoria ternatea | NO |
| Rhizobium hainanense | Hainan province legumes | UNKNOWN |
| Rhizobium halophytocola | Rosa rugosa | UNKNOWN |
| Rhizobium herbae | Various wild legumes in China | UNKNOWN |
| Rhizobium huautlense | Sesbania herbacea | UNKNOWN |
| Rhizobium indigoferae | Indigofera spp. | UNKNOWN |
| Rhizobium jaguaris | Calliandra grandiflora | UNKNOWN |
| Rhizobium laguerreae | Vicia faba | UNKNOWN |
| Rhizobium leguminosarum | Phaseolus vulgaris, Trifolium spp. Pisum sativum | NO |
| Rhizobium leucaenae | Leucaena leucocephala, Leucaena esculenta, common beans (Phaseolus vulgaris) and Gliricidia sepium | NO |
| Rhizobium loessense | Astragalus and Lespedeza | UNKNOWN |
| Rhizobium lusitanum | Phaseolus vulgaris | NO |
| Rhizobium mayense | Calliandra grandiflora | UNKNOWN |
| Rhizobium mesoamericanum | Phaseolus vulgaris, siratro, cowpea and Mimosa pudica | NO |
| Rhizobium mesosinicum | Albizia, Kummerowia and Dalbergia | UNKNOWN |
| Rhizobium miluonense | Lespedeza | NO |
| Rhizobium mongolense | Medicago ruthenica | NO |
| Rhizobium multihospitium | Robinia pseudoacacia | NO |
| Rhizobium oryzae | Phaseolus vulgaris and Glycine max | UNKNOWN |
| Rhizobium paranaense | Phaseolus vulgaris L. | UNKNOWN |
| Rhizobium petrolearium | Medicago sativa | UNKNOWN |
| Rhizobium phaseoli | Phaseolus vulgaris | NO |
| Rhizobium pisi | Pisum sativum | UNKNOWN |
| Rhizobium sophorae | Sophora flavescens | UNKNOWN |
| Rhizobium sophoriradicis | Sophora flavescens | UNKNOWN |
| Rhizobium sphaerophysae | Sphaerophysa salsula | UNKNOWN |
| Rhizobium sullae | Hedysarum coronarium L. | NO |

TABLE 1-continued

Symbiotic relationship between exemplary legume symbionts and their host plants and whether the hpnH gene is present in the rhizobia strain

| Rhizobia | Native host(s) | hpnH present |
|---|---|---|
| Rhizobium taibaishanense | Kummerowia striata | UNKNOWN |
| Rhizobium tibeticum | Trigonella archiducis-nicolai, Medicago lupulina, Medicago sativa, Melilotus officinalis, Phaseolus vulgaris and Trigonella foenum-graecum | UNKNOWN |
| Rhizobium tropici | Phaseolus vulgaris L. beans and Leucaena sp. trees | NO |
| Rhizobium tubonense | Oxytropis glabra | UNKNOWN |
| Rhizobium undicola | Neptunia natans | NO |
| Rhizobium vallis | Phaseolus vulgaris, Mimosa pudica and Indigofera spicata | UNKNOWN |
| Rhizobium vignae | Vigna radiata | NO |
| Rhizobium yanglingense | Phaseolus vulgaris | UNKNOWN |
| Shinella kummerowiae | Kummerowia stipulacea | UNKNOWN |
| Sinorhizobium/Ensifer abri | Abrus precatorius | UNKNOWN |
| Sinorhizobium/Ensifer adhaerens | Lotus arabicus | UNKNOWN |
| Sinorhizobium/Ensifer americanum | Acacia spp. | NO |
| Sinorhizobium/Ensifer arboris | Acacia senegal and Prosopis chilensis | NO |
| Sinorhizobium/Ensifer fredii | Glycine Max | NO |
| Sinorhizobium/Ensifer garamanticus | Argyrolobium uniflorum, Medicago sativa | UNKNOWN |
| Sinorhizobium/Ensifer indiaense | Sesbania rostrata | UNKNOWN |
| Sinorhizobium/Ensifer kostiensis | Acacia senegal and Prosopis chilensis | UNKNOWN |
| Sinorhizobium/Ensifer kummerowiae | Kummerowia stipulacea | UNKNOWN |
| Sinorhizobium/Ensifer medicae | Medicago spp. | NO |
| Sinorhizobium/Ensifer meliloti | Medicago spp., e.g. Madicago truncatula | NO |
| Sinorhizobium/Ensifer mexicanus | Acacia angustissima | UNKNOWN |
| Sinorhizobium/Ensifer morelense | Leucaena leucocephala | UNKNOWN |
| Sinorhizobium/Ensifer numidicus | Argyrolobium uniflorum, Lotus creticus | UNKNOWN |
| Sinorhizobium/Ensifer saheli | Sesbania cannabina | NO |
| Sinorhizobium/Ensifer sesbaniae | Sesbania spp. | UNKNOWN |
| Sinorhizobium/Ensifer sojae | Glycine max | NO |
| Sinorhizobium/Ensifer terangae | Acacia laeta | NO |

In some embodiments, the nitrogen-fixing rhizobia naturally capable of producing C35 hopanoids can comprise Bradyrhizobia. Bradyrhizobia are Gram-negative bacilli (rod shaped) with a single subpolar or polarflagellum. Bradyrhizobia are a common soil dwelling microorganism that can form symbiotic relationships with leguminous plant species. Many members of this genus have the ability to fix atmospheric nitrogen by forming either specific or general symbioses. This means that one species of Bradyrhizobium can only be able to nodulate one legume species, whereas other Bradyrhizobium species can be able to nodulate several legume species.

Exemplary Bradyrhizobia naturally capable of producing $C_{35}$ hopanoids and that are suitable to be used in biofertilizer, compositions, seeds, methods and systems herein described include Bradyrhizobium diazoefficiens, Bradyrhizobium elkanii, Bradyrhizobium embrapense, Bradyrhizobium icense, Bradyrhizobium japonicum, Bradyrhizobium jicamae, Bradyrhizobium lablabi, Bradyrhizobium liaoningense, Bradyrhizobium manausense, Bradyrhizobium neotropicale, Bradyrhizobium oligotrophicum, Bradyrhizobium pachyrhizi, Bradyrhizobium paxllaeri, Bradyrhizobium retamae, Bradyrhizobium stylosanthis, Bradyrhizobium tropiciagri, Bradyrhizobium valentinum, Bradyrhizobium viridifuturi, Bradyrhizobium yuanmingense, Bradyrhizobium sp., Bradyrhizobium sp. Aila-2, Bradyrhizobium sp. ARR65, Bradyrhizobium sp. AT1, Bradyrhizobium sp. BR 10245, Bradyrhizobium sp. BR 10303, Bradyrhizobium sp. BTAi1, Bradyrhizobium sp. CCBAU 15544, Bradyrhizobium sp. CCBAU 15635, Bradyrhizobium sp. CCBAU 43298, Bradyrhizobium sp. CCGE-LA001, Bradyrhizobium sp. CCH5-F6, Bradyrhizobium sp. Cp5.3, Bradyrhizobium sp. DFCI-1, Bradyrhizobium sp. DOA1, Bradyrhizobium sp. DOA9, Bradyrhizobium sp. Ec3.3, Bradyrhizobium sp. err11, Bradyrhizobium sp. G22, Bradyrhizobium sp. Leaf396, Bradyrhizobium sp. LMTR 3, Bradyrhizobium sp. LTSP849, Bradyrhizobium sp. LTSP857, Bradyrhizobium sp. LTSP885, Bradyrhizobium sp. LTSPM299, Bradyrhizobium sp. ORS 278, Bradyrhizobium sp. ORS 285, Bradyrhizobium sp. ORS 375, Bradyrhizobium sp. S23321, Bradyrhizobium sp. STM 3809, Bradyrhizobium sp. STM 3843, Bradyrhizobium sp. th.b2, Bradyrhizobium sp. Tv2a-2, Bradyrhizobium sp. URHA0002, Bradyrhizobium sp. URHA0013, Bradyrhizobium sp. URHD0069, Bradyrhizobium sp. WSM1253, Bradyrhizobium sp. WSM1417, Bradyrhizobium sp. WSM1743,

*Bradyrhizobium* sp. WSM2254, *Bradyrhizobium* sp. WSM2793, *Bradyrhizobium* sp. WSM3983, *Bradyrhizobium* sp. WSM4349, *Bradyrhizobium* sp. WSM471, and *Bradyrhizobium* sp. YR681.

In particular, in some embodiments *Bradyrhizobia* that are naturally capable of producing $C_{35}$ hopanoids that can be used in biofertilizer and related seeds compositions, methods and systems can include *Bradyrhizobium* BTAi1, *Bradyrhizobium* diazoefficiens USDA 110, *Bradyrhizobium japonicum* USDA 6, *Bradyrhizobium* sp. ORS 278, and *Bradyrhizobium* diazoefficiens.

In some of those embodiments, the nitrogen-fixing *Bradyrhizobium* naturally capable of producing hopanoids that can be used in biofertilizer and related seeds compositions, methods and systems is *Bradyrhizobium* diazoefficiens. The *Bradyrhizobium* diazoefficiens is a member of the *Bradyrhizobium* genus, having the ability to form root nodules on leguminous plants.

Figure 3:
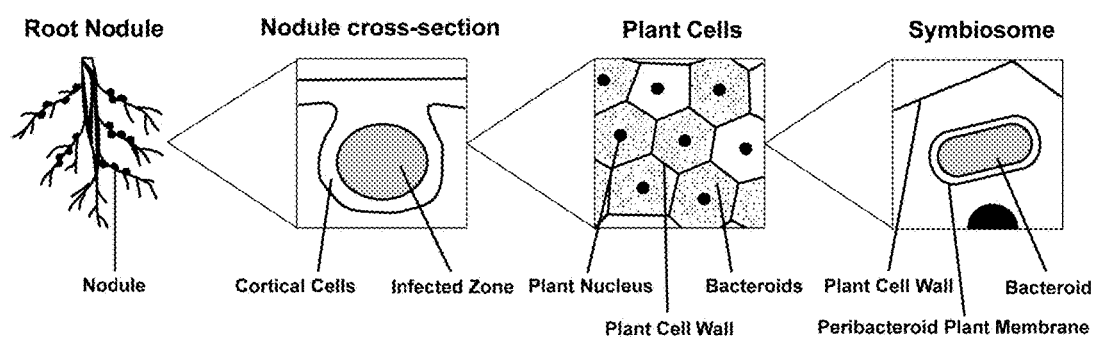
FIG. 3 shows in some embodiments the endosymbiotic context of B. diazoefficiens within root nodules of A. afraspera. B. diazoefficiens exists as a bacteroid, a terminally differentiated enlarged, elongated and polyploid state, within infected plant cortical cells. In addition to its own membrane, each bacteroid is surrounded by a peribacteroid plant-derived membrane. The double-layered bacteroid is called a symbiosome. The infected plant cell niche is characterized by low $O_2$, low pH, hyperosmosis and oxidative stress [1, 2].

In particular, in embodiments herein described *B. diazoefficiens* can exhibit two different life-styles, free-living in soil or symbiotic within legume root nodule cells [2, 20]. In addition to its native soybean host, *B. diazoefficiens* can engage in nitrogen-fixing symbioses with the stems and roots of the tropical legume *Aeschynomene afraspera* [21]. In both of the these hosts, development of the symbiosis progresses through a series of defined stages: (i) colonization and invasion of host root tissue; (ii) internalization of bacteria by plant cells to form an organelle-like structure called the symbiosome, comprising endosymbiotic bacterial cells termed "bacteroids" that are surrounded by a plant-derived "peribacteroid" membrane (FIG. 3); and (iii) initiation of nitrogen fixation by bacteroids, during which there is a high rate of nutrient exchange across the symbiosome membranes between plant-supplied carbon sources and fixed atmospheric nitrogen produced by bacterial nitrogenase [2, 22].

In some embodiments, nitrogen fixing $C_{35}$ producing rhizobia to be used in biofertilizer, compositions, seeds methods and systems herein described are rhizobia naturally incapable of producing $C_{35}$ hopanoids (herein also $C_{35}$ hopanoid-deficient rhizobia), and genetically engineered to include genes for production of $C_{35}$ hopanoids thus providing genetically engineered rhizobia capable of producing $C_{35}$ hopanoids herein also indicated as genetically engineered C35 rhizobia.

In some embodiments, the rhizobia naturally incapable of producing $C_{35}$ is a bacteria closely genetically related to (i.e. within a same taxonomic order of) hopanoids-producing legume symbionts capable of producing $C_{35}$ hopanoids that can be used in biofertilizers, compositions, methods and systems herein described. For example, a rhizobium naturally incapable of producing $C_{35}$ hopanoids that can be genetically modified in the sense of the disclosure comprise *Sinorhizobium meliloti*, a symbiont of alfalfa (*Medicago* spp.), which is closely genetically related to *Bradyrhizobia* and to all other members of the Rhizobiales order of the alpha proteobacteria having nitrogen-fixing capability in symbioses with plants.

In embodiments herein described, nitrogen-fixing rhizobia capable of producing $C_{35}$ either naturally or following genetic modification, can be used as biofertilizer for legumes and/or soil. The term "biofertilizer" as used herein refers to a substance containing living microorganisms, which, when applied to seeds, plant surfaces, or soil, colonizes the rhizosphere or the interior of the plant and/or promotes growth by increasing the supply or availability of primary nutrients to the host plant. Biofertilizers in the sense of the disclosure adds nutrients through the natural processes of nitrogen fixation, solubilizing phosphorus, and stimulating plant growth through the synthesis of growth-promoting substances.

Biofertilizers herein described comprise and in particular essentially consist of nitrogen fixing rhizobia capable of producing $C_{35}$ hopanoids. In particular, in biofertilizers essentially consisting of nitrogen fixing rhizobia capable of producing $C_{35}$ hopanoids herein described, at least 70%, preferably at least 80%, more preferably at least 85%, even more preferably at least 90%, and more preferably at least 95%, of the nutrient adding activity of the biofertilizer is performed by nitrogen fixing rhizobia capable of producing $C_{35}$ hopanoids. The nutrient adding activity of a bacteria and/or the biofertilizer can be quantitatively detected by detecting with techniques identifiable by a skilled person the nitrogen fixed by the plant or soil, the nitrogen solubilized in the plant or soil and/or a difference in plant growth, following addition of the biofertilizer and/or of each rhizobia strains. In general, nitrogen detection can be performed by quantitatively detecting the percentage of the nitrogen dry weight by spectrometry on a dry sample of soil and/or the plants. Additional techniques comprise use of biosensors that use a fluorescent label or other label that can be incubated with a dried sample to report on the amount of glutamine (the main form of fixed $N_2$) or other forms of fixed $N_2$ as will be understood by a skilled person The terms "detect" or "detection" as used herein indicates the determination of the existence, presence or fact of a compound, bacteria and/or related activity in a limited portion of space, including but not limited to a sample, a reaction mixture, and a substrate. The "detect" or "detection" as used herein can comprise determination of chemical and/or biological properties of a bacteria, plant, soil and or related compositions, including but not limited to ability to fixing nitrogen, solubilize nitrogen promote growth and additional properties identifiable by a skilled person upon reading of the present disclosure. The detection can be quantitative or qualitative. A detection is "quantitative" when it refers, relates to, or involves the measurement of quantity or amount of the compound, bacteria and/or related activity (also referred as quantitation), which includes but is not limited to any analysis designed to determine the amounts or proportions of the compound, bacteria and/or related activity. A detection is "qualitative" when it refers, relates to, or involves identification of a quality or kind of the target or s compound, bacteria and/or related activity signal in terms of relative abundance to another compound, bacteria and/or related activity, which is not quantified.

The terms "label" and "labeled molecule" as used herein refer to a molecule capable of detection, including but not limited to radioactive isotopes, fluorophores, chemiluminescent dyes, chromophores, enzymes, enzymes substrates, enzyme cofactors, enzyme inhibitors, dyes, metal ions, nanoparticles, metal sols, ligands (such as biotin, avidin, streptavidin or haptens) and the like. The term "fluorophore" refers to a substance or a portion thereof which is capable of exhibiting fluorescence in a detectable image. As a consequence, the wording "labeling signal" or signal as used herein indicates the signal emitted from the label that allows detection of the label, including but not limited to radioactivity, fluorescence, chemiluminescence, production of a compound in outcome of an enzymatic reaction and the like.

In embodiments herein described a biofertilizer for a leguminous plant can be produced by providing a nitrogen fixing rhizobium in a form suitable for administration to a leguminous plant or seed or soil surrounding a leguminous plant or seed. In particular, the nitrogen-fixing rhizobium can be provided in a biofertilizer in a culture in a viable form and preferably in a culture with a percentage of live cells in a whole population that can be at least 5%, preferably at least 25% and more preferably at least 50%

A skilled person will be able to identify different type of rhizobia and related application including specific condition for related viability. For example *B. diazoefficiens* differs phylogenetically from *Bradyrhizobium* BTAi1 as for example, Shc from these two strains falls in distinct phylogenetic clades [7]. Unlike *Bradyrhizobium* BTAi1, *B. diazoefficiens* is unable to photosynthesize [23, 24]. Moreover, *B. diazoefficiens* infects plants via a Nod-factor dependent pathway, whereas *Bradyrhizobium* BTAi1 uses alternate symbiotic strategies [25]. The inability to delete shc in *B. diazoefficiens* suggests that hopanoids are essential in this species, in contrast to *Bradyrhizobium* BTAi1 where shc mutants are viable. Such difference between these two species likely reflects differences in the niches the two bacteria inhabit as a consequence of their metabolic differences, and what is required for survival therein.

In some embodiments, the nitrogen fixing rhizobia can be provided in the biofertilizer in an isolated and/or purified form wherein the bacteria are provided without a detectable presence of other microorganism. A bacterial strain in isolated form can be obtained by obtaining a clonal bacterial preparation of the bacteria, for example by inoculating a bacterial sample into a culture plate, and picking a single bacterial colony grown on the plate as will be understood by a skilled person. A purified bacterial strain can be obtained for example by separating bacteria from a growth medium, with methods identifiable by a skilled person such as inoculating a bacterial culture broth with an isolated bacterial colony, growing the culture, and subsequently separating the bacteria from the medium (e.g. by centrifugation and discarding the supernatant medium, while retaining the pelleted bacteria). Additional techniques to isolate or purify bacteria are identifiable by a skilled person upon reading of the present disclosure.

In some embodiments, a biofertilizer for leguminous plant can be provided from one or more candidate nitrogen fixing rhizobia strains, by a method comprising: detecting among the one or more candidate nitrogen fixing rhizobia strains, at least one rhizobia strain capable of producing $C_{35}$ hopanoids. The method further comprises providing the at least one rhizobia strain capable of producing $C_{35}$ hopanoids in a form suitable for administration to a leguminous plant or seed or soil surrounding a leguminous plant or seed.

In some embodiments, detecting rhizobia strains capable of producing $C_{35}$ hopanoids in natural samples can be performed by culture-independent techniques, such as 16S rDNA sequencing. Positive identification in this manner can then be used to target particular samples for enrichment of Rhizobia strains, followed by isolation using methods described below.

In particular, detecting among the one or more candidate nitrogen fixing rhizobia strains, at least one rhizobia strain capable of producing $C_{35}$ hopanoids can be performed by detecting $C_{35}$ hopanoids production by the one or more candidate compounds For example, $C_{35}$ hopanoids analysis can be performed by routine extraction and analysis using either high temperature GC-MS or ultra-performance LC-MS as well as other approaches identifiable to a skilled person in the art. Detailed protocol of hopanoid analysis can be found for example in related publications such as Welander et al., 2009 [11] or Neubauer et al., 2015 [26] as well as in Example 6 of the present disclosure.

In some embodiments detecting among the one or more candidate nitrogen fixing rhizobia strains, detecting at least one rhizobia strain capable of producing $C_{35}$ hopanoids can be performed by detecting genes for the synthesis of $C_{35}$ hopanoids in the one or more candidate one rhizobia strain.

In some embodiments, detecting genes for synthesis of $C_{35}$ hopanoids in the one or more candidate rhizobia strains can be performed by detecting sequences of one or more of the shc, hpnH and hpnG, hpnO, as well as hpnP, and also hpnC, hpnD and hpnE, in the genome, transcriptome, or proteome of the one or more candidate strains. Exemplary techniques that can be used to detecting sequences of one more genes (e.g. where the genome is known), comprises computer-based tools for comparing gene sequences, transcript sequences, or protein sequences, such as those using the Basic Local Alignment Search Tool (BLAST) or any other similar methods known to those of ordinary skill in the art.

In some embodiments, detecting genes for synthesis of $C_{35}$ hopanoids in the one or more candidate rhizobia strains can be performed by detecting the genes and/or related transcript in the one or more candidate rhizobia. Exemplary techniques comprise wet bench approaches such as DNA sequencing, PCR, Southern blotting, DNA microarrays, or other methods of hybridization of DNA or RNA probes to DNA, wherein probes are attached to a label capable of emitting a signal such as radiolabeling, fluorescence, luminescence, mass spectroscopy or colorimetric methods. Exemplary probes that can be used comprise primers from known shc, hpnH and hpnG, hpnO, as well as hpnP, hpnC, hpnD and/or hpnE, and/or related transcript as will be understood by a skilled person.

In some embodiments, detecting genes for synthesis of $C_{35}$ hopanoids in the one or more candidate rhizobia strains can be performed by detecting transcripts of shc, hpnH and hpnG, hpnO, as well as hpnP, and/or also hpnC, hpnD and/or hpnE. Exemplary techniques comprise RNA sequencing, PCR, quantitative PCR, Northern blotting, in situ hybridization, RNA microarrays, or other methods of hybridization of DNA or RNA probes to RNA.

In some embodiments, detecting genes for synthesis of $C_{35}$ hopanoids in the one or more candidate rhizobia strains can be performed by detecting proteins encoded by shc, hpnH and hpnG, hpnO, as well as hpnP, and/or also hpnC, hpnD and/or hpnE detecting the proteins. Exemplary techniques comprise proteomics, antibody-based methods including immunohistochemistry, immunofluorescence, western blotting, or any other method of protein detection.

In embodiments, herein described, the conditions and parameters to use probes/primers to detect shc, hpnH and hpnG, hpnO, as well as hpnP, hpnC, hpnD and/or hpnE, can be varied to permit lower or higher threshold or stringency of detection, to ensure hybridization within the least 55% sequence identity at gene level in view of the specific primers/probes selected. For example, use of oligonucleotides comprising one or more degenerated nucleotide bases or or using an antibody that binds to more highly conserved protein regions, can require modification of the detection conditions as will be understood by a skilled person.

In some embodiments, detecting genes for synthesis of $C_{35}$ hopanoids in the one or more candidate rhizobia strains can be performed by detecting C35 hopanoids in lipid fractions or other cellular fractions isolated from cells using methods mass spectrometry.

In an exemplary embodiment, the detection can be done, for example, by isolating genomic DNA from a candidate and performing PCR using primer sequences designed to amplify hpnH genes from known $C_{35}$ hopanoid-producing rhizobia, including the primers listed in Table 4. Alternatively, RNA samples can be isolated from the candidate(s) and these transcripts can be sequenced, and expression of the hpnH gene can be detected by identification of this gene using homology-based computational identification (e.g. BLAST).

In some embodiments, providing the at least one rhizobia strain capable of producing $C_{35}$ hopanoids in a form suitable for administration to a leguminous plant or seed or soil surrounding a leguminous plant or seed, can be performed by providing the at least one rhizobia strain in a culture in a viable form and preferably in a culture containing a percentage of live cells in a whole population that is at least 5%, preferably at least 25% and more preferably at least 50%. In some embodiment providing the at least one rhizobia strain capable of producing $C_{35}$ hopanoids in a form suitable for administration to a leguminous plant or seed or soil surrounding a leguminous plant or seed, in an isolated or purified form wherein the bacteria are provided without a detectable presence of other microorganism.

In some embodiments a biofertilizer for a leguminous plant can be provided from a rhizobium naturally incapable of producing $C_{35}$ hopanoids, by a method comprising: genetically engineering a nitrogen fixing rhizobia strain incapable of producing $C_{35}$ hopanoids to introduce $C_{35}$ synthesis genes to provide a genetically engineered nitrogen fixing rhizobia strains capable of producing $C_{35}$ hopanoids, and providing the genetically engineered nitrogen fixing rhizobia strains in a form suitable for administration to a leguminous plant or seed, and/or a soil surrounding leguminous plant or seed.

In some of those embodiments, genetically engineering a nitrogen fixing rhizobia strain incapable of producing $C_{35}$ hopanoids to introduce $C_{35}$ synthesis genes can be performed by providing at least one gene selected from shc, hpnH and hpnG, hpnO, as well as hpnP, hpnC, hpnD and hpnE and introducing the at least one gene in the rhizobium incapable of producing $C_{35}$ hopanoids for a time and under conditions to allow expression of the at least one gene.

In some of those embodiments, genetically engineering a nitrogen fixing rhizobia strain incapable of producing $C_{35}$ hopanoids to introduce $C_{35}$ synthesis genes can be performed by obtaining $C_{35}$ hopanoid synthesis genes from rhizobium that naturally produces $C_{35}$ hopanoid using polymerase chain reaction-based amplification and isolation of a region of genomic DNA encoding hopanoid synthesis genes and/or genomic regulatory elements, or cDNA encoding hopanoid synthesis genes (see Examples 22-27). In some embodiments, the introduction of $C_{35}$ hopanoid synthesis genes into $C_{35}$ hopanoid-deficient rhizobia to produce genetically engineered C35 rhizobia can be performed by transduction using a recombinant viral vector containing a $C_{35}$ hopanoid synthesis gene expression construct.

Additional techniques and related vectors, methods and systems to modify a nitrogen fixing rhizobia incapable of producing C35 are identifiable by a skilled person.

In some embodiments, providing the genetically engineered nitrogen fixing rhizobia strains in a form suitable for administration to a leguminous plant or seed, and/or a soil surrounding leguminous plant or seed can be performed by providing the at least one genetically engineered rhizobia strain in a culture in a viable form and preferably in a culture a percentage of live cells in a whole population can be at least 5%, preferably at least 25% and more preferably at least 50%. In some embodiment providing the at least one genetically engineered rhizobia strain capable of producing $C_{35}$ hopanoids in a form suitable for administration to a leguminous plant or seed or soil surrounding a leguminous plant or seed, in an isolated or purified form wherein the bacteria are provided without a detectable presence of other microorganism.

In several embodiments, one or more biofertilizers of the present disclosure are comprised in a biofertilizer composition together with one or more suitable vehicles, wherein the term "vehicle" as used herein indicates any of various media acting usually as solvents, carriers, binders or diluents for the biofertilizer that are comprised in the composition as an active ingredient.

In some embodiments, a biofertilizer composition for a leguminous plant comprises one or more biofertilizers essentially consisting of one or more nitrogen-fixing rhizobia capable of producing $C_{35}$ hopanoids and an acceptable vehicle. In some embodiments, the biofertilizer composition can further comprise one or more $C_{35}$ hopanoids. In the biofertilizer composition the one or more biofertilizers and the vehicle are formulated for administration to a leguminous plant and/or for administration to a leguminous seed. In some embodiments the biofertilizer composition is formulated for administration to a soil as will be understood by a skilled person.

In particular, in some embodiments in the biofertilizer compositions the vehicle comprises one or more carriers. Incorporation of carrier materials in the biofertilizer composition herein described can enable easy-handling, long-term storage and high effectiveness of the nitrogen-fixing capability of the nitrogen-fixing bacteria comprised in the biofertilizer composition. In particular, the suitable carrier material can allow gas exchange, also have high organic matter content and high water holding capacity, as well as provide a stable medium for the storage of the biofertilizer while retaining high viability of the nitrogen-fixing bacteria comprised therein as will be understood by a skilled person.

In particular, suitable carrier materials can enhance the survival of the nitrogen-fixing rhizobia on the seed surface against drying conditions until placed into soil, the survival of the bacteria during the storage period, as well as the survival of the bacteria in soil. After being introduced into the soil, the carrier material provides nutrient and/or habitable micro-pore to the inoculant bacteria for them to compete with native soil microorganisms.

Various types of carrier materials can be used for seed or soil inoculation. For preparation of seed inoculant, the carrier material can be milled to fine powder with particle size of 10-40 µm. The properties of a suitable carrier material for seed inoculation are (1) non-toxic to inoculant bacterial strain, (2) good moisture absorption capacity, (3) easy to process and free of lump-forming materials, (4) easy to sterilize by autoclaving or gamma-irradiation, (5) available in adequate amounts, (6) inexpensive, (7) good adhesion to seeds, and (8) good pH buffering capacity and (9) non-toxic to plant. Further information about carrier materials can be found in "Handbook for Rhizobia" (Somasegaran and Hoben, Springer, 1994).

The carrier can be a material, such as peat, vermiculite, lignite powder, clay, talc, rice bran, seed, rock phosphate pellet, charcoal, soil, paddy straw compost, wheat bran or a mixture of such materials. In common practice, for better shelf-life of biofertilizer formulation, a carrier or a mixture of such carrier materials are selected based on the viability of the microorganisms mixed with them. In some particular cases, to achieve a tight coating of inoculant on seed surface, adhesive material, such as gum Arabic, methylethylcellulose, sucrose solutions and vegetable oils, can be used as carrier. In some cases, supplementary nutrients and cell protectants such as sucrose, maltose, trehalose, molasses, glucose and glycerol can be used together with the carrier material to ensure improved cell viability and extended shelf-life.

In some embodiments, the biofertilizer composition comprises one or more nitrogen-fixing rhizobia capable of producing $C_{35}$ hopanoids and one or more $C_{35}$ hopanoids. In some embodiments the composition can be formulated for administration to a leguminous plant, a leguminous seed and/or soil surrounding the leguminous plant or leguminous seed.

In some embodiments, a biofertilizer composition can be formulated as an inoculant, wherein the term "inoculant" as used herein indicates a biofertilizer composition containing a bacterial culture capable of providing fixed nitrogen to plants, either via direct association (symbiosis) or via enrichment of the soil or medium in which the plant is grown.

In particular, in some embodiments, the biofertilizers formulation described herein can be prepared as carrier-based inoculants containing $C_{35}$ hopanoids, living $C_{35}$-hopanoids-producing nitrogen-fixing bacteria and a carrier, such as a $C_{35}$-bacteria-carrier mixture, according to common procedures as would be recognized by a person skilled in the art of agriculture and fertilizer applications.

In particular, in some embodiments, a biofertilizer composition formulated as an inoculant can be prepared by first harvesting log-phase cultures of diazotrophs in their appropriate free-living cultivation medium as described in literatures. For a given plant host, a concentrated solution of inoculation medium is prepared according to common procedures described in literatures, which typically contains the necessary elements for the nitrogenase reaction, such as molybdenum/vanadium, iron, sulfur-containing compounds. A concentrated $C_{35}$ hopanoid solution can be obtained by total lipid extraction of a rhizobia culture using Bligh-Dyer method [27] modified for large-scale extraction, followed by purification using silica gel and HPLC as would be understood by a skilled person in the art. Detailed description of methods for obtaining purified hopanoids from hopanoid-producing rhizobia can be found in related publications such as C-H Wu et. al. [28] herein incorporated by reference in its entirety.

In some embodiments, biofertilizer compositions herein described can optionally comprise also $C_{35}$ hopanoids and in particular $C_{35}$ hopanoids of Formula I. In particular, in embodiments herein described, $C_{35}$ hopanoids, and in particular $C_{35}$ hopanoids of Formula I, can be comprised in biofertilizer compositions together with $C_{35}$-hopanoids-producing nitrogen-fixing rhizobia naturally capable of producing hopanoids or with nitrogen fixing rhizobia naturally incapable of producing hopanoids and genetically engineered to produce $C_{35}$ hopanoids of Formula I can be combined at a weight ratio identifiable to a person of ordinary skill in the art of agriculture, in particular, in the art of fertilization.

In some embodiments, the biofertilizer or biofertilizer composition herein described can be used to stimulate plant growth with enhanced tolerance to the diverse stresses encountered during the progression of plant-microbe symbioses, including high temperature, oxic and hypoxic condition, acidic, detergent, and oxidative stresses.

In particular, herein provided are methods of fertilizing leguminous plants and/or soil with biofertilizer and/or related biofertilizer compositions herein described.

In some embodiments, the method comprises applying one or more biofertilizer and/or biofertilizer compositions herein described to a leguminous plant or soil surround a leguminous plant for a time and under conditions to allow symbiosis of the nitrogen-fixing rhizobia with the leguminous plant.

In some embodiments, the biofertilizer and/or biofertilizer compositions can be administered in combination with one or more $C_{35}$ hopanoids. In those embodiments, administering the biofertilizer and/or biofertilizer compositions and administering one or more $C_{35}$ hopanoids are further performed for a time and under conditions allowing interaction of the one or more $C_{35}$ hopanoids with the nitrogen-fixing rhizobia in the administered biofertilizer and/or biofertilizer compositions.

In some embodiments, applying the biofertilizer or biofertilizer composition alone or in combination with C35 hopanoids can be performed on the roots or to the soil in which the roots are present. In particular, the applying can be performed at any time in plant growth as will be understood by a skilled person.

In some embodiments, application on legumes of $C_{35}$ hopanoids, and $C_{35}$ hopanoids-producing rhizobia herein described and related biofertilizer composition, can be performed under conditions allowing extensive host control of bacteroid physiology and establishment of a specific host microenvironment, defined by low oxygen, low pH, hyperosmosis and oxidative stress [1]. For example, in *A. afraspera* application of $C_{35}$ hopanoids, and rhizobia herein described and related biofertilizer composition can be performed in connection with the plant's ability to produce nodule-specific, cysteine-rich antimicrobial peptides (NCRs) that induce differentiation of the bacteroid into an enlarged, elongated and polyploid state.

In some embodiments, application on legumes of biofertilizers, biofertilizer composition alone or in combination with $C_{35}$ hopanoids, can be performed for microaerobic growth and tolerance to diverse stresses of the rhizobia the symbiotic microenvironment, such as oxic and hypoxic condition, acidic (pH≤6), detergent, oxidative stresses (such as due to hydrogen peroxide), ambient (between 22° C. and 32° C.) and particularly higher temperatures (i.e. 37° C.<T<32° C.) and/or to promote to outer membrane rigidity (Examples 14-19 for *B. diazoefficients*).

In some embodiments a method of fertilizing leguminous plants can comprise coating and/or inoculating one or more seeds of the leguminous plant with one or more biofertilizer and/or biofertilizer compositions herein described. In some embodiments, the seeds can be coated with bacteria and desiccated for transport/storage. It is expected that coating or inoculating with hopanoids will improve bacterial survival of desiccation and long-term storage in a desiccated state. In some embodiments the method further comprises coating and/or inoculating one or more $C_{35}$ hopanoids before the coating and/or inoculating the one or more seeds of the leguminous plant with one or more biofertilizer and/or biofertilizer composition. In particular in those embodiments the C35 hopanoids are typically applied prior to applying the rhizobia to the seed.

In some embodiments applying the biofertilizer composition can be performed by coating and/or inoculating the leguminous seeds with the biofertilizer formulation prior to or at the time of planting. In some embodiments, applying the biofertilizer formulation can be performed by dipping the seedlings of the leguminous plants in a suspension comprising the biofertilizer. Alternatively or in addition, the biofertilizer formulation can be directly applied to soil where the seed is planted or to be planted.

In embodiments herein described, methods of fertilizing leguminous plants are described. The methods comprise administering the $C_{35}$ hopanoids, and rhizobia herein described and related biofertilizer composition to leguminous plants through seedling dipping, and/or direct-soil application, and/or seed treatment (also called seed inoculation), or other fertilizer application approaches identifiable by the skilled person.

In some embodiments, the methods of fertilizing leguminous plants comprise preparing a suspension containing one or more biofertilizer herein described and dipping the seedlings of the leguminous plants in the suspension for a certain time under a certain condition to allow the symbiotic interaction between the rhizobia, $C_{35}$ hopanoids and the leguminous plants.

In particular, a biofertilizer/inoculant suspension comprising $C_{35}$ hopanoids and $C_{35}$-hopanoids-producing nitrogen-fixing bacteria is prepared in water. The roots of seedlings are then dipped in the suspension and kept immersed for a certain period of time, typically several minutes, before being transplanted. Here, seedling refers to a young plant sporophyte developing out of a plant embryo from a seed. Seedling development starts with germination of the seed. A typical young seedling consists of three main parts: the radicle (embryonic root), the hypocotyl (embryonic shoot), and the cotyledons (seed leaves). For example, for soybean, each seedling can be treated with 1 ml of an $OD_{600}=1.0$ (~$10^9$ cells) suspension of bacteria in a nodulation medium that includes trace elements required by the nitrogenase cofactors to support nitrogen fixation.

In some embodiments, about ~1 billion cells can be suspended in a nodulation medium that contains $C_{35}$ hopanoids at a concentration below its critical micelle concentration (CMC).

The term "critical micelle concentration (CMC)" is used herein to characterize the aqueous solubility of a lipid compound such as $C_{35}$ hopanoids. CMC indicates the concentration above which amphiphilic molecules aggregate to form micelles. At low surfactant concentration the amphiphilic molecules arrange on the surface of the liquid, but also exist as free molecules in the solution, with the two groups exchanging with one another. As more amphiphilic molecules are added, the surface becomes saturated, and the concentration of free molecules in solutions approaches a concentration specific to the molecule and environment, at which point further addition of amphiphilic molecules will lead to formation of micelles. This concentration point above which micelles form is called the critical micelle concentration.

Many factors have effects on the CMC of a lipid compound as will be understood by a skilled person. For example, the molecular structure of the lipid, temperature, the presence of electrolyte in the solution and so on. Several empirical correlations can be used for the estimation of CMC values. For lipids with a straight and saturated single carbon tail, the CMC can be calculated from (Klevens 1953):

Log CMC=$A-Bn$ where n is the number of carbon atoms in the hydrophobic tail, and A and B are temperature dependent constants for a given type of lipid. The values of A and B are identifiable for a skilled person in the art. These constant values can also be found in textbooks such as Kreshech 1975 [29]. It is also possible to measure the CMC of a molecule with devices such as a contact angle system, a tensiometer, a Langmuir trough, or with other equipment identifiable by a skilled person.

In some embodiment, methods of fertilizing leguminous plants herein described comprise applying one or more biofertilizer and/or related biofertilizer composition herein described alone or in combination with the $C_{35}$ hopanoids directly to the soil where the leguminous plants are grown. In particular, the biofertilizer composition comprising a biofertilizer herein described, optionally in combination $C_{35}$ hopanoids and can be directly applied to the soil before or at the time of plantation or sowing.

For example, in some embodiments, the biofertilizer or biofertilizer composition can be firstly mixed with finely powdered farm yard manure (FYM), compost, or soil at a specific ratio and then directly applied to the soil. The formed mixture can be broad-cast at the time of plowing.

In some embodiments, methods of fertilizing leguminous plants comprise applying the $C_{35}$ hopanoids, $C_{35}$ hopanoid-producing rhizobia and related biofertilizer composition herein described via soil inoculation by placing the biofertilizer and related composition into the furrow under or alongside the seeds.

In particular, the biofertilizer and related compositions can further comprise a carrier material in granular form of a size about 0.5-1.5 mm. Suitable carrier material includes granular forms of peat, perlite, talcum powder, or materials that can offer nutrient and/or habitable micro-pore to the inoculants bacteria including carriers with micro-porous structure such as charcoal or soil aggregates.

In some embodiments, the methods of fertilizing leguminous plants comprise coating/inoculating the leguminous seeds with the $C_{35}$ hopanoids, $C_{35}$ hopanoid-producing rhizobia and related biofertilizer composition herein described, also referred to as seed treatment methods.

In particular, to prepare for inoculation, the biofertilizer can be firstly mixed with water to form a slurry mixture. The seeds desired to be treated are then immersed in the mixture for a certain period of time under certain conditions to form seeds coated or inoculated with the inoculum.

Leguminous plant seeds can be treated with the biofertilizer compositions comprising a carrier, $C_{35}$ hopanoids and $C_{35}$-hopanoids-producing nitrogen-fixing bacteria inoculant at a certain weight ratio identifiable to a skilled person in the art of agriculture and inoculation. In particular, the skilled person will recognize the relationship between seed size, number of $C_{35}$-hopanoids-producing nitrogen-fixing bacteria, the amount of $C_{35}$ hopanoids and weight of the inoculant. Similar to the seedling dipping method described above, about ~1 billion cells can be suspended in a nodulation medium that contains $C_{35}$ hopanoids at a concentration below its CMC.

In some embodiments, the vechicle used in the biofertilizer for seed treatment is in the form of fine powder with particle size of 10-40 µm. The carrier can be a material, such as peat, vermiculite, lignite powder, clay, talc, rice bran, seed, rock phosphate pellet, charcoal, soil, paddy straw compost, wheat bran or a mixture of such materials. In common practice, for better shelf-life of biofertilizer formulation, a carrier or a mixture of such carrier materials are selected based on the viability of the microorganisms mixed with them. The carriers used in the biofertilizer for seed inoculation are typically non-toxic to inoculant bacterial strains and plant, with certain moisture absorption and pH buffering capacity, easy to process and sterilize by autoclaving or gamma-irradiation and cost-effective. In some particular cases, to achieve a tight coating of inoculant on seed surface, adhesive material, such as gum Arabic, methylethylcellulose, sucrose solutions and vegetable oils, can be used as carrier. In some cases, supplementary nutrients and cell protectants such as sucrose, maltose, trehalose, molasses, glucose and glycerol can be used together with the carrier material to ensure improved cell viability and extended shelf-life.

In some embodiments, coated seeds comprising leguminous plant seeds coated with the biofertilizer formulation or inoculant are described. The coated seeds are prepared by coating or inoculating the seeds with the biofertilizer/inoculant according to the methods above described. The coated seeds can be prepared by manufactures and then distributed to farmers. Alternatively, the seeds can be coated or inoculated by farmers prior to planting. In particular, the seeds are leguminous seeds, including *Vicia faba, Arachis Hypogaea, Cicer arientum, Dolichos lablab, Lupinus albus, Pisum arvense, Glycine max, Cajanus cajan, Lens esculenta, Vigna radiate, Cyamopsis tetragonoloba, Vigna aconitifolius, Vicia hirsute, Trigonella foenum-graecum, Onobrychis sativa, Coronilla cretica, Ornithopus sativus, Desmodium intortum, Indigofera hirsute, Medicago sativa, Trifolium incarnatum, Lotus pedunculatus, Trifolium agrarium* and *Lotonois bainesii*. The biofertilizers formulation are carrier-based inoculants containing $C_{35}$ hopanoids, $C_{35}$-hopanoids-producing nitrogen-fixing bacteria and a carrier as described above.

In some embodiments, $C_{35}$ hopanoids have been shown to promote protection against numerous stresses, in particular, higher temperatures and acidic soil conditions. Consequently, the biofertilizer formulation comprising $C_{35}$-hopanoids and $C_{35}$-hopanoids-producing bacteria as described herein and the seeds inoculated with such biofertilizer can achieve improved viability of the microorganism used in such formulations prior to its release into the field as well as to survive under certain soil conditions (Examples 16-18).

In some embodiments, the biofertilizer and/or inoculated or coated seeds can be stored at ambient or higher temperatures between 22° C. and 37° C. More preferably, the storage condition includes a temperature of about 30° C. to about 35° C. In particular, in some embodiments, the biofertilizer and/or inoculated or coated seeds herein described can be stored at a temperature higher than 25° C., while still retaining a high viability rate, compared to other biofertilizer or inoculated/coated seeds comprising rhizobia incapable of producing $C_{35}$ hopanoids. In embodiments herein described, the biofertilizer and/or inoculated or coated seeds can be stored for long-term purpose in glycerol at −20° C. or below, after flash-freezing, or desiccation with improved bacterial survival rate and elongated storage time.

In some embodiments, the biofertilizer herein described and the seed coated with such biofertilizer can be planted under stress soil conditions such as high temperatures and low pH to effectively enhance plant growth and soil life. The stress soil condition includes a temperature of about 25° C. to about 37° C. and a pH value of about 6 to 8.

In some embodiments, the biofertilizer herein described comprises nitrogen-fixing rhizobia that can fix nitrogen outside plants, such as photosynthetic rhizobia including *Bradyrhizobium* BTAi1, Cyanobacteria and *Azotobacter* species. Rhizobia that can fix nitrogen outside plants comprise nif genes that are a set of genes encoding enzymes involved in the fixation of atmospheric nitrogen into a form of nitrogen available to living organisms. Such biofertilizer can be applied to oxygen-poor soils to enrich the soil nitrogen content. Exemplary rhizobia species that can be comprised in these biofertilizer include *Bradyrhizobium* BTAi1, *Bradyrhizobium* ORS285, *Bradyrhizobium* ORS278 and other rhizobia that can fix nitrogen in free-living conditions.

In some embodiments, the nitrogen-fixing rhizobia herein described are wild type bacteria that can naturally produce $C_{35}$ hopanoids. In other embodiments, the nitrogen-fixing bacteria herein described are nitrogen-fixing rhizobia that are naturally incapable of producing $C_{35}$ hopanoids (herein also $C_{35}$ hopanoid-deficient rhizobia) that are genetically modified to produce $C_{35}$ hopanoids (herein also genetically engineered C35 rhizobia). $C_{35}$ hopanoid-deficient rhizobia include rhizobia lacking of one or more $C_{35}$ hopanoids synthesis genes and capable of being mutated to include one or more $C_{35}$ hopanoids synthesis genes. Different from their wild type counterparts that cannot naturally produce $C_{35}$ hopanoids, genetically engineered C35 rhizobia are capable of producing $C_{35}$ hopanoids. The genetically engineered C35 rhizobia are expected to be more stress tolerant compared to their wild type counterparts.

Thus herein described are also one or more nitrogen-fixing genetically engineered $C_{35}$ rhizobia can be comprised in the biofertilizer described herein alone or in combination with $C_{35}$ hopanoids.

In some embodiments, the genetically engineered $C_{35}$ rhizobia comprise one or more bacteria closely genetically related to (within the same taxonomic order of) *Bradyrhizobia*, such as *Sinorhizobium meliloti* that are genetically modified to produce $C_{35}$ hopanoids. Additional exemplary legume $C_{35}$ bacteria mutants include mutants of, *Rhizobium leguminosarum, Mesorhizobium loti, Sinorhizobium meliloti, Azorhizobium caulinodans,* and *Ochrobactrum anthropi*.

General methods of preparing genetically engineered $C_{35}$ rhizobia are identifiable to a person of ordinary skill in the art upon reading of the present disclosure. In particular, preparing $C_{35}$ bacteria mutant can be achieved by introducing $C_{35}$ hopanoids synthesis genes (e.g. $C_{35}$ hopanoid gene cluster shown in FIG. 2, panel B) required for $C_{35}$ hopanoid synthesis into a rhizobia incapable of producing $C_{35}$ hopanoids, including the genes hpnP, shc, and hpnH, at physiologically relevant levels to result in a beneficial effect on plants affiliated with the bacteria, including legumes such as *A. afraspera* or soybeans or others.

This genetic modification can be achieved using various techniques identifiable by a skilled person including using gene expression constructs that direct expression of genes required for $C_{35}$ hopanoid synthesis, including suitable promoter, enhancer, and other elements required for expression in bacteria that would be recognized to perform this function by those of ordinary skill in the art. Methods for genetic modification can include modification of the bacteria by transfer of the genes using a recombinant plasmid, a recombinant non-viral vector, or a recombinant viral vector, encoding such gene expression constructs and additional methods identifiable by a skilled person.

In some embodiments, $C_{35}$ hopanoid synthesis genes can be obtained from "donor" rhizobium that naturally produces $C_{35}$ hopanoids, by using polymerase chain reaction (PCR)-based amplification and isolation of a region of genomic DNA encoding hopanoid synthesis genes and/or genomic regulatory elements, or cDNA encoding hopanoid synthesis genes (see Example 22). "Donor" genetic material used as a template for obtaining these genes and/or regulatory elements can be in the form of isolated genomic DNA, cDNA, or genetic material contained in previously-cloned plasmids. Sequences of donor material can be obtained from available gene databases and/or by sequencing the material using standard techniques. Using the DNA sequences in the donor material as a guide, design of appropriate primers, PCR reagents and methods can be achieved by a person of ordinary skill in the art.

In some embodiments, after the $C_{35}$ hopanoid synthesis genes and/or other regulatory elements are obtained, incorporation of the genes and/or other regulatory elements into a plasmid vector or other vector can be achieved using standard molecular cloning techniques. For example, the $C_{35}$ hopanoid synthesis genes can be excised from surrounding genetic material by restriction endonuclease digestion to provide a $C_{35}$ hopanoid synthesis gene "insert". In parallel, restriction endonuclease digestion can be performed on a plasmid vector or other vector into which the $C_{35}$ hopanoid genes are inserted. DNA ligation can then be performed to result in a plasmid containing the $C_{35}$ hopanoid synthesis genes and/or regulatory sequences.

In some embodiments, the vector containing the $C_{35}$ hopanoid synthesis genes can contain appropriate regulatory elements to express the $C_{35}$ hopanoid synthesis genes, including but not limited to promoters, enhancers, 5' and 3' untranslated regions, exons, introns, enzyme recognition sites for appropriate processing of transcripts, and post-transcriptional and post-translational genetic elements. Exemplary regulatory elements that can be comprised in the vector can comprise elements that are naturally associated with the $C_{35}$ hopanoid synthesis genes in genomic DNA of the "donor" genetic material, and/or elements comprised of "heterologous" elements that are not normally associated with the natural $C_{35}$ hopanoid synthesis genes, such as promoters normally associated with other genes.

In some embodiments, vectors used to introduce $C_{35}$ hopanoids synthesis genes can include in addition to elements for regulating expression of $C_{35}$ hopanoid synthesis genes, other genetic material comprising other regulatory sequences, including origin of replication, genes for expressing antibiotic resistance, and restriction endonuclease sites.

In some embodiments, vectors used to introduce $C_{35}$ hopanoids synthesis genes comprise a plasmid vector containing an expression cassette for a single hopanoid synthesis gene. In other embodiments, vectors used to introduce $C_{35}$ hopanoids synthesis genes comprise a plasmid vector containing expression cassettes for more than one hopanoid synthesis gene. In some embodiments, a recipient rhizobium can be genetically modified with one or more plasmid vectors containing one or more hopanoid synthesis gene expression cassettes, as required to provide a full set of hopanoid synthesis genes.

In some embodiments, vectors containing hopanoid synthesis genes can be introduced into bacteria, including rhizobia, by a process of transformation, whereby the bacterial cell wall is transiently opened allowing entry of the plasmid DNA into the bacterium. Several methods of transformation can be used, including electroporation, thermal shock, freeze-thaw techniques (see Examples 25-27).

In some embodiments, transfer of vectors and in particular plasmid vectors containing $C_{35}$ hopanoid synthesis genes into rhizobia can be performed by a process of conjugation, in which plasmid DNA is transferred from an E. coli bacterial cell into a rhizobium by direct contact (see Example 23).

In some embodiments, gene expression cassettes required for genetically modifying a rhizobium to produce $C_{35}$ hopanoids are maintained on an plasmid, rather than integrating into bacterial host DNA. In other embodiments, gene expression cassettes required for genetically modifying a rhizobium to produce $C_{35}$ hopanoids are integrated into host rhizobial DNA. In some embodiments, integration into rhizobial DNA is at a symbiotically-silent locus in the genome. A person of ordinary skill in the art will be able to identify appropriate plasmid vectors available that containing elements to either maintain a $C_{35}$ hopanoid gene expression cassette in a plasmid, or that contain elements that enable integration into a host bacterial genome, including containing DNA sequences that enable homologous recombination into host bacteria DNA, or non-homologous end-joining of gene expression cassette DNA into host bacteria DNA.

In some embodiments, introduction of $C_{35}$ hopanoid synthesis genes into $C_{35}$ hopanoid-deficient rhizobia to produce $C_{35}$ rhizobia mutants can be performed by transduction using a recombinant viral vector containing a $C_{35}$ hopanoid synthesis gene expression construct In some embodiments, vectors containing hopanoid synthesis genes can be introduced into bacteria, including rhizobia, by a process of transformation, whereby the bacterial cell wall is transiently opened allowing entry of the plasmid DNA into the bacterium. Several methods of transformation can be used, including electroporation, thermal shock, freeze-thaw techniques (see Examples 25-27).

In some embodiments, transfer of vectors and in particular plasmide vectors containing $C_{35}$ hopanoid synthesis genes into rhizobia can be performed by a process of conjugation, in which plasmid DNA is transferred from an E. coli bacterial cell into a rhizobium by direct contact (see Example 23).

In some embodiments, introduction of $C_{35}$ hopanoid synthesis genes into $C_{35}$ hopanoid-deficient rhizobia to produce genetically engineered C35 rhizobia can be performed by transduction using a recombinant viral vector containing a $C_{35}$ hopanoid synthesis gene expression construct Additional techniques and related vectors methods and systems to modify a nitrogen fixing rhizobia incapable of producing $C_{35}$ are identifiable by a skilled person.

Nitrogen fixing rhizobia capable of producing $C_{35}$ naturally or after genetic modifications as herein described can be identified by screening methods performed on one or more candidate rhizobia strains for their ability to produce of $C_{35}$ hopanoids.

In some embodiments, one or more candidate rhizobia strains can be screened by a method of screening stress-resistant rhizobia comprising providing the one or more candidate rhizobia strains; and detecting in the one or more candidate rhizobia strains, production of a $C_{35}$ hopanoid and/or $C_{35}$ hopanoids synthesis genes to identify stress-resistant rhizobia.

Detection of $C_{35}$ hopanoid can be performed by directly detecting the $C_{35}$ hopanoid and/or molecules involved in the related biosynthetic pathway including squalene, diploptene, adenosyl hopane, ribosyl hopane, formyl hopane, other hopanoid intermediates and $C_{35}$ precursors as shown in Welander 2009 and Welander 2012 and identifiable to a skilled person in the art.

In particular, in some embodiments, a method of screening stress-resistant rhizobia strains can comprise providing a plurality of rhizobia strains, culturing the cells of each rhizobia strain, analyzing lipids extracted for presence of $C_{35}$ hopanoids, and selecting the rhizobia strain producing $C_{35}$ hopanoids as stress-resistant rhizobia.

For example, screening rhizobia for the ability to produce $C_{35}$ hopanoids can be performed by analysis of lipids extracted from samples of rhizobia obtained from soil, legume nodules, or other sources. In particular, the analysis can be performed by culturing the rhizobia, extracting the lipid content from the cultured cells, and purifying the lipid extract and performing analytical chemistry techniques to detect the $C_{35}$ hopanoids (including gas chromatography-mass spectrometry and liquid chromatography-mass spectrometry) (see Example 29).

In some embodiments, detection of $C_{35}$ hopanoid can be performed in addition or in the alternative by detecting one or more $C_{35}$ hopanoids synthesis genes. Detection of $C_{35}$ hopanoids synthesis genes can be performed by DNA sequencing, PCR probes and/or other nucleotide amplification techniques as will be understood by a skilled person.

For example, in some embodiments, a method of screening stress-resistant rhizobia strains as biofertilizer can comprise genetically screening rhizobia strains capable of producing C35 hopanoids. In those embodiments, the method can comprise providing a plurality of rhizobia strains, for each rhizobia strain detecting $C_{35}$ hopanoid synthesis genes (e.g. by conducting a diagnostic polymerase chain reaction or DNA sequencing methods) in the rhizobia strain, and selecting the rhizobia strain with detected $C_{35}$ hopanoid synthesis genes.

In method for genetic screening of rhizobia, detected presence of $C_{35}$ hopanoid synthesis genes can be used as a marker for the ability of particular rhizobia to produce $C_{35}$ hopanoids (see Example 30). In some embodiments, detecting Diagnostic PCR or DNA sequencing on genomic DNA isolated from rhizobia obtained from soil, legume nodules, or other sources can be performed to determine whether $C_{35}$ hopanoid synthesis genes are present in a particular sample rhizobial genome. Using available gene sequence information, PCR primers can be designed to amplify genes in the hopanoid synthesis gene cluster, whereby amplification of genes necessary for $C_{35}$ hopanoid synthesis indicates a rhizobial species genetically capable of producing $C_{35}$ hopanoids. Similarly, DNA sequencing may be used to determine whether $C_{35}$ hopanoid synthesis genes are present in the genome of a sample rhizobium, and therefore whether the rhizobium is genetically equipped to synthesize $C_{35}$ hopanoids.

Additional techniques for detecting $C_{35}$ hopanoids and/or $C_{35}$ hopanoids synthesis genes are identifiable by a skilled person.

In some embodiments, biofertilizers, biofertilizer compositions, seed and methods herein described can comprise at least one nitrogen fixing bacteria other than a rhizobia (e.g. ar rhizobiales) which is symbiotic with legumes, is incapable of producing $C_{35}$ hopanoids ($C_{35}$ deficient), and is closely genetically related to (i.e. within a same taxonomic order of) hopanoids-producing legume rhizobia symbiont capable of producing $C_{35}$ hopanoids. In those embodiments the at least one nitrogen fixing bacteria other than a rhizobia can be genetically engineered to include shc, hpnH and hpnG, hpnO, as well as hpnP, hpnC, hpnD and/or hpnE and provide a genetically engineered C35 bacteria that can be used in fertilizers, biofertilizer compositions, seed and methods herein described.

The biofertilizer, biofertilizer composition, seeds, genetically engineered $C_{35}$ rhizobia and $C_{35}$ hopanoids herein described can be provided as a part of systems to fertilize leguminous plants or soil with suitable methods, including any of the methods described herein. The systems can be provided in the form of kits of parts. In a kit of parts, the biofertilizer, biofertilizer composition, seeds and $C_{35}$ hopanoids and other reagents to perform fertilization of the leguminous plant or soil can be comprised in the kit independently. The biofertilizer, biofertilizer composition, seeds and C35 hopanoids can be included in one or more compositions, and nitrogen fixing rhizobia capable of producing $C_{35}$ hopanoids can be in a composition together with a suitable vehicle.

In particular, the components of the kit can be provided, with suitable instructions and other necessary reagents, in order to perform the methods here described. The kit will normally contain the compositions in separate containers. Instructions, for example written or audio instructions, on paper or electronic support such as tapes or CD-ROMs, for carrying out the assay, will usually be included in the kit. The kit can also contain, depending on the particular method used, other packaged reagents and materials such as buffers and the like.

Further details concerning biofertilizers, and related seeds compositions methods and system, cells and formulation of the present disclosure will become more apparent hereinafter from the following detailed disclosure of examples by way of illustration only with reference to an experimental section.

EXAMPLES

The hopanoids, hopanoids-producing nitrogen-fixing bacteria, and related formulation and methods herein described are further illustrated in the following examples, which are provided by way of illustration and are not intended to be limiting.

In particular, the following examples illustrate exemplary hopanoids, hopanoids-producing nitrogen-fixing bacteria forming symbiosis with exemplary leguminous plants and related methods and systems. In particular, in the examples described herein, *B. diazoefficiens* is used as a model strain to study the roles of two hopanoid classes, 2Me-hopanoids and $C_{35}$ hopanoids, in symbiosis with leguminous plants such as *Aeschynomene afraspera* and soybean.

A person skilled in the art will appreciate the applicability and the necessary modifications to adapt the features described in detail in the present section, to additional hopanoids-producing nitrogen-fixing bacteria, such as other related *Bradyrhizobium* bacteria as described in the above disclosure capable of forming symbiosis with leguminous plants, and related methods and systems according to embodiments of the present disclosure.

Example 1: Hopanoids from *B. diazoefficiens*

Figure 2:
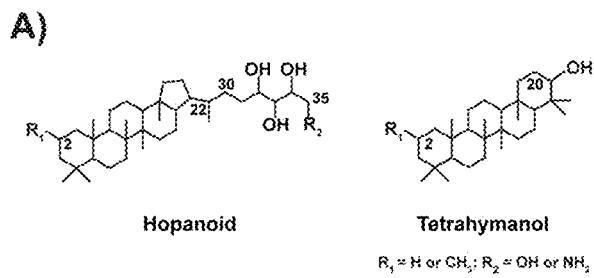
FIG. 2 shows, in panel A, exemplary structures of a $C_{35}$ hopanoid and tetrahymanol. *B. diazoefficiens* makes $C_{30}$ hopanoids like diploptene (C-22=C-30) and diplopterol (OH at C-22); $C_{35}$ hopanoids like bacteriohopanetetrol (BHT, $R_2$=OH) and amino-bacteriohopanetriol (aminotriol, $R_2$=NH$_2$); and tetrahymanol. All these compounds can be methylated at C-2 (2Me, $R_1$=CH$_3$). Panel B shows the hopanoid biosynthetic gene cluster of *B. diazoefficiens*. In this study, we focused on the genes colored in gray: shc (squalene hopene cyclase) catalyzes squalene cyclization to hopene, the first reaction in the hopanoid biosynthetic pathway; hpnH catalyzes addition of adenosine to hopene, the first reaction in the synthesis of $C_{35}$ hopanoids; and hpnP catalyzes C-2 methylation. Panel C shows GC-MS and LC-MS (inset) total ion chromatograms of total lipid extracts from aerobically grown *B. diazoefficiens* strains. GC-MS: Main hopanoid peaks are numbered and the methylated counterparts elute 0.2-0.5 min earlier: I, pregnane acetate (standard); II, (2Me) hop-17(21)-ene; III, (2Me) hop-x-ene; IV, (2Me) hop-22(29)-ene (diploptene); V, (2Me) hop-21-ene, VI, (2Me) hopan-22-ol (diplopterol); VII, (2Me and 20Me) tetrahymanol; and VIII, BHP-508. LC-MS: a, aminotriol; b, BHT; c, 2Me-aminotriol; d, adenosylhopane; and e, 2Me-BHT. Lipid analysis for each strain was performed in triplicates. For chemical structures of hopanoids, refer to FIG. 1, panel A.
Figure 2:
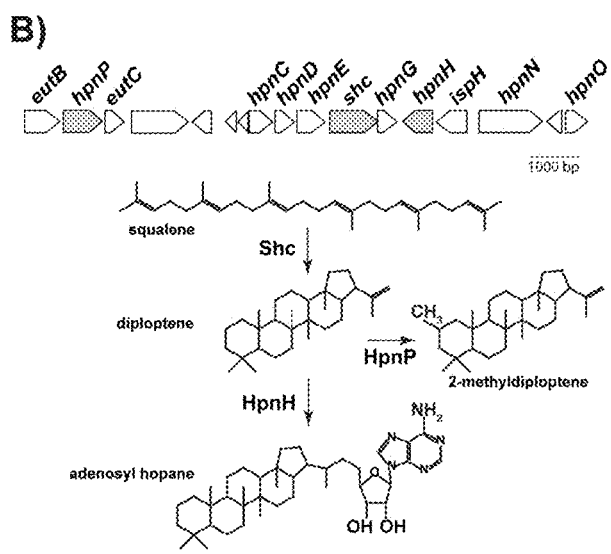
Figure 2:
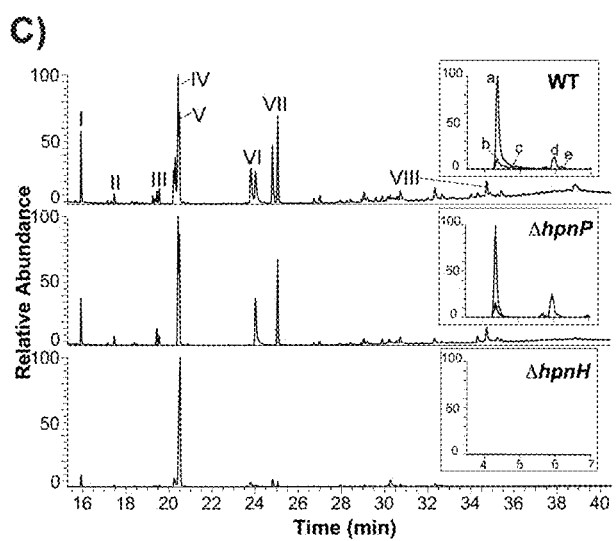

FIG. 1, panel A shows exemplary chemical structures of isolated hopanoids from *B. diazoefficiens*. While most hopanoids are thought to occur free within membranes, the $C_{35}$ hopanoid, (2-Me) 34-carboxyl-bacteriohopane-32,33-diol, was found to be covalently attached to LPS lipid A in the outer leaflet of the outer membrane (OM), a well-established player in a broad range of host-microbe interactions, to form a compound called Hopanoid-Lipid A (HoLA) [7, 30] (FIG. 1, panel B). As seen in the expanded view of the OM, *B. diazoefficiens* makes short ($C_m$) hopanoids like diploptene and extended ($C_{35}$) hopanoids like bacteriohopanetetrol (BHT) and aminotriol. Penta- and hexa-acylated Lipid A contain 5 and 6 fatty acyl chains, respectively. Hepta-acylated Lipid A contains the $C_{35}$ hopanoid, 34-carboxyl-bacteriohopane-32,33-diol, covalently attached to hexa-acylated Lipid A. In addition to $C_{30}$ and $C_{35}$ hopanoids [5], *B. diazoefficiens* makes tetrahymanol, a triterpenoid with a gammacerane skeleton [31] (FIGS. 1 and 2, panel A).

Example 2: Synthesis of Hopanoids from *B. diazoefficiens*

$C_{35}$ hopanoids are biosynthesized by a hopanoid biosynthetic gene cluster in some bacteria. For example, in *B. diazoefficiens*, $C_{35}$ hopanoids can be synthesized by a hopanoid biosynthetic gene cluster shown in FIG. 2, Panel C. In particular, shc (squalene hopene cyclase) catalyzes squalene cyclization to hopene, the first reaction in the hopanoid biosynthetic pathway; hpnH catalyzes addition of adenosine to hopene, the first reaction in the synthesis of $C_{35}$ hopanoids; and hpnP catalyzes C-2 methylation. Detailed description of the biosynthetic pathway and involved genes can be found in Welander 2012 [12].

Table 2 lists the $C_{35}$ hopanoid biosynthesis genes and their sequences from *R. palustris*.

TABLE 2

DNA sequences of *R. palustris* hopanoid biosynthesis genes

| Gene Name | DNA sequence | SEQ ID NO |
|---|---|---|
| hpnC | ATGACGTCTGCGAGCGAGCTTCGATCGGGCAAGACCCACCGGGACGAGAATTTC CCGGTCGCGTCGTGGATCATCCATCCGCGGCATCGCGACCTGATTCTGGCGTTCT ACAATTTCGTCCGGACCGCGGACGACATCGCCGATCACGAGATGCTCGATGGCG ACACCAAGCTCGAATATCTCGATCTGCTCGAAGCCGAGCTGCTCGGCCGCGGCG AGACCCAGCCCGAGGCGGTGCATCTGCGTCGGGCGCTGGCCGAACGCGGCATGC CGCCGCGCCATGCGCTCGATCTGCTGACCGCGTTTCGGATGGACGTCACCAAGCT GCGCTACGAGGATTGGGACGAGGTCATTCACTACTGCCGCTACTCGGCGATGCCG GTTGGCCGCTTCATGCTCGACGTCCACGGCGAAAGCACCACGACCTGGCAGGCCT CCGACGCGCTGTGCGCGGGGCTTCAGATCAACAATCACCTGCAGGACTGCGGCA AGGACTATCGCACCCTCAATCGCGTGTATCTGCCCACGCGACGTGCTCGATGCCGC CGGCCGCCAAGGTCGAAGACCTCGGCCTGCAGAAGTCGTCACCGGCGCTGCTGAA ATGCCTGCAGGGTCTTGCGGTCCGCACCGCGTCGCTGCTCGGCGACGGCCGGCCG CTCGCCGCCGAGATCAAGGATTATCGCCTCGGTCTCGAAGTCTCGGTGATCCAGG CCTATGCCGATCGCATCGTGCGGATGCTGCAGACCCGCGATCCGCTCAGCGAGCG CGTGCATCTGAAGCCGATCGAATTCGTGATCGCCAGCTTCGGCGCGATGAGTTCG GAGATCGTCCGTCGTAGCTTCGGAAAGGGGCCGGTGTCGCATCCGGCGCCGCGC GCATGA | 25 |
| hpnD | ATGACCGTTCACGCCACGCCAGAGCCGGCCGCACATCAAGGTGTCGCGCTCGGC AGTTCGTTCTACGCCGCGATGCGCATCCTGCCGCGTCCGCAGCGCGAGGCGATGT TCCAGGTCTACAGCTTCTGCCGCTTCGTCGACGACATCGCCGATTCCGATCGGCC GCGCGAGCAGCGGGTCGCCGAGCTGCAGCAATGGCGCGACGACATCGCCGCGCT GTATCGCGGTGCGCCGCCGCCGCGGCTCGCCGACTATCAGGAGTCGCTGCGCACT TTCGGGCTGAAGCGCGAGGACTTCGAGGCGATCATCGACGGCATGGAGATGGAT GTCGACGCCGACATCCGCGCGCCCGATGAGGCCACGCTCGATCTGTACTGCGACC GCGTCGCCAGCGCGGTGGGACGGCTGTCGGTGCGGATCTTCGGCCTTCCGGAAG CCGACGGCATCGAGCTGTCGCATCATCTCGGACGCGCGCTGCAGCTCACCAACAT CCTGCGCGACATCGACGAGGACACCGGCATCGGCCGGCTGTATCTGCCGAGCGA GCTGCTGCACAAGGTCGGTATCACCGCAACCGATCCGCGCGTGGTCGCGGCGGA TTCTGCGCTGCCGAGCGTCTGCGCGCCGCTGGTCGAGCGTGCGCTCGCGCATTTT GCCGCCGCCGACAAGGTGATGAACCGTAATCCGCGCCGGGTGGTGAAAGCTCCC CGTATCATGGGCAAGTACTACTACTCGATCTTGCAGCTTTTGATCGCGCGCGGTT TCGCAGCGCCGCGCGCCCCGGTGAAGCTCGGCAAGGCTTCGAAGATCGCCATCC TGCTGCAATACGCGATCGTGTGA | 26 |
| hpnE | ATGTCGAAAACAGTTCACGTCATTGGTGCGGGAATCTCCGGGCTTGCGGCCGCGA TCCGGCTCGCCCGCGCCGGCCTCACCGTCCATGTTCACGAAGCGATGCAGCAGGC CGGTGGCCGCTGCCGCTCGTATTTCGACGCCCAGACCGGGCTTGTCATCGACAAC GGCAATCACCTGCTGCTGTCGGGTAATCACGCCGCCTGCGACTACGCGCGGACG ATCGGCACCGAGGCGGGCCTCGTCGGCCCGGAGCGCGCCGAGTTCGACTTCATC GATCTGCCGGCTAATGCGCGCTGGCGGCTGAAGCTCGGCGGCGGCAAGCTGCCG CTGTGGCTGTTTGATGCCAATAGCCGCGTGCCGGACACGTCGATCGGCGATTACC TCGGCTTGATGCCGCTGCTGTGGGCGCCGACCACCAAACTGATCGGCGACACCAT CAACTGCTCCGGCCCGCTGTACGACCGCTTGGTGGCGCCGCTGCTGCTCGCCGCG CTCAACGTCGATCCGCCGGAAGGCTCGGCCGGGCTTGCCGGCGCGGTGGTTCGTG AGACGCTGCTGGCCGGCGGCAAGGCCTGCCGGCCGCTGATCGCCCGCGATGGCC TGTCGGCGGTGCTGGTCGAGCCGGCCGTGGCGCAGCTCGCCGCCCGGTCCAG GAGTGCAGTTCGGCCACGAGCTGCGGGCGCTGACCCCGGCCGGCGACCGCGTCG GCGCGCTGCAGTTCGGCGGTGAGGATGTCGTCACCCTCGGGCCGGATGATGCGG TGGTGCTGGCGGTGCCGCCGCGCCCGGCCGCTTCGCTGCTGCCCGGGCTGAAGAC GCCACAGGAATACCGCGCGATC GTGAACGCGCACTTCAATTACGCGCCGCCGCCTGGCATGCCGGCCCTGACCGGG GTGATCGGCGGGTGGTGGAGTGGCTGTTCGCGTTCCCGAACCGGCTGTCCGTGA CGATCAGCAACGGCGACCGGCTGGTGGACGCCCCGCGCGAGCAGCTTGCGGCCG AAATTTGGGGCGAAATCTGTAAATTGCGGGGATCTCGGCCAATCTGCCGCCGTG GCAAATTGTCCGCGAGCGCCGCGCCACGTTCGCCGCTACACCGGCGCAGAACGC CCTGCGCCCCGGGCCGGTCACCCAGTGGAGAAACCTATATCTCGCAGGCGATTG GACTGATACGGGGTTACCGGCGACCATCGAGGGATCGGTCCGGTCCGGCAACCG TGCCGCGGACCTGGTGCTGGCCGCTGGCCGCGCCTGA | 27 |

TABLE 2-continued

DNA sequences of R. palustris hopanoid biosynthesis genes

| Gene Name | DNA sequence | SEQ ID NO |
|---|---|---|
| hpnF | ATGGATTCCGGCAGCTACACGACTGGTGTGGAGCGCAACGCGCTCGAAGCTTCG<br>ATCGATGCGGCGCGCAGCGCGCTGCTGAATTATCGTCGCGACGATGGCCATTGG<br>GTGTTCGAACTCGAGGCCGATTGCACCATTCCTGCCGAATACGTGCTGCTGCGGC<br>ATTACCTCGGCGAGCCGGTCGATGCCGAGCTCGAAGCCAAGATCGCGGTTTATCT<br>GCGCCGCATCCAGGGTGCCCATGGCGGCTGGCCGCTGGTGCACGACGGCGACTT<br>CGACATGAGCGCCAGCGTGAAGGGTTACTTCGCGCTGAAGATGATCGGCGACAG<br>CATCGATGCCCCGCATATGGTGCGGGCGCGCGAGGCGATCCGTTCGCGCGGCGG<br>CGCGATCCACTCCAACGTCTTCACCCGGTTTCTGCTCACGTTGTACGGCGTTACG<br>ACCTGGCGCGCGGTTCCGGTACTGCCGGTCGAGATCATGCTGCTGCCGAGCTGGT<br>CGCCGTTCACACTGACCAAGATCTCGTATTGGGCGCGTACCACGATGGTGCCGCT<br>GCTCGTGCTGTGCGCGCTGAAGCCGCAGGCCAAGAATCCGAAGGGCGTCGGCAT<br>CGACGAACTATTCCTTCAGGACCCGAAGACGATCGGGATGCCGGTCAAGGCGCC<br>GCATCAGAACTGGGCGCTGTTCAAGCTGTTCGGATCGATCGACGCGGTGCTGCGC<br>GTGATCGAGCCTGTGATGCCCAAAGGCATCCGCAAGCGCGCGATCGACAAGGCG<br>CTCGCCTTCATCGAGGAGCGGCTCAACGGCGAGGACGGCATGGGCGCGATCTTC<br>CCGCCGATGGCCAACGCCGTGATGATGTACGAGGCGCTCGGCTATCCCGAGGAC<br>TATCCGCCGCGCGCCAGCCAGCGCCGCGGCATTGATCTCTTGCTGGTCGATCGCG<br>GCGACGAAGCCTACTGCCAGCCCTGCGTGTCGCGGTGTGGGACACCGCGCTCG<br>CCAGCCATGCGGTGCTCGAGGCGGACGGTCACGAGGGCGCCAAGTCGGTGCGGC<br>CGGCGCTCGACTGGCTGCTCCCGCGCCAGGTGCTCGACGTCAAGGGCGACTGGG<br>CCGTCAAGGCCCCGAACGTCCGCCCCGGCGGCTGGGCGTTCCAGTACAACAACG<br>CCCACTATCCGGATCTCGACGATACCGCGGTGGTGGTGATGGCGCTCGACCGCGC<br>CCGCAAGGACCAGCCGAATCCCGCCTACGATGCCGCGATTGCCCGCGCCCGCGA<br>GTGGATCGAGGGGATGCAGAGCGACGATGGCGGCTGGGGTGCCTTCGACATCAA<br>CAACACTGAGTATTATTTGAACAACATCCCGTTCTCGGACCATGGCGCGATGCTC<br>GATCCGCCGACCGAGGACGTCACCGCGCGCTGCGTCTCGATGCTGGCTCAGCTCG<br>GTGAGACCATGGACAGCAGCCCGGCGCTGGCCCGCCGTCGGCTATCTGCGCG<br>ACACCCAGCTCGCCGAGGGCTCCTGGTACGGCCGCTGGGGCATGAATTACATCTA<br>CGGCACCTGGTCGGTGCTGTGCGCCCTCAACGCCGCCGGCGTTCCCCATGCCGAT<br>CCGATGATCCGCAAGGCGGTCGCCTGGCTGGAGTCGGTGCAGAATCGCGACGGC<br>GGCTGGGGCGAGGACGCGGTCAGCTACCGACTGGATTACCGCGGCTACGAAAGT<br>GCACCTTCGACCGCCTCTCAGACGGCATGGGCTTTGCTTGCTCTGATGGCTGCGG<br>GTGAGGTCGATCATCCCGCCGTGGCACGGGGCATCGAGTACCTGAAAAGCACAC<br>AGACCGAAAAGGACTGTGGGACGAGCAGCGTTACACGGCGACGGGCTTCCCGC<br>GGGTGTTTTATCTGCGGTATCATGGCTATTCGAAGTTCTTCCCACTCTGGGCGCTC<br>GCCCGGTATCGGAACTTGCAGGCCACGAACAGCAAGGTGGTAGGGGTCGGAATG<br>TGA | 28 |
| hpnG | GTGATTCTGGGGGCAGTGGACGACCAGGCCGCGGCGCTTCGCCAAGATCCGCGG<br>CCGGTACTGATTGTGACGGGCCTGATTCAGGAAGCACGTATCGCGCGGATCATGG<br>GGCCTCACCGTTATCTGCAGCAGCAGTGACCCCAAGCAATTGCGCGCGATCATGG<br>CCGACTTCGACGCATCGTCGATCCGGGGCGTGATCAGCTTCGGCGTCGCCGGGGG<br>GCTGGATCCCTCTCTCGAGGCAGGTGACATCGTCATCGCCACCGAGGTTGTGCCG<br>GGTGAACGCCGCTGGACGTCGGAAGTTGCACTGACCGACGAATTATTGCGAAGC<br>GCCGGGCTCGGCCGTCAGCGCGTCGTGCGCGGCGGTCTGGTCGGCGCCGAGCAG<br>GTGATCGCAGCGCGCTCCGCCAAGGCGGCGCTGCGCTCGGAGACCGGTGCGGCT<br>GCGGTCGATATGGAAAGCCACATCGCCGCCGATTTCGCCGCCGCCGCCAAGCTG<br>CCGTTCGCGGCGCTCCGGGTGATCAGCGATCCGGCGAATCGCAGCCTGCCGCAG<br>ATCGTGTCGAGCGCGATCAAGCCGAACGGCGATATCGACCTGCGCAAGGTGCTG<br>CGCGGCATCGCCCGTCACCCGACCTCGATCCGCTCGCTGGTGTCGACCGGCATCG<br>ACTTCAACCGCGCGCTGCGCTCCCTGCGCGGCTGTCGGAACTTTGTGCAGGACGC<br>CGTGCTCGGCCGCGGCGGTCTCGTCGCCGAGATCTGA | 29 |
| hpnH | ATGGCTATTCCGTTTCACAAGGAACTGGTGATCGGCGGTTATCTGCTGAAGCAGA<br>AGCTGCTCGGGCGGAAGCGTTATCCGCTGGTACTGATGCTGGAGCCGCTGTTCCG<br>CTGTAACCTCGCCTGCGCCGGCTGCGGCAAGATCGACTATCCGCACGCGATCCTG<br>AACCGCCGGATGACCGCACAAGAGTGCTGGGACGCCGCCGAGGAATGCGGCGCG<br>CCGATGGTTGCGATCCCGGGCGGCGAACCGCTGATCCACAAGGAGATCGGCGAG<br>ATCGTGCGCGGCCTGGTGGCGCGCAAGAAGTTCGTGTCGCTGTGCACCAACGCG<br>CTGCTGCTCGAGAAGAAGCTGCATCTGTTCGAGCCGTCGCCCTACCTGTTCTTCTC<br>GGTGCATCTCGACGGCCTGAAGGAGCACCACGACAAGGCGGTGTCGCAGCAGGG<br>CGTGTTCGACCGCGCAGTCGCGGCGATCAAGGCCGCCAAGGCCAAGGGCTTCAC<br>CGTCAACGTCAACTGCAGGTGTTCGACGGCTACGCCGCCGAAGACATCGCCAA<br>GTTCATGGACTTCACCGAGGAACTCGGCGTCGGCGTCTCGATCTCGCCGGGCTAC<br>GCCTATGAGCGCGCTCCGGACCAGGAGCACTTCCTCAACCGCACCAAGACCAAG<br>AACCTGTTCCGCGAGGTGTTCGCGCGCGGCAAGGGCAAGAAGTTGGAGCTTCATG<br>CACTCCAGCATGTTCCTCGACTTCCTGGCCGGCAATCAGGAGTTCGAGTGCACGC<br>CGTGGGGTATGCCGGCGCGCAACATTTCGGCTGGCAGAAGCCCTGCTACCTGCT<br>CGGCGAAGGCTACGCCAAGACTTTCCAGGAGCTGATGAAACCACCGATTGGGA<br>TTCCTACGGCACCGGCAAGTACGAGAAGTGCGCCGACTGCATGGCGCATTGCGG<br>CTACGAACCGACCGCGGCGATGCCTCTCTCAACAATCCGCTGAAGGCGCCTG<br>GGTGGCGCTCCGCGGCATCAAGACCTCGGGCCCGATGGCGCCGGAGATCGACAT | 30 |

TABLE 2-continued

DNA sequences of *R. palustris* hopanoid biosynthesis genes

| Gene Name | DNA sequence | SEQ ID NO |
|---|---|---|
| | GTCGAAGCAGCGCCCGGCGCAGTACGTGTTCTCCGAGCAGGTCCAGAAGACGCT<br>GACGCAGATCCGCCAGGACGAGGCCGCCGAGGCCAAGGACAAGCGGCAGGCGG<br>AAAGGTCGACGGCGGCCTGA | |
| hpnN | GTGCTGAAAAGTGCCATCGTCTCCATTGTCAGAGCCAGCACCCGTTTTGCGGCTT<br>TTACTGTGCTGATCGGCGTATTTCTCGCAGTTGCAGCAGGTTTCTATACTTACCAA<br>CATTTCGGGATCAACACAGACATCAATCATTTGATCTCGTCTGATCTCGACTGGC<br>GCAAACGTGATATCGCGTTCGAGAAGGCATTCGACCAGGAACGGCTGATCCTGG<br>CCGTCGTCGAGGCCCCGACGCCGGAATTCGCCAATGCCGCGGCGGCCAAGCTCA<br>CGGCCGAATTGTCCAAGAATAACATCAACTTCGACTCGGTGAAGCGGCTCGGCG<br>GCGGGCCGTTTTTCGACCGCAGCGGGCTGCTGTTCCTGCCCAAGGACGAGGTCGC<br>CAAGGCCACCGGCCAGTTCCAGCAGGCGGTTCCCCTGATCGAGATCATGGCCGG<br>CGATCCGTCGATCCGCGGCCTGACGGCGGCACTCGAGACCGGTCTGGTCGGGTTG<br>AAACGCGGGGAACTGACCCTCGACGCCACCGCGAAACCTTTCAATACAGTCGCC<br>GCGACCGTCGAGGACGTGCTCGGCAAGCAGCAGGCGTTCTTCTCCTGGCGCGGC<br>CTGGTCAATCCGGAACCGCTGACCGATGGCGACAAGCGCGCCTTCATCGAGGTC<br>AAGCCGATCCTCGACTTCAAGGCGCTCGAACCCGGCAAGGCGGCGACCGACGCG<br>ATCCGTCAGGCGGCAGTCGATCTCAAGATCGAGCAGGATTTCGGCGCCCGGGTG<br>CGGCTGACCGGCCCGGTGCCGATCGCCAACGAGGAATTCGCTACCGTTAAGGAC<br>GGCGCCGTGGTCAACGGCATCGGGACCGTCGTGGTGGTGCTGCTGATCCTCTGGA<br>TGGCGCTGCATTCCTCCAAGATCATCTTCGCGGTGGCGGCCAATCTGGTGATCGG<br>CCTGTCGATCACCACCGCGGTCGGCCTGATGCTGGTGGATTCGCTCAACCTGCTG<br>TCGATCGCGTTCGCGGTGCTGTTCGTCGGCCTCGGCGTCGATTTCGGCATCCAATT<br>CAGCGTCCGCTATCGATCGGAACGCCACAAGACCGGGGACCTCGAGAAGGCCCT<br>GGTCCAGGCCGCCGAATACTCCGCGGTGCCGCTGTCACTGGCGGCGATGTCGACC<br>ACGGCCGGCTTCCTGTCGTTCCTGCCGACGTCCTACAAAGGCATTTCCGAACTCG<br>GCGAGATCGCCGGTGCCGGCATGGCGATCGCGTTCTTCACCAGCATCACCGTGCT<br>GCCGGCGCTGCTGAAGCTGCTGAACCCGGCGGGTGAGAAGGAACCGCTTGGCTA<br>CGCCTTCCTGGCGCCGGTCGATCACTTCCTGGAGAAGCACCGCATCGCCATCATC<br>GTCGGCACGATCGGTGTCGCGCTGGCCGGCCTGCCACTGCTGTACTTCATGCATT<br>TCGACTTCAACCCGATCAATCTGCGCAGCCCGAAGGTCGAGTCGATCGCGACGTT<br>CCTTGACCTGCGCAAGGATCCGAATACCGGTGCCAACGCCGTCAACGTGATGGC<br>GCCGAACGAGCAGGCGGCTCGTGAGATCGAAGCCAAGCTCGCCAAGCTGCCGCA<br>GGTATCGCGCACCATCTCGCTCGACACTTTCGTGCCGCCGGACCAGCCGGAGAAG<br>CTGAAGCTGATCCAGGCCGGCGCCAAGGTGCTGGAGCCCGCGCTCAATCCCGAG<br>CAGATCGATCCGCCGCCGTCCGATCAGGACAATATCGCGTCGCTGAAGAGCTCG<br>GCCGAAGCGCTGCCGCGCCGCCGGCGAGGCCACTGGACCCGGCGCCGACGCC<br>TCGCGCCGGCTCGCTACCGCGCTGACCAAGCTTGCGGGCGCCGATCAGGCGATG<br>CGCGAGAAGGCCCAGGACGTGTTCGTGCGGCCGCTGCTGCTCGACTTCGAACTGC<br>TGCGCAACATGCTGAAAGCGCAGCCGGTGACGCTCGACAACCTGCCGGCCGACA<br>TCGTGTCGTCGTGGAAGACCAAGGACGGTCAGATCCGCGTCGAGGTGCTGCCGA<br>GCGGCGACCCCAACGACAACGATACGCTGCGCAAGTTCGCCGCCGCCGTGCTGC<br>AGGCCGAGCCGTTGGCGACCGGCGGTCCGGTGTCGATCCTGAAGTCGGGCGATA<br>CCATCGTGGCCTCGTTCATCCAGGCCGGGCTGTGGGCGTTATTGTCGATCTCGAT<br>CCTGCTGTGGATCACGCTGCGCCGGATTTCCGACGTGGCGCTGACCCTGGTGCCG<br>CTGCTGGTGGCCGGTGCGGTGACGCTGGAGATCTGCGTGCTGATCGATCTGCCGC<br>TGAACTTCGCCAACATCGTCGCCTTGCCGCTGCTGCTCGGCGTCGGCGTCGCGTT<br>CAAGATCTATTACGTGACCGCCTGGCGCTCCGGCCGCACCAACCTGCTGCAGTCG<br>GCGCTGACCCGGGCGATTTTCTTCAGCGCCCTGACCACCGCCACCGCATTCGGCA<br>GCCTGTGGCTGTCGAGCCATCCGGGAACGGCCAGCATGGGCAAGCTGCTGGCGC<br>TGTCGTTGCTCACCACGCTCGGTGCCGTGCTGCTGTTCCAGCCGGCCCTGATGGG<br>CAAGCCGCGCCACATCGACGAGTCCGGCGACACCGATCTGTGA | 31 |
| hpnO | ATGTATCAGCCGAATTTAGACCTTGCCGAGATGTTTGCGGCGCGCGAAGCGAACC<br>GCAGTTCGATGCACGCCCGGCATCTCAACGAGCAGCTCGTCCGCGTCCTCAAAAC<br>CATCGGCTACGACGTCGGCTTCCAGAAGGGCACCGGTCAGTACCTCTACGACCGC<br>GACGGCGCCCGCTATCTCGACCTGCTCAGCGGCTTTGGCGTCTTCGCGCTCGGCC<br>GCAACCATCCGGTGGTGCGCAAGGCGTTGCAGAGCGTGCTCGATGCCGACCTGC<br>CCAATCTGGTGCAGCTCGACGTCTCGACGCTCGCCGGTATCCTGGCTGAGCGGCT<br>GCTCGAGCAGGTGCCGTATCTCGACAAGGTGTTCTTCGCCAATTCCGGCGCCGAG<br>AGCGTCGAGGCCGCGATCAAGTTCGCGCGCGGTGCAACGGGACGCAACGGTATC<br>GTCAATTGCGACCACAGCTACCATGGCCTGACCTACGGCGCGCTGTCGCTGACCG<br>ACGACCAGAATTTCCAGGGTGGCTTTGGGCCGCTGCTGCCGGGTGTCACCACCAT<br>CCCGTTCAACGATCTCGAAGCGCTGGAGAAGGTGCTGTCGACCCGCGAGGTCGC<br>CGCCTTCATCGTCGAGCCGATCCAGGGCAAGGGCGTCAACATGCCCACCGACGA<br>GTTCCTGCCGGGCGCCGCCGCGCTGTGCAAACGCTACGGCACGTTGTTCGTCGCC<br>GACGAAATCCAGACCGGCATGGGCCGCACCGGCCGCTTCCTCGCGGTCGAGCAC<br>TGGAATGTCGAACCCGACATGGTGCTGCTGTCGAAGGCGCTGTCGGGCGGCCAC<br>GTACCGGTCGGCGCGGTGCTGACCCGCAAGTCGATCTTCGACAAGATCTTCAACC<br>GCATGGATCGCGCCGTGGTGCACGGCTCGACCTTCGCCAAGAACGATCTGGCGA<br>TGGCTGCCGGCATTGCGACGCTGGAAGTCCTCAAAGCCGAGAAGCTGGTCGAGG<br>CCGCCGCCAAGCGCGGCGCCGAATTGCGGCTGGCGCTCACGCGCATGGTCCCCG<br>GCTACGAACTGCTCAAGGAAGTGCGCGGCAAGGGGCTGATGATCGGCGTCGAAT<br>TCGGCCCGCCGCAATCGCTGCGGCTGAAGGCGTCGTGGACGATGCTGGAGACCG | 32 |

TABLE 2-continued

DNA sequences of R. palustris hopanoid biosynthesis genes

| Gene Name | DNA sequence | SEQ ID NO |
|---|---|---|
| | CCAACAAGGGCCTGTTCGTCCAGCTGATCACCGTGCCGCTGTTCAAGGATCACAA GATCCTGACGCAGGTCGCGGGCCATGGGCTGCACACCATCAAGCTGCTGCCGCC GCTGACCATCACCGAAGACGACTGCGCCTGGATCGAACGCGCCTTCGACGACAC CATCGCTGCCAGCCACAAGGTGCCGGGCGCGATCTGGTCGCTCGGCAAGACCCT GGTCGACAACGCGGTGCGTAAGTCGGCGTAA | |

Example 3: Bacterial Strains and Growth Conditions

For microaerobic growth of *Bradyrhizobium diazoefficiens* in peptone-salts-yeast extract (PSY), the medium was made anaerobic by boiling under a stream of nitrogen for 10 minutes, dispensing 25 ml cooled medium in 500 ml anaerobic bottles in a nitrogen chamber, exchanging gas phase of stoppered media bottles with nitrogen for an hour, followed by autoclaving. The sterilized medium was inoculated with aerobic PSY-grown log-phase cultures at $10^{-2}$ dilution and the gas phase exchanged with 12-14 psi 99.5/0.5% nitrogen/oxygen gas mix for 3-5 minutes every 8-16 hours (h) [32]. In all media, *B. diazoefficiens* strains were incubated at 30° C. with shaking at 250 rpm for aerobic cultures and 60 rpm for microaerobic cultures, unless indicated otherwise. Antibiotics were used for selection at these concentrations (μg/ml): spectinomycin, 100; kanamycin (Km), 100; tetracycline (Tc), 50.

Example 4: Sequence Analysis

The Integrated Microbial Genome (IMG) system (https://img.jgi.doe.gov/cgi-bin/w/main.cgi) was used to access DNA and protein sequences, identify orthologs and assess genomic context of genes [33].

Example 5: Mutant Construction

Fusion PCR products of ~1 Kb upstream and downstream regions of genes of interest were cloned into pK18mobsacB to obtain deletion plasmids that were mobilized into WT and selected using Km resistance (Table 3). Subsequently, the plasmid integrants were resolved by growth in non-selective medium and segregants were obtained by 5% sucrose selection. Potential mutants were screened by PCR and verified by sequencing. Deletion of shc (hpnF) and the hpnCDEFG (FIG. 2B) operon using pK18mobsacB- and pSUP202pol4-based plasmids (Table 3) were attempted. For the latter, a 1.2 Kb Km resistance cassette from pBSL86 was sub-cloned between ~1 Kb upstream and downstream regions of the genes in pSUP202pol4. Following selection of deletion plasmids with Km resistance, potential Km resistant and Tc sensitive mutants were screened by PCR. It was unable to isolate an shc mutant with either methods in PSY at 30° C. or room temperature (23-25° C.) with and without 100 μM cholesterol or diplopterol as supplements. Counterselection of shc deletion plasmid segregants at lower sucrose concentrations (1-4%) were also carried out, but the mutant was still not obtained. Tables 3 and 4 list the strains, plasmids and primers used in constructing the mutants.

TABLE 3

Strains and plasmids

| Strain or plasmid | Genotype, description and construction[a] | Source or US[b] |
|---|---|---|
| Strains | | |
| E. coli DH10B | F⁻ endA1 recA1 galE15 galK16 nupG rpsL ΔlacX74 Φ80lacZΔM15 araD139 Δ(ara,leu)7697 mcrA Δ(mrr-hsdRMS-mcrBC) λ⁻; DKN89 | [34] |
| E. coli S17-1 | thi pro hdsR hdsM⁺ recA; chromosomal insertion of RP4-2 (Tc::Mu Km::Tn7); DKN1 | [35] |
| DKN1391 | B. japonicum 110spc4, Sp[r], WT | [36] |
| DKN1386 | B. japonicum 110spc4 ΔhpnP; deletion of blr2995 in DKN1391 using pGK247 | This study |
| DKN1529 | B. japonicum 110spc4 ΔhpnH; deletion of blr3006 in DKN1391 using pGK255 | This study |
| Plasmids | | |
| pK18mobsacB | Km[r] mobilizable pUC18 derivative, mob, sacB (DKN1387) | [37] |
| pSUP202pol4 | Tc[r] pSUP202 part of the polylinker subcloned into pBluescript II KS (+) using EcoRI and PstI sites (DKN1390) | [38] |
| pBSL86 | Ap[r], Km[r] (DKN1388) | [39] |
| pGK259 | shc deletion vector; HindIII/PstI-digested blr3004 (shc) upstream and downstream fusion PCR product amplified using primers shcupfor, shcuprevfusion-new, shcdnforfusion-new and shcdnrev was ligated to HindIII/PstI-digested pK18mobsacB (DKN1492) | This study |
| pGK248 | NotI/XbaI-digested shc upstream PCR product amplified using primers pSUPshcupfor and pSUPshcuprev was ligated to NotI/XbaI-digested pSUP202pol4 (DKN1421) | This study |

TABLE 3-continued

Strains and plasmids

| Strain or plasmid | Genotype, description and construction[a] | Source or US[b] |
|---|---|---|
| pGK262 | XbaI/PstI-digested shc downstream PCR product amplified using primers pSUPshcdnfor-new and pSUPshcdnrev was ligated to XbaI/PstI-digested pGK248 | This study |
| pGK263 | shc deletion vector; 1.2 Kb Km[r] cassette from XbaI-digested pBSL86 sub-cloned into XbaI-digested pGK262 (DKN1430) | This study |
| pGK268 | hpnCDEFG deletion vector; blr3001 (hpnC) upstream and blr3005 (hpnG) downstream PCR products amplified using primers hpnCupforw/pK18fusion, hpnCuorevw/hpnGfusion and hpnGdnforw/hpnCfusion, hpnGdnrevw/pK18fusion were Gibson cloned into XbaI/PstI-cut pK18mobsacB (DKN1604) | This study |
| pGK269 | NotI/XbaI-digested hpnC upstream PCR product amplified using primers hpnCupfor and hpnCuprev was ligated to NotI/XbaI-digested pSUP202pol4 (DKN1605) | This study |
| pGK270 | XbaI/PstI-digested hpnG downstream PCR product amplified using primers hpnGdnfor and hpnGdnrev was ligated to XbaI/PstI-digested pGK269 (DKN1606) | This study |
| pGK276 | hpnCDEFG deletion vector; 1.2 Kb Km[r] cassette from XbaI-digested pBSL86 sub-cloned into XbaI-digested pGK270 (DKN1609) | This study |
| pGK247 | hpnP deletion vector; BamHI/PstI-digested hpnP upstream and downstream fusion PCR product amplified using primers hpnPupfor, hpnPuprevfusion, hpnPdnforfusion and hpnPdnrev was ligated to BamHI/PstI-digested pK18mobsacB (DKN1395) | This study |
| pGK255 | hpnH deletion vector; HindIII/PstI-digested hpnH upstream and downstream fusion PCR product amplified using primers hpnHupfor, hpnHuprevfusion, hpnHdnforfusion and hpnHdnrev was ligated to HindIII/PstI-digested pK18mobsacB (DKN1482) | This study |

[a]Km, Kanamycin; Sp, Spectinomycin
[b]underlined sequence

1. Casadaban, M. J., and Cohen, S. N. 1980. Analysis of gene control signals by DNA fusion and cloning in *Escherichia coli*. J Mol Biol 138: 179-207.
2. Simon, R., Priefer, U., and Puhler, A. 1983. A broad host range mobilization system for in vivo genetic engineering - transposon mutagenesis in Gram negative bacteria. Bio-Technol 1: 784-791.
3. Regensburger, B., and Hennecke, H. 1983. RNA polymerase from *Rhizobium japonicum*. Arch Microbiol 135: 103-109.
4. Schafer, A., Tauch, A., Jager, W., Kalinowski, J., Thierbach, G., and Puhler, A. 1994. Small mobilizable multi-purpose cloning vectors derived from the *Escherichia coli* plasmids pK18 and pK19: selection of defined deletions in the chromosome of *Corynebacterium glutamicum*. Gene 145: 69-73.
5. Fischer, H. M., Babst, M., Kaspar, T., Acuna, G., Arigoni, F., and Hennecke, H. 1993. One member of a groESL-like chaperonin multigene family in *Bradyrhizobium japonicum* is co-regulated with symbiotic nitrogen fixation genes. The EMBO journal 12: 2901-2912.
6. Lindemann, A., Koch, M., Pessi, G., Muller, A. J., Balsiger, S., Hennecke, H., and Fischer, H. M. 2010. Host-specific symbiotic requirement of BdeAB, a RegR-controlled RND-type efflux system in *Bradyrhizobium japonicum*. FEMS microbiology letters 312: 184-191.

TABLE 4

Primers

| Primers | Sequences | Source | SEQ ID NO |
|---|---|---|---|
| Shcupfor | TATCTAGAAAGCTTGCAGTTTCCCTTCGTCGATA | HindIII | 1 |
| shcuprevfusion-new | ACCATGATACCGTAGATAGAATACACGGGGCATCTGGCTCGATTACTCCGATAGTTAATT | | 2 |
| shcdnforfusion-new | AATTAACTATCGGAGTAATCGAGCCAGATGCCCCGTGTATTCTATCTACGGTATCATGGT | | 3 |
| Shcdnrev | TATCTAGACTGCAGAGCAGGTCCAGAAGAAGCTC | PstI | 4 |
| pSUPshcupfor | TATATATAGCGGCCGCGCAGTTTCCCTTCGTCGATA | NotI | 5 |
| pSUPshcuprev | TATATATATCTAGACATCTGGCTCGATTACTCCGATAGTTAATT | XbaI | 6 |
| pSUPshcdnfor-new | TATATATATCTAGACCCCGTGTATTCTATCTACGGTATCATGG | XbaI | 7 |
| pSUPshcdnrev | TATATATACTGCAGAGCAGGTCCAGAAGAAGCTC | PstI | 8 |
| hpnCupforw/pK18 fusion | TTCGAGCTCGGTACCCGGGGATCCTCTAGAGTGGAACCGTCGGACAGC | | 9 |

TABLE 4-continued

Primers

| Primers | Sequences | Source | SEQ ID NO |
|---|---|---|---|
| hpnCuprevw/hpnG fusion | TTGTCAGATCGAGACGCTCACTGGTTTACAATCGTTTGGA CAGGAAGAGC | | 10 |
| hpnGdnforw/hpnC fusion | GCTCTTCCTGTCCAAACGATTGTAAACCAGTGAGCGTCTC GATCTGACAA | | 11 |
| hpnGdnrevw/pK18 fusion | ACGGCCAGTGCCAAGCTTGCATGCCTGCAGGCTGATCCAC AAGGAGATCG | | 12 |
| hpnCup for | TATATATAGCGGCCGCGTGGAACCGTCGGACAGC | NotI | 13 |
| hpnCuprev | TATATATATCTAGACTGGTTTACAATCGTTTGGACAGGAA GAGC | XbaI | 14 |
| hpnGdnfor | TATATATATCTAGATGAGCGTCTCGATCTGACAA | XbaI | 15 |
| hpnGdnrev | TATATATACTGCAGGCTGATCCACAAGGAGATCG | PstI | 16 |
| hpnPupfor | TATCTAGACTGCAGAACACCATCGGGCTGAAG | PstI | 17 |
| hpnPuprevfusion | GGAAGCCTCGCGCAGCCGGATCGAATAGTTCATAGCGTA ATGCTGTCGCCGGAATTTCTC | | 18 |
| hpnPdnforfusion | GAGAAATTCCGGCGACAGCATTACGCTATGAACTATTCGA TCCGGCTGCGCGAGGCTTCC | | 19 |
| hpnPdnrev | TATCTAGAGGATCCTTTTCGAGCATGCCTTATCC | BamHI | 20 |
| hpnHupfor | TATCTAGAAAGCTTAACTTTGAAGCGGATTGGTG | HindIII | 21 |
| hpnHuprevfusion | TTTTTGTTCGTGGTGCTGTTTCTCGCCTTACATTACACGTT TCTTTCTGGGCTTGAAATT | | 22 |
| hpnHdnforfusion | AATTTCAAGCCCAGAAAGAAACGTGTAATGTAAGGCGAG AAACAGCACCACGAACAAAAA | | 23 |
| hpnHdnrev | TATCTAGACTGCAGCCTGATTGCAACACAGAACG | PstI | 24 |

Example 6: Hopanoid Analysis

Triplicate cultures of *B. diazoefficiens* strains were grown till saturation in aerobic (100 ml PSY in 500 ml flasks) and microaerobic (25 ml PSY in 500 ml Wheaton bottles) growth media. They were centrifuged at 5000×g for 20 min at 4° C. and frozen at −80° C. until extraction. Cell pellets were suspended in 2 ml water and transferred to Teflon centrifuge tubes (VWR, Bridgeport, N.J.), followed by addition of 5 ml methanol (MeOH) and 2.5 ml dichloromethane (DCM) and sonicated for 15 min at room temperature (VWR B2500A-DTH; 42-kHz radio frequency power, 85 W). Samples were centrifuged at 7000×g for 10 min at 22° C. and the supernatants transferred to new tubes. Cell pellets obtained from aerobically-grown cultures were sonicated again, centrifuged, and the supernatants combined with the first extraction. The samples were separated into two phases by adding 7.5-13 ml DCM and centrifuged at 6000×g for 10 min at 22° C. The organic phase was transferred to a new vial and evaporated in a chemical hood overnight. The total lipid extract (TLE) was resuspended in DCM at a concentration of 1 mg/ml. 100 µl of this extract was combined with 1 µl of an internal standard (500 ng/µl pregnane-acetate [40]) and evaporated at 60° C. The TLE was derivatized to acetate esters by incubation in 100 µl 1:1 acetic anhydride/pyridine for 30 min at 60° C. and then analyzed by gas chromatography/mass spectrometry (GC-MS). Peak areas of hopanoid species were integrated and compared to those from pregnane-acetate standards to obtain the yields from TLE [41].

For liquid chromatography/mass spectrometry (LC-MS), 100 µl 1 mg/ml TLE was evaporated under nitrogen, dissolved in isopropanol-acetonitrile-water (2:1:1) or DCM-MeOH (9:1) and then analyzed [26]. Hopanoid peaks were identified by comparison of retention times and mass spectra to those of *Rhodopseudomonas palustris* TIE-1 (Tables 5 and 6) [26, 41].

TABLE 5

Compounds identified by high temperature GC-MS

| Compound | Rt (min) | Diagnostic ions (m/z) |
|---|---|---|
| Pregnane-acetate (I) | 15.93 | 358, 298, 283, 255, 145, 105, 79 |
| 2-Methylhop-17(21)-ene | 17.37 | 424, 381, 245, 205, 161, 135 |
| Hop-17(21)-ene (II) | 17.51 | 410, 367, 231, 191, 161, 135 |
| 2-Methylhop-x-ene | 19.30 | 424, 409, 281, 205, 189, 95 |
| Hop-x-ene (III) | 19.49 | 410, 395, 243, 203, 191, 189, 95 |
| 2-Methylhop-22(29)-ene | 20.27 | 424, 313, 205, 189, 95 |
| Hop-22(29)-ene (Diploptene, IV) | 20.47 | 410, 299, 191, 189, 95 |
| 2-Methylhop-21-ene | 20.33 | 424, 381, 355, 245, 205, 189, 121 |
| Hop-21-ene (V) | 20.52 | 410, 367, 341, 231, 191, 189, 121 |
| 2-Methylhopan-22-ol | 23.84 | 442, 409, 205, 189, 149, 95 |
| Hopan-22-ol (Diplopterol, VI) | 24.05 | 428, 395, 191, 189, 149, 95 |
| 2-Methyltetrahymanol | 24.84 | 484, 424, 249, 205, 189, 83 |
| 20-Methyltetrahymanol | 24.84 | 424, 409, 249, 205, 189 |
| Tetrahymanol (VII) | 25.09 | 470, 410, 249, 191, 189, 69 |
| BHP-508 (VIII) | 34.78 | 508, 493, 369, 287, 213, 191, 111 |

TABLE 5-continued

Compounds identified by high temperature GC-MS

| Compound | Rt (min) | Diagnostic ions (m/z) |
|---|---|---|
| 2-Methylbacteriohopanetetrol | 38.11 | 728, 669, 493, 383, 205, 95 |
| Bacteriohopanetetrol | 38.44 | 714, 655, 493, 369, 191, 95 |

TABLE 6

Compounds identified by ultra performance LC-MS

| Compound | Rt (min) | m/z | Ion |
|---|---|---|---|
| Aminobacteriohopanetriol (aminotriol, a) | 4.34 | 546.487 | $[M + H]^+$ |
| 2-Methylaminobacteriohopanetriol (c) | 4.76 | 560.504 | $[M + H]^+$ |
| Bacteriohopanetetrol (BHT) | 5.66 | 529.462 | $[M - H_2O + H]^+$ |
| Bacteriohopanetetrol (b) | 5.66 | 569.454 | $[M + Na]^+$ |
| Adenosylhopane (d) | 5.94 | 662.501 | $[M + H]^+$ |
| 2-Methylbacteriohopanetetrol | 6.22 | 543.478 | $[M - H_2O + H]^+$ |
| 2-Methylbacteriohopanetetrol (e) | 6.20 | 583.470 | $[M - Na]^+$ |

Example 7: Lipid a Analysis

Bacterial cells were extracted using the phenol/water method [42] and after extensive dialyses, the extracted phases were subjected to enzymatic digestion with DNases, RNases and proteases in order to remove nucleic acids and protein contaminants and recovered by ultracentrifugation (100 000×g, 4° C., 24 h). Water phases were analysed through 13.5% SDS-PAGE; the lipopolysaccharide (LPS) fraction was exclusively found in water phase as suggested by the presence of the typical ladder in its migration pattern in the gel. The LPS material was further purified by a second extraction with phenol/chloroform ($CHCl_3$)/petroleum methods to get rid of glucan contaminants, and LPS fractions were further purified by size filtration chromatography (Sephacryl S-400 HR in 50 mM ammonium carbonate ($NH_4CO_3$) from GE Healthcare).

LPS sugar content was determined by GLC-MS analysis of acetylated O-methyl derivatives. Methanolic hydrochloric acid (HCl) was added to dried LPS and incubated at 85° C. for 16 h, the sample was subsequently acetylated with pyridine and $Ac_2O$, 85° C., 20 min and analysed by GLC-MS [43]. Linkage analysis was carried out by methylation analysis. The sample was hydrolyzed with 4 M trifluoroacetic acid (100° C., 4 h), carbonyl-reduced with sodium borodeuteride ($NaBD_4$), carboxy-methylated, carboxyl-reduced, acetylated and analysed by GLC-MS [44]. Total fatty acid content was obtained by acid hydrolysis. LPS was first treated with 4M HCl (4 h, 100° C.) and then with 5M sodium hydroxide (NaOH, 30 min, 100° C.). Fatty acids were then extracted in $CHCl_3$, methylated with diazomethane and analysed by GLC-MS. The ester bound fatty acids were selectively released by base-catalysed hydrolysis with 0.5M NaOH/MeOH (1:1 v/v, 85° C., 2 h), then the product was acidified, extracted in $CHCl_3$, methylated with diazomethane and analysed by GLC-MS [45].

In order to obtain lipid A, LPS was dissolved in acetate buffer (pH 4.4), and was hydrolyzed for 5 h at 100° C. Then, adequate amounts of $CHCl_3$ and MeOH were added to the hydrolysate to obtain $CHCl_3$/MeOH/hydrolysate 2:2:1.8 (v/v/v), and the mixture was vigorously shaken, then centrifuged [46]. The lipid A-containing $CHCl_3$ phases were collected and washed twice with the water phase from a freshly prepared two-phase Bligh-Dyer mixture ($CHCl_3$/MeOH/water, 2:2:1.8 (v/v/v)].

For MALDI TOF MS, a 4800 Proteomic Analyzer (AB-Sciex), MALDI TOF/TOF instrument equipped with a Nd:YAG laser at a wavelength of 355 nm with <500-ps pulse and 200-Hz firing rate was employed. External calibration was performed using an ABSciex calibration mixture. All measurements were performed in positive polarity. Approximately, 1500 laser shots were accumulated for each spectrum in the MS experiments. Samples were dissolved in $CHCl_3$/MeOH (50:50, v/v) at a concentration of 1 mg/ml. Matrix solution was prepared by dissolving trihydroxyacetophenone (THAP) in MeOH/0.1% trifluoroacetic acid/acetonitrile (7:2:1, by volume) at a concentration of 75 mg/ml. 1 µl of the sample/matrix solution (1:1, v/v) was deposited onto the well plate and allowed to dry at room temperature.

Example 8: Membrane Rigidity

For whole cell membrane rigidity measurements, as described in [8], PSY-grown aerobic cultures of *B. diazoefficiens* strains were washed once with 4-(2-hydroxyethyl)-1-piperazineethanesulfonic acid (HEPES) buffer (50 mM HEPES, 50 mM sodium chloride (NaCl), pH 7.0) and then resuspended in the same to an $OD_{600}$~0.2 with 7.36 µM of the fluorophore diphenyl hexatriene (DPH). Prior to measurement of fluorescence polarization, samples were incubated in a 25° C. or 40° C. water bath in dark for 30 min. Three biological replicates were measured, each containing 8 technical replicates.

Example 9: CRYO-TEM (Transmission Electron Microscopy

PSY-grown aerobic cultures at an $OD_{600}$ of 1 were concentrated 5 times and frozen in a Vitrobot MkIV (FEI, Hillsboro, Oreg.) as described previously [47, 48]. In brief, 2 µl of a 10 nm colloidal gold (Sigma Aldrich, St. Louis, Mo.) in 5% Bovine serum albumin (BSA) was added to 8 µl of culture. 3 µl of this suspension was placed onto a glow discharged carbon-coated R 2/2 Quantifoil copper-finder grid in the Vitrobot maintained at 22.5° C. with 95% humidity. This was followed by a 3 s blot with a pressure of 6 atm, a drain time of 1 sec, and plunge freezing in a mixture of liquid ethane (63%) and propane (37%). The frozen grids were then stored in liquid nitrogen until further use. Grids were imaged in Tecnai TEM 120 KeV (FEI, Hillsboro, Oreg.) at −178° C. using a Gatan 626 cryoholder and Gatan 2×2K CCD. Images were acquired with Digital Micrograph at 15,000× magnification [49, 50].

Example 10: Growth Curves and Stress Assays

To monitor growth in different media, triplicate cultures were inoculated at $10^{-2}$ dilution using aerobic PSY-grown log-phase ($OD_{600}$=0.5-0.7) WT or mutant strains. Growth was measured at $OD_{600}$ using a Spectronic 20D+ (Thermo Scientific) or a Beckman Coulter spectrophotometer for microaerobic medium. Unless otherwise indicated, the incubation temperature was 30° C. Growth curves were performed in triplicates at least twice independently.

Sensitivity to high temperature (37° C.) and low or high pH was measured by monitoring growth in PSY at $OD_{600}$ using Spectronic 20D+. Acidic (pH=6) and alkaline (pH=8)

media were prepared by buffering PSY with 100 mM MES (4-Morpholineethanesulfonic acid) and 100 mM bicine (N,N-Bis(2-hydroxyethyl)glycine) or BIS-TRIS Propane, respectively. It was unable to collect a growth curve at pH=8 because this was outside the WT growth range. Growth curves were performed in triplicates at least twice independently.

Growth in the presence of osmotic and membrane stresses was measured using gradient plates. To prepare these, 25 ml of 50 mM 3-(N-morpholino)propanesulfonic acid (MOPS)-buffered PSY agar (pH=7) with 50 mM NaCl, 500 mM inositol, 0.4% bile salts (BS, Himedia, Mumbai, India) or 1 mM ethylenediaminetetraacetic acid (EDTA) was poured in a slightly tilted square grid plate (Fisher, Pa.). The solidified plate was topped with 25 ml PSY-MOPS agar. Control plates contained 50 ml PSY-MOPS agar. 5 µl of aerobic PSY-grown log-phase cultures at $10^{-4}$ dilution were spotted on the plates. To assess stationary-phase stress, saturated instead of log-phase cultures were used for plating. The plates were incubated at 30° C. for 5-7 days. Spotting assays were performed in duplicates at least two independent times.

Disk diffusion assays were used to quantify growth under oxidative, acidic and detergent stresses. For this, 4 day-old cultures of *B. diazoefficiens* strains grown in yeast extract-mannitol (YM) medium were washed and adjusted to an $OD_{600}$ of 1. 2 ml bacterial suspensions were then mixed with 100 ml of 42° C. pre-warmed YM soft agar (0.8% agar) and 5 ml portions of this mixture were poured on solid YM. Filter disks were placed at the center of the plates, and 5 µl of 5.5 M $H_2O_2$, 2 M HCl or SDS (10% w/v), were deposited on the disks. The diameters of growth inhibition areas were measured after incubation at 30° C. for 5 days.

Example 11: MIC Determination

The MIC of polymyxin B was determined by the E-test method using disk diffusion assay as described above. Strips containing a gradient of polymyxin B ranging from 0.064-1024 µg/mL (Biomérieux, Marcy-l'étoile, France) were placed in the center of plates, which were incubated at 30° C. for 7 days before recording the results. The experiment was done in triplicates.

The effect of the NCR335 peptide on cell viability was determined by spot assays. YM-grown exponential phase cultures were washed three times in 10 mM potassium phosphate buffer pH 7.0, diluted to an $OD_{600}$ of 0.01, and treated with 6 µM NCR335 for 24 h at 30° C. Samples were serially diluted in YM medium, and 5 µl aliquots of each dilution were spotted in duplicate on YM agar. CFU/ml were determined after 7 days at 30° C. The experiment was performed in triplicates.

Example 12: Plant Cultivation and Symbiotic Analysis

*A. afraspera* seeds were surface sterilized by immersion in sulfuric acid for 45 minutes with shaking, followed by thorough washing in sterile distilled water and incubation in the same overnight. The seeds were germinated by transferring to 0.8% agar plates for 2 days at 37° C. in dark. Subsequently, plantlets were rooted in buffered nodulation medium (BNM)-filled test tubes, which were covered with aluminum foil for hydroponic culturing [51]. Plants were grown in a 28° C. growth chamber with a 16 h light and 8 h dark cycle and 70% humidity. Seven days after transfer, each seedling was inoculated with a 1 ml cell suspension from a 5 day-old bacterial culture washed in BNM and adjusted to reach an $OD_{600}$ of 1.

Soybean (*Glycine max* Williams 82) seeds were cleaned with 100% ethanol for 30 seconds and sterilized with 1% bleach for 5 min. After several washes with sterile distilled water, seeds were germinated on tap-water agar plates at 28° C. for 3 days. Seedlings were then transferred to magenta boxes filled with BNM, inoculated and grown hydroponically as described above for *Aeschynomene* plants. Plants were watered with BNM medium.

Infection assays were carried out three independent times with 7 and 10 plants for soybean and *A. afraspera*, respectively. At 21 d.p.i., plants were analyzed for the number of nodules and nitrogenase activity as previously described [52].

Example 13: Cytological Analyses and Microscopy

Cytological analyses were done on 5-10 nodules originating from 3 different plants for each condition; microscopic observations were performed for each of the 3 plant experiments, except for the TEM observations which were only done once. Semi thin nodule sections (30-40 µm) were prepared using a vibratome (VT1000S; Leica, Nanterre, France). Immediately after slicing, the sections were incubated for 20 min in live/dead staining solution (5 µM SYTO 9 and 30 µM propidium iodide (PI) in 50 mM Tris pH 7.0 buffer; Live/Dead BacLight, Invitrogen). Sections were then removed and incubated an additional 15 min in 10 mM phosphate saline buffer (PBS) containing calcofluor white M2R (Sigma, Munich) to a final concentration of 0.01% (w/v) to stain the plant cell wall [53]. After washing with PBS, the sections were mounted on microscope slides in PBS containing glycerol at a final concentration of 50% (v/v). Analyses were carried out using a confocal laser-scanning microscope (Carl Zeiss LSM 700; Jena, Germany). Calcofluor was excited at 405 nm with emission signal collection at 405 to 470 nm. For SYTO 9 and PI, an excitation wavelength of 488 nm and 555 nm was used with emission signal collection at 490 to 522 nm and 555 to 700 nm, respectively. Images were obtained using the ZEN 2008 software (Zeiss).

For TEM of the nodules, the samples were fixed in a 4% glutaraldehyde, 0.1 M cacodylate buffer (pH 7.2), postfixed in 1% osmium tetroxyde, dehydrated using a series of acetone washes, and embedded in TAAB 812 epon resin. Ultrathin sections (60 nm) were mounted on collodion carbon-coated copper grids, contrasted using uranyl acetate and lead citrate, and examined at 80 kV with a TEM (Jeol 100CX II).

Example 14: Elimination of Shc in *B. diazoefficiens*

To eliminate hopanoid production in *B. diazoefficiens*, and to test whether a requirement for hopanoids in efficient symbiosis is conserved between *B. diazoefficiens* and *Bradyrhizobium* BTAi1, deletion of the gene encoding the enzyme catalyzing the first step in hopanoid biosynthesis, squalene hopene cyclase (Shc) (FIG. 2B) was carried out. A Δshc mutant was isolated using either the pK18mobsacB-based markerless gene deletion method (~400 colonies screened) or the gene replacement strategy with pSUP202pol4 (1200 colonies screened) [54]. No—we were NOT able to isolate this mutant. We don't have an shc deletion for *B. diazoefficiens*.

This suggests that Shc may be essential either because hopanoids are required for growth and survival of *B. diazo-*

*efficiens* or because squalene, the substrate of Shc [11], accumulates to toxic levels within Δshc. To rule out the latter possibility, deletion of the entire operon encoding squalene-synthesizing enzymes (hpnCDE), shc (hpnF) and hpnG (catalyzes second step in the synthesis of $C_{35}$ hopanoids) [12] was carried out. The ΔhpnCDEFG mutant (~150 colonies screened) (FIG. 2B) was unable to obtain. These results suggest that hopanoid synthesis is essential for the survival of *B. diazoefficiens* under the conditions used to select the mutants.

Example 15: *B. diazoefficiens* ΔhpnP and ΔhpnH Mutants

To eliminate synthesis of 2Me- or $C_{35}$ hopanoids specifically, genes predicted to encode the C-2 methylase, hpnP [55] or the first enzyme catalyzing the extension of $C_{30}$ hopanoids, hpnH [12] (FIG. 2B) were deleted.

As illustrated in FIG. 2C, no methylated hopanoids were detected in ΔhpnP TLE using gas chromatography-mass spectrometry (GC-MS) and liquid chromatography-mass spectrometry (LC-MS) (Tables S1 and S2) [26, 41]. ΔhpnH does not make any detectable $C_{35}$ hopanoids, including aminotriol (a, c), BHP-508 (VIII, degradation product of aminotriol), bacteriohopanetetrol (b, e) and adenosylhopane (d). In addition, ΔhpnH accumulates a 6-fold excess of the HpnH substrate [12], diploptene (IV, WT—18±2 μg/mg TLE, ΔhpnP—29±6 μg/mg TLE, ΔhpnH—111±3 μg/mg TLE).

Figure 4:
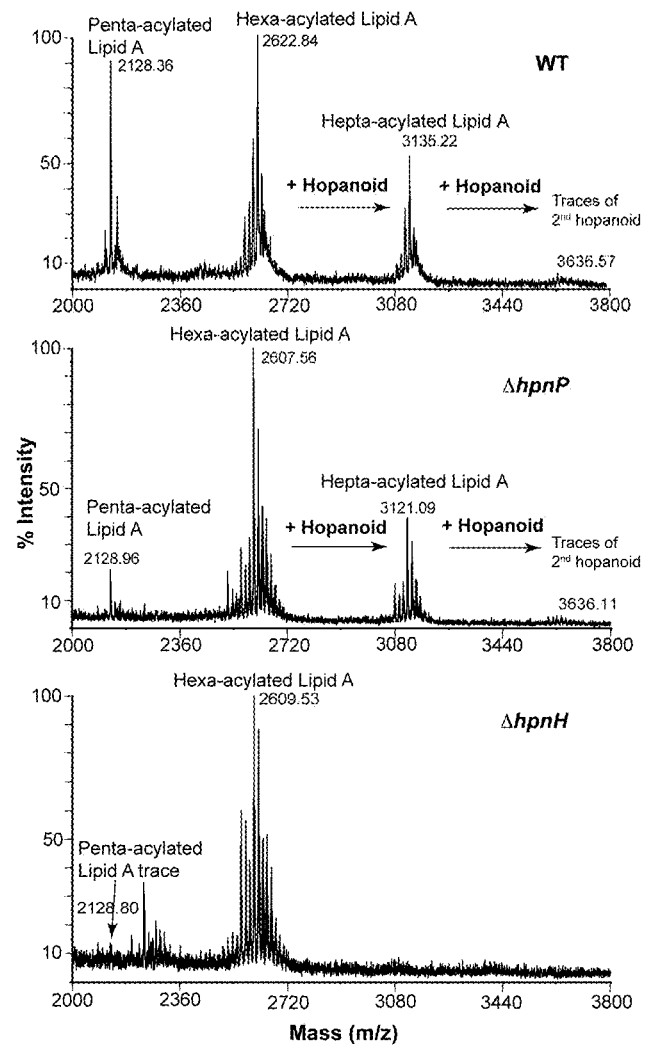
FIG. 4 shows in some embodiments the MALDI-MS analysis of lipid A from B. diazoefficiens strains. Lipid A from WT and ΔhpnP is composed of a mixture of penta-acylated and hexa-acylated species, whereas ΔhpnH lipid A is mainly hexa-acylated. A $C_{35}$ hopanediolic acid is ester-linked to hexa-acylated and hepta-acylated lipid A in WT and ΔhpnP. ΔhpnH does not contain any lipid A-bound hopanoids.

The presence of HoLA in the mutants using MALDI-MS (FIG. 4) was also analyzed. WT and ΔhpnP lipid A are composed of a mixture of penta- to hepta-acylated species, whereas ΔhpnH lipidA is mainly hexa-acylated (FIG. 1B). In WT and ΔhpnP hepta-acylated species, a $C_{35}$ hopanediolic acid is ester-linked to hexa-acylated lipid A, and traces of a second hopanoid substitution are also detected; conversely, ΔhpnH is missing any lipid A-bound hopanoids. Not only do the results confirm the proposed roles of HpnP and HpnH, they also show that synthesis of $C_{35}$ hopanoids is required for HoLA production.

Example 16: Hopanoids Contribute to Outer Membrane Rigidity

Figure 5:
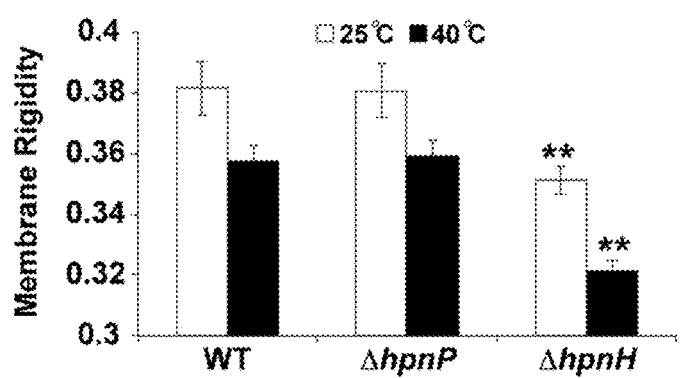
FIG. 5 plots whole cell membrane fluidity measurements by fluorescence polarization, which show that rigidity decreases for all strains as temperature increases and that the ΔhpnH membrane is less rigid than that of WT or ΔhpnP (**$p<0.01$ by Student's 2-Tailed t-test). Error bars represent the standard deviation from three biological replicates (~22 technical replicates).

A fluorescence polarization method was employed by incubating the dye diphenyl hexatriene (DPH) with whole cells to determine whether 2Me- and $C_{35}$ hopanoids affect the rigidity of *B. diazoefficiens* membranes at 25° C. and 40° C. (FIG. 5). Because previous studies of whole cells of different *R. palustris* hopanoid mutants indicated that the majority of DPH gets incorporated in the OM, whole cell polarization values was interpreted to reflect the rigidity of the OM [8, 26].

Figure 6:
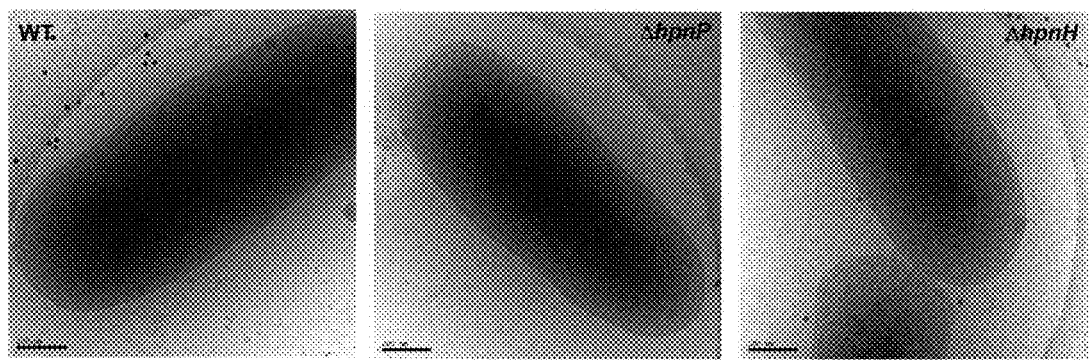
FIG. 6 shows in some embodiments the CRYO-transmission electron microscopy (TEM) micrographs which show intact outer and inner membranes in all B. diazoefficiens strains. Scale=200 nm.

Membranes of all strains were less rigid at higher temperature. The ΔhpnP membrane was as rigid as the WT membrane at both temperatures, whereas the ΔhpnH membrane was less rigid. Thus, $C_{35}$ hopanoids are important for maintaining membrane rigidity in *B. diazoefficiens* in vivo, in contrast to *R. palustris*, where the ΔhpnH membrane showed similar rigidity to the WT, despite the capacity of $C_{35}$ hopanoids to enhance rigidity in vitro [8]. This indicates that the fraction of $C_{35}$ hopanoids or HoLA in the OM may be greater in *B. diazoefficiens* than *R. palustris*. Despite the lack of $C_{35}$ hopanoids, the ΔhpnH membrane is morphologically indistinguishable from the WT membrane, as seen in whole cell cryo-transmission electron microscopy (TEM) micrographs (FIG. 6).

Example 17: Aerobic Growth of *B. diazoefficiens* WT, ΔhpnP and ΔhpnH Mutants

To address the question whether a less rigid membrane affect the fitness of ΔhpnH at different temperatures, aerobic growth of ΔhpnH at 30° C. and 37° C. were compared with WT and ΔhpnP (FIGS. 7A and B). ΔhpnP grows like WT at both temperatures, whereas ΔhpnH grows slower at 30° C. and is unable to grow at 37° C.

These results suggest that $C_{35}$ hopanoids are important for growth at ambient temperature (30° C.) and essential for growth at higher temperature (37° C.). As shown in our whole cell membrane fluidity measurements, the higher the temperature, the less rigid the membrane. This might be the reason why $C_{35}$ hopanoids are absolutely required to maintain membrane rigidity at 37° C., but are dispensable at 30° C. It is important to note that the phenotypic defect of ΔhpnH could be either due to the absence of $C_{35}$ hopanoids or the lack of downstream products, such as HoLA, and even accumulation of the HpnH substrate diploptene, or a combination of these factors.

Example 18: Stress Tolerance Tests of *B. diazoefficiens* ΔhpnP and ΔhpnH Mutants Hopanoids have been shown to contribute to stress tolerance in diverse organisms [7, 9-11]. It is speculated that such protection would also be seen in *B. diazoefficiens*. To test this hypothesis, ΔhpnP and ΔhpnH were challenged with a variety of stressors that are relevant during the initiation and progression of symbiosis, such as hypoxia, acidic pH, high osmolarity, reactive oxygen species and peptide antibiotics [1, 56].

Figure 7:
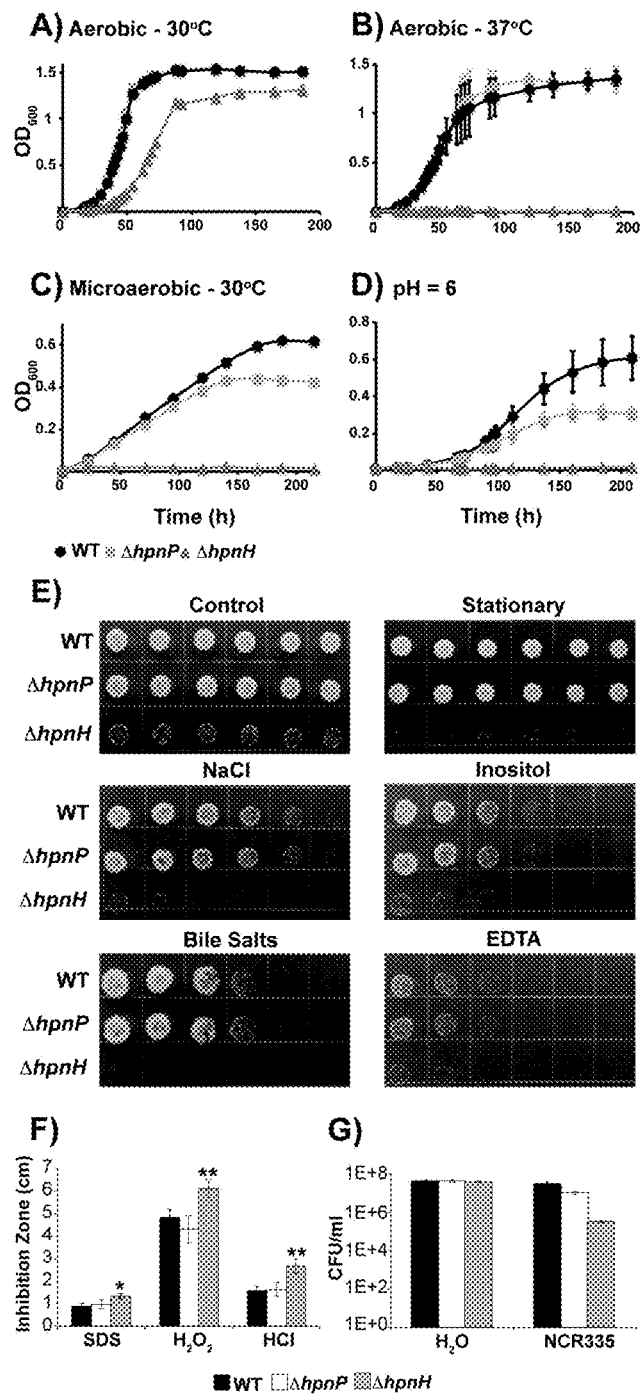
FIG. 7 shows in some embodiments the growth of B. diazoefficiens strains under various stress conditions. Growth of WT (circle), ΔhpnP (square) and ΔhpnH (triangle) was monitored at $OD_{600}$ in Panel A) PSY at 30° C., Panel B) PSY at 37° C., Panel C) microaerobic PSY with 0.5% $O_2$ at 30° C., Panel D) PSY at pH=6 and 30° C. Each curve represents the average of at least three biological replicates, except the microaerobic growth curves for which a representative data set out of four trials is shown. Growth of B. diazoefficiens strains under stress as measured in Panel E) stressor gradient plates with 50 mM NaCl, 500 mM inositol, 0.4% bile salts or 1 mM EDTA or by Panel F) disc diffusion assays with 10% SDS, 5.5 M $H_2O_2$ and 2 M HCl. Error bars represent standard error (n=9). *$p<0.05$ and **$p<0.01$ by Tukey's HSD test. Panel G) NCR335 sensitivity of B. diazoefficiens strains.

Under hypoxic conditions with 0.5% oxygen, ΔhpnP is unable to attain growth yields as high as WT and ΔhpnH fails to grow (FIG. 7C). This indicates that in the free-living state 2Me-hopanoids contribute to microaerobic growth and $C_{35}$ hopanoids are essential.

Using GC-MS, the abundance of these hopanoid types in the WT (Table 7) was determined. The amount of 2Me-hopanoids dramatically increased from 33±2% TLE under oxic conditions to 77±2% TLE under hypoxic conditions. This is consistent with hopanoid methylation being important to sustain WT-levels of microaerobic growth. The only $C_{35}$ hopanoid detectable by GC-MS, BHP-508, increased in abundance from 3±1% TLE for cells grown aerobically to 21±1% TLE when grown microaerobically, in agreement with a microaerobic growth defect for ΔhpnH.

TABLE 7

Hopanoid and tetrahymanol quantification by GC-MS using pregnane-acetate as standard

| Growth condition | Strain | % Total hopanoids[a] | | | % 2Me[b] |
|---|---|---|---|---|---|
| | | $C_{30}$ | Tetrahymanol | $C_{35}$ | |
| Aerobic (PSY) | WT | 69 ± 1 | 28 ± 1 | 3 ± 1 | 33 ± 2 |
| | ΔhpnP | 72 ± 6 | 23 ± 4 | 5 ± 2 | 0 |
| | ΔhpnH | 94 ± 0 | 6 ± 0 | 0 | 11 ± 0.2 |
| Microaerobic | WT | 34 ± 2 | 46 ± 4 | 21 ± 1 | 77 ± 2 |
| | ΔhpnP | 61 ± 1 | 34 ± 0.3 | 6 ± 1 | 0 |
| | ΔhpnH | NG[c] | NG | NG | NG |

[a]Total hopanoids = methylated and unmethylated versions of $C_{30}$ hopanoids (compounds II, III, IV, V, VI) + tetrahymanol (VII) and $C_{35}$ hopanoids (VIII) (refer to table 5 for compound names).
[b]% 2Me = ratio of methylated to total hopanoids
[c]NG, no growth Under acidic conditions (pH=6), ΔhpnH is unable to grow (FIG. 7D). ΔhpnH is also more prone to stationary phase stress, osmotic stressors (NaCl and inositol) and membrane destabilizers (bile salts and ethylenediaminetetraacetic acid, EDTA [12]) than WT, as evidenced by a reduction in ΔhpnH growth on stressor gradient plates (FIG. 7E).

Additionally, disc diffusion assays showed that ΔhpnH is more sensitive to oxidative (hydrogen peroxide ($H_2O_2$)), detergent (SDS) and acidic (hydrochloric acid (HCl)) stresses than WT (FIG. 7F).

Because *B. diazoefficiens* is exposed to NCRs in *A. afraspera*, the sensitivity of ΔhpnH to two antimicrobial peptides, polymyxin B [57] and NCR335 from the legume *Medicago truncatula* [58] was also tested. ΔhpnH displayed a 10-fold lower MIC (48 μg/ml) for polymyxin B than WT (512 μg/ml). In addition, ΔhpnH was found to be 100-fold more susceptible than WT to NCR335 (FIG. 7G). ΔhpnP withstood all of the aforementioned stressors as well as the WT, with the exception of acidic stress, where it grew slower than WT.

Example 19: $C_{35}$ Hopanoids are Required to Establish an Efficient Symbiosis with *A. Afraspera* and with Soybean Because hopanoids are required for microaerobic growth and stress tolerance in the free-living state, it is hypothesized that they would aid survival within the plant microenvironment. To test this, the symbiotic phenotypes of ΔhpnP and ΔhpnH on two host plants, soybean and *A. afraspera* were analyzed.

Figure 8:
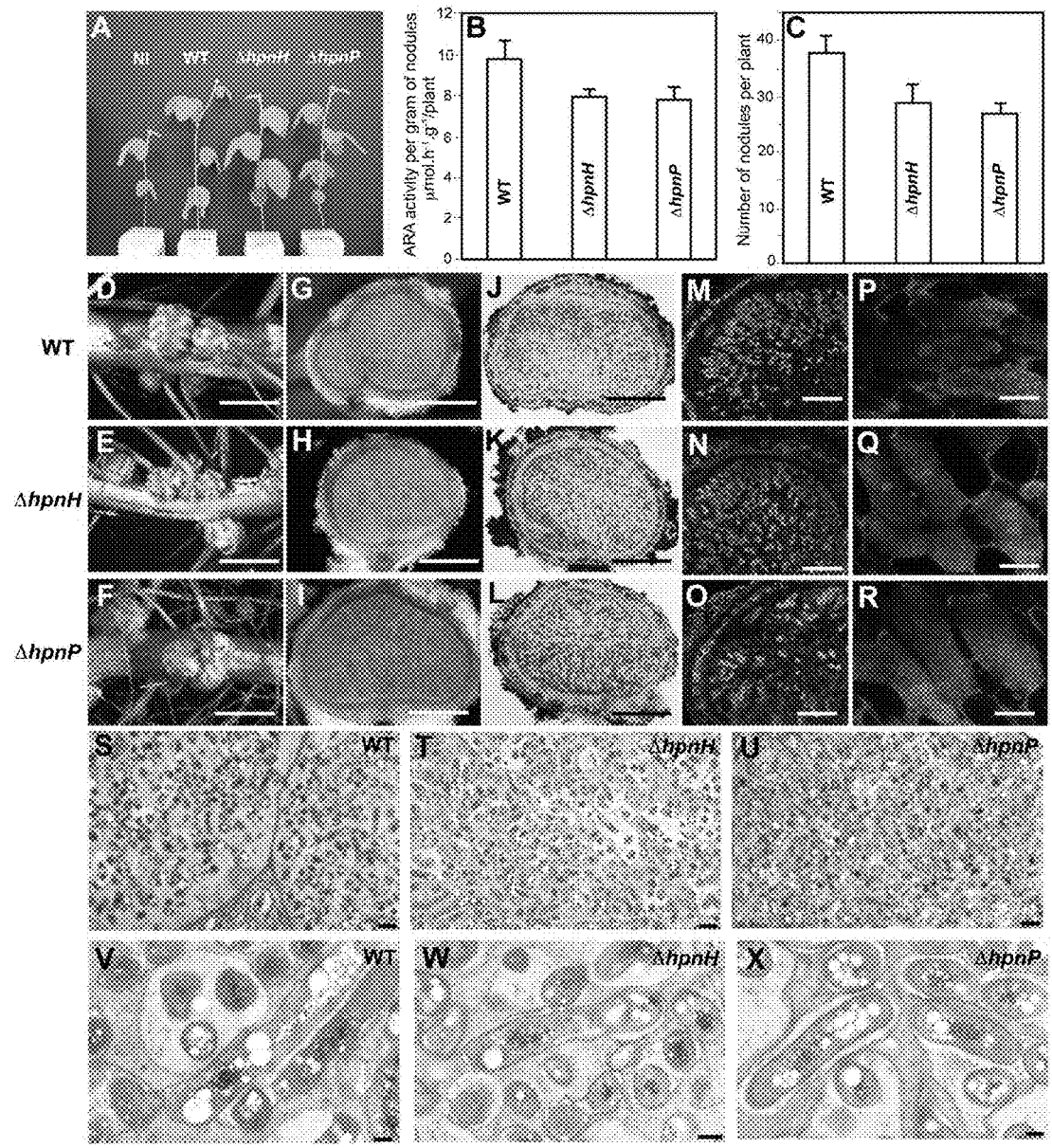
FIG. 8 shows in some embodiments that B. diazoefficiens ΔhpnH mutant is impaired in symbiosis with soybean at 21 d.p.i. Panel A: Comparison of growth of plants, non-inoculated (NI) or inoculated with WT, ΔhpnH and ΔhpnP. Panel B: Quantification of acetylene reduction activity (ARA) in plants inoculated with WT, ΔhpnH and ΔhpnP. Panel C: Nodulation efficiency of WT, ΔhpnH and ΔhpnP on plants. Error bars in B, C represent standard error (n=10). Based on Tukey's HSD test differences between strains were found to be insignificant, p>0.05. Panels D-L: Aspects of nodules elicited by WT (Panels D, G, J), ΔhpnH (Panels E, H, K) and ΔhpnP (Panels F, I, L). (D, E, F) Whole roots, scale=4 mm, (Panels G, H, I) Cross-section of live nodules, scale=1 mm. (Panels J, K, L) Nodule thin sections viewed by brightfield microscopy, scale=1 mm. Panels M-R: Observation of nodules elicited by WT (Panels M, P), ΔhpnH (Panels N, Q) and ΔhpnP (Panels O, R) strains by confocal microscopy using Syto9 (green, healthy bacteroids), calcofluor (blue, plant cell wall) and propidium iodide (red, infected plant nuclei and bacteroids with compromised membranes). Scale=300 μm (M, N, O) 50 μm (Panels P, Q, R). Panels S-X: Transmission electron micrographs of nodules elicited by WT (Panels S, V), ΔhpnH (Panels T, W) and ΔhpnP (Panels U, X). Scale=1 μm (Panels S, T, U), 0.2 μm (Panels V, W, X).

FIG. 8 shows the symbiotic phenotypes of ΔhpnP and ΔhpnH on soybean. On soybean, at 21 days post inoculation (d.p.i.), both mutants induced fewer nodules and displayed reduced nitrogenase activity as estimated by the acetylene reduction assay (ARA) relative to WT (FIG. 8, panels A-C). The ARA data shown in FIG. 8, panel B has a unit of μmol. $h^{-1} \cdot g^{-1}$ per plant as a result of normalization per gram. As further described with respect to FIG. 11, panels (b) and (d), the $N_2$-fixation deficit of ΔhpnH is due to the reduction in nodule mass and the normalization of ARA rates by nodule dry weight eliminates the $N_2$-fixation rate difference between wild type and ΔhpnH (see FIG. 11, panel d, upper graph vs. FIG. 11, panel b, lower-right graph). Therefore, one would expect that if the ARA data of FIG. 8, panel B is not normalized per gram, the differences between the WT and ΔhpnH mutant would be expected to be more statistically significant. Thus, under the conditions of these assays, hpnH mutation appears to have a symbiotic effect on the host plants when *B. diazoefficiens* infects soybean.

Figure 9:
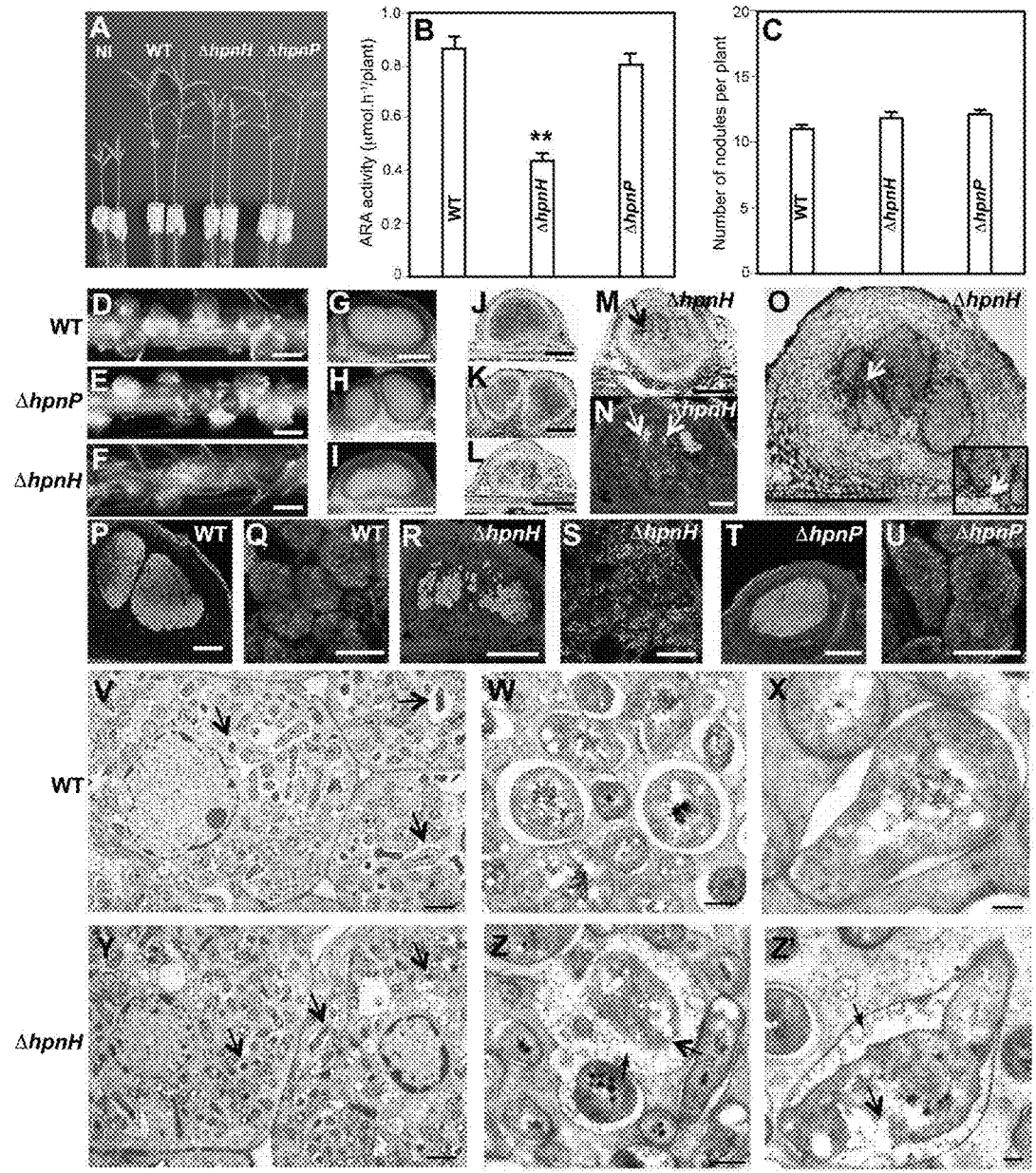
FIG. 9 illustrates in some embodiments that a B. diazoefficiens ΔhpnH mutant is impaired in symbiosis with A. afraspera at 21 d.p.i. Panel A) Comparison of growth of plants, non-inoculated (NI) or inoculated with WT, ΔhpnH and ΔhpnP. Panel B) Quantification of acetylene reduction activity (ARA) in plants inoculated with WT, ΔhpnH and ΔhpnP. Error bars represent standard error (n=10). **$p<0.01$ by Tukey's HSD test. Panel C) Number of nodules per plant elicited by WT, ΔhpnH and ΔhpnP. Panels D-M) Aspect of the nodules elicited by WT (Panels D, G, J), ΔhpnP (Panels E, H, K) and ΔhpnH (Panels F, I, L, M). (D, E, F) Whole roots, scale=1 mm, (Panels G, H, I) Cross-section of live nodules, scale=500 μm. (Panels J, K, L) Nodule thin sections viewed by brightfield microscopy, scale=500 μm. Panel M) The black arrow shows plant defense reactions (necrotic plant cells), scale=500 μm. Panel N) Aspect of the nodules elicited by ΔhpnH as observed by confocal microscopy using the live-dead kit, scale=200 μm. White arrows show plant defense reactions. Panel 0) Aspect of the nodules elicited by ΔhpnH stained with lugol. Scale=500 μm. White arrows show starch granules in dark. Panels P-U) Confocal microscopy observations of nodules elicited by WT (Panels P, Q) ΔhpnH (Panels R, S) and ΔhpnP (Panels T, U) strains and stained using Syto9 (green, healthy bacteroids), calcofluor (blue, plant cell wall) and propidium iodide (red, infected plant nuclei and bacteroids with compromised membranes). Scale=200 μm (P, R, T), 20 μm (Q, S, U). Panels V-Z') TEM of nodules elicited by WT (Panels V, W, X) and ΔhpnH (Panels Y, Z, Z'). Panels V, Y) Black arrows show symbiososmes. Panel Z) Cell envelope of some ΔhpnH bacteroids is not well delineated (bold black arrow) and some deposits of cellular material can be observed in the peribacteroid space (black arrow). Panel Z') The bold black arrow shows bacteroid wall breakdown. The black arrow shows cellular material of unknown origin. Scale=2 μm (V, Y), 0.5 μm (W, Z), 0.2 μM (X, Z').
Figure 10:
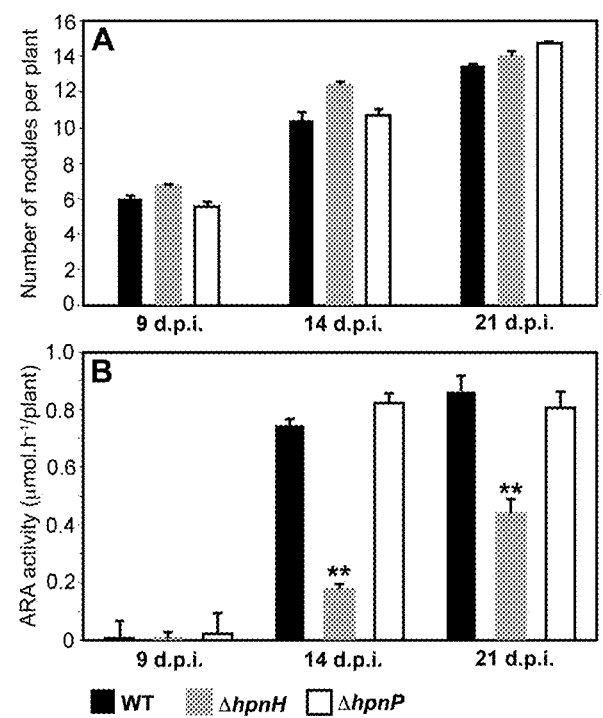
FIG. 10 shows in some embodiments kinetics of nodulation and nitrogen fixation of A. afraspera plants inoculated with B. diazoefficiens. Panel A: Number of nodules elicited by WT, ΔhpnH and ΔhpnP on plants at 9, 14 and 21 days post inoculation (d.p.i.). Panel B: The acetylene-reducing activity (ARA) in plants inoculated with WT, ΔhpnH and ΔhpnP at 9, 14 and 21 d.p.i. Error bars represent standard error (n=10). Asterisk above the error bars indicate significant differences at *$p<0.05$ and **$p<0.01$ (Tukey's HSD test).

FIG. 9 shows the symbiotic phenotypes of ΔhpnP and ΔhpnH on *A. afraspera*. Plants inoculated with ΔhpnH displayed typical nitrogen starvation symptoms, including foliage chlorosis, reduced plant growth and half the ARA activity of WT- and ΔhpnP-infected plants (FIG. 9, panels A, B). Reduced nitrogen fixation was not due to a decrease in the number of nodules, which was comparable in WT- and ΔhpnH-infected plants at 9, 14 and 21 d.p.i., suggesting that the hpnH mutation does not affect nodule organogenesis (FIG. 9, panels C and 10). However, cytological analyses revealed that ΔhpnH nodules displayed several disorders in comparison to WT and ΔhpnP nodules (FIG. 9, panels D-Z').

At the cellular level, ΔhpnH nodules were smaller (FIG. 9, panels D-F) and had pink or, in ~30% of cases, even white central tissue in contrast to WT and ΔhpnP nodules, which were dark pink due to the accumulation of the $O_2$-carrier, leghemoglobin (FIG. 9, panels G-I). The central symbiotic tissue of ΔhpnH nodules was often disorganized and partially infected (FIG. 9, panels L, M, R), as opposed to the fully occupied tissue of WT and ΔhpnP nodules (FIG. 9, panels J, K, P, T). In some ΔhpnH nodules, the presence of necrotic regions—characterized by the accumulation of autofluorescent brown compounds—could be seen (FIG. 9, panels M, N). These are likely polyphenol compounds whose production is associated with plant defense responses [59]. Within ΔhpnH nodules, iodine staining also revealed accumulation of starch granules in the non-infected cells surrounding the symbiotic tissue, whereas such granules were rarely observed in WT and ΔhpnP nodules (FIG. 9O). Starch accumulation is indicative of an imbalance between the photosynthates furnished by the plant and the ability of the bacteria to metabolize them, a typical feature of non-fixing or underperforming strains [60, 61].

To determine whether ΔhpnH symbiotic defects stem from a problem in the bacterial differentiation process or are due to a damaged membrane, nodule sections were examined by confocal microscopy using live-dead staining [62] and TEM to analyze the ultrastructure of bacteroids. Confocal microscopy revealed that all strains, including ΔhpnH, differentiated properly into elongated bacteroids, which were, for the majority, viable, as indicated by the green Syto9 staining (FIG. 9, panels P-U). However, TEM analysis showed that the cell envelope of some ΔhpnH bacteroids was not well delineated and in a few cases, even broken (FIG. 9, panels Y-Z'). Similar damage was seen in the peribacteroid membrane that surrounds bacteroids. Deposits of cellular material, possibly resulting from the release of plant or bacterial cytoplasm, were also observed in the peribacteroid space, suggesting a beginning of senescence or perhaps necrosis of symbiotic bacterial cells (FIG. 9, panels Z, Z'). Such defects were not observed in the WT (FIG. 9, panels V-X) or ΔhpnP nodules.

Taken together, the data indicate that under these conditions $C_{35}$ hopanoids, but not 2Me-hopanoids, play an important role in facilitating the fitness of *B. diazoefficiens* in symbiosis with *A. afraspera* and soybean.

Two reasons the plant host mounts an immune response against ΔhpnH may be that the altered mutant surface layer, as seen in TEM images, is unable to suppress this response [63] and/or the host induces nodule senescence pre-maturely on detecting an under-productive symbiont [64]. Consistent with this, nitrogenase activity is reduced in ΔhpnH relative to WT, a likely consequence of poor cell viability. Similarly, the build-up of plant carbon as starch in ΔhpnH nodules might indicate slow metabolism and/or perturbation of membrane transport processes that facilitate bacteroid carbon acquisition.

Figure 11:
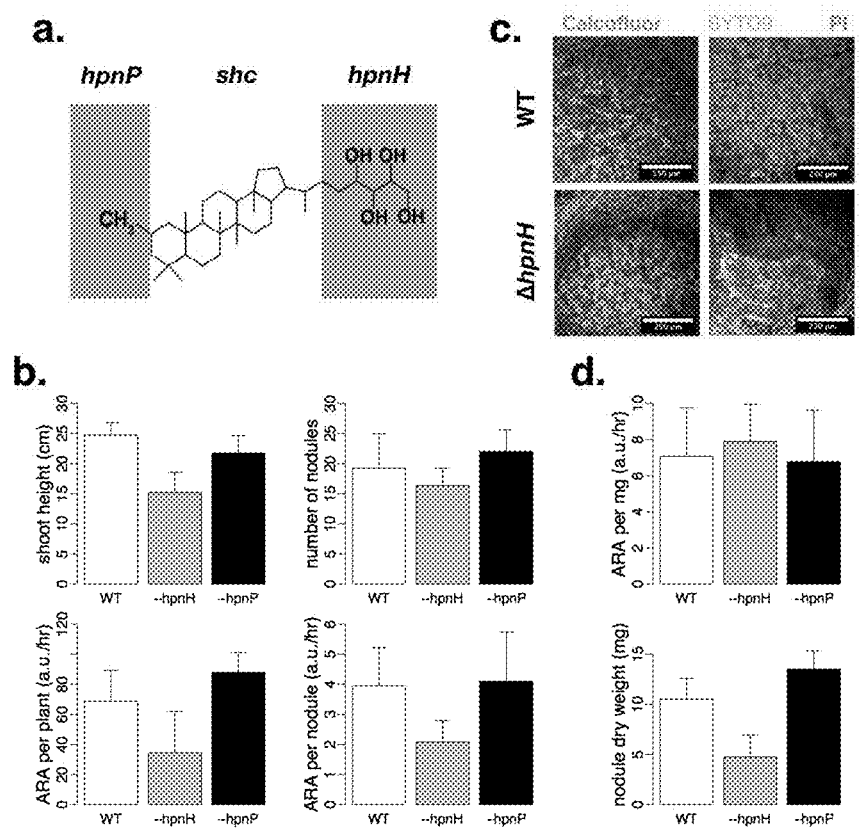
FIG. 11 show, in panel (a), an exemplary structure of the $C_{35}$ hopanoid 2Me-bacteriohopanetetrol (BHT). The gene shc generates the pentacyclic core from squalene; the addition of a methyl group at the $C_2$ position is performed by hpnP; and the addition of a ribose-derived hydrocarbon chain at the $C_{30}$ position to form a $C_{35}$ hopanoid is performed by hpnH. Panel (b) plots acetylene reduction rates for A. afraspera plants at 24 days post-inoculation (dpi) with wild-type (WT), ΔhpnP or ΔhpnH B. diazoefficiens. Panel (c) shows manual cross-sections of root nodules harvested at 24 dpi for wild type and ΔhpnH mutants stained with Calcofluor white, propidium iodide (PI) or SYTO9. Panel (d) shows normalization of acetylene reduction rates by nodule dry weight for wild type and ΔhpnH mutants. All values shown are average values from 10 plants per condition. Error bars represent standard deviation.

Example 20: Assessment of Effects of ΔhpnH in *B. diazoefficiens* on *A. afraspera* Nodules To assess survival rates of WT *B. diazoefficiens* and ΔhpnH mutants of *B. diazoefficiens* within *A. afraspera* root nodules, live cross-sections of WT and ΔhpnH within *A. afraspera* root nodules were stained with SYTO9 (a live cell-permeable DNA dye) and propidium iodide (a live cell-impermeable DNA dye that reports on the fraction of dead cells). Imaging these sections with confocal microscopy revealed that the density and proportion of live bacterial cells is indistinguishable between WT and ΔhpnH nodules as shown in FIG. 11, panel c. Instead, the main difference observed was a reduction in size in ΔhpnH nodules, reducing the number of infected plant cells.

To confirm the observed reduction in size, nodules were harvested from WT- and ΔhpnH-inoculated plants at 24 dpi and their dry weight determined. In particular, to calculate nodule dry weight, all nodules from each plant were harvested by hand, transferred into a pre-weighted Eppendorf tube and dried for 48 hours in a drying oven at 50° C. before weighting.

As shown in FIG. 11, panel (d), lower graph, consistent with the microscopy data, the nodule dry mass per plant was ~50% less for ΔhpnH-inoculated plants. Since the normalization of acetylene reduction rates by nodule dry weight eliminates the $N_2$-fixation rate difference between wild type and ΔhpnH (see FIG. 11, panel d, upper graph), the results suggest that the $N_2$-fixation deficit of ΔhpnH is due to the reduction in nodule mass. The $N_2$-fixation rate per bacterium is likely similar between the two strains. Thus, the primary symbiotic defect in the ΔhpnH mutant observed at 24 dpi appears to be an inhibition of proper root nodule development.

Figure 12:
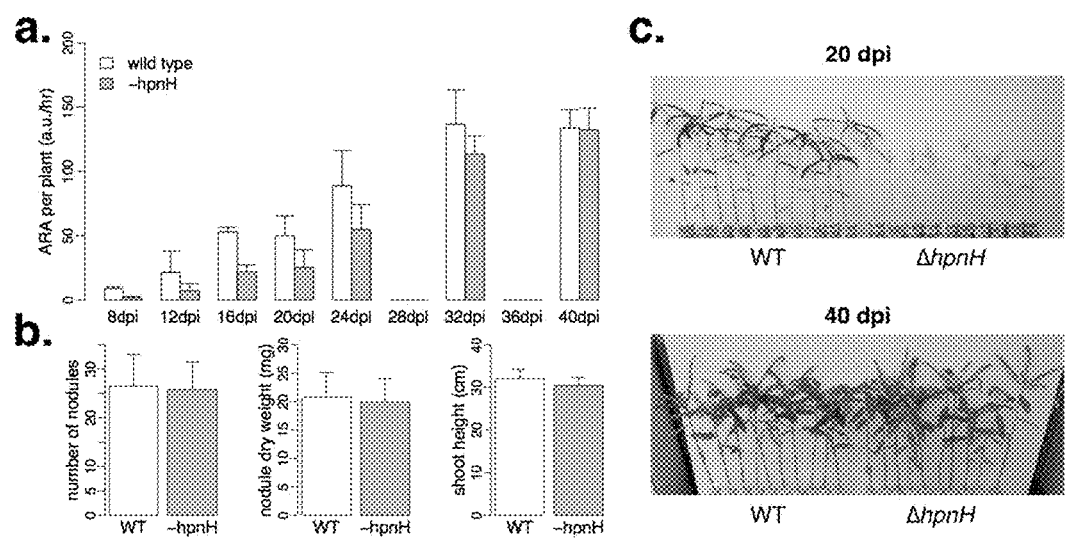
FIG. 12 shows in some embodiments acetylene reduction rates per plant taken every four days after inoculation for WT- and ΔhpnH-inoculated plants (panel a), number of nodules per plant, nodule dry weight per plant and plant shoot heights for WT- and ΔhpnH-inoculated plants (panel b) and images of 10 WT- and ΔhpnH-inoculated plants at 20 dpi and 40 dpi (panel c). All values shown are average values per condition and are pooled from two replicates of four plants each. Error bars represent standard deviation.

To further test how a nodule volume reduction at 24 dpi arises, Acetylene reduction assays were performed every 4 days between 8 dpi and 40 dpi. As shown in FIG. 12, panel a, a total of 36 plants were inoculated for each strain. At each time point, 4 inoculated plants for each strain (and 1 un-inoculated control plant) were chosen randomly for ARA measurements. The experiment was repeated once.

The results shown in FIG. 12, panel b indicate that by 40 dpi, the per-nodule $N_2$-fixation rates, number of nodules per plant, and nodule dry weight per plant are indistinguishable between the strains. These data demonstrate that a developmental arrest in ΔhpnH nodules is not sufficient to explain their low $N_2$-fixation rates.

Example 21: Computational Modeling of Root Nodule Development in *B. diazoefficiens* WT and hpnH Mutant Plants were inoculated as previously described. After 5-7 dpi, 5 plants each for WT and hpnH were removed from their plant culture tubes and transferred to a plastic imaging dish containing pre-warmed, sterile plant medium. Images of plant roots were taken using a Keyence digital microscope and manually aligned. After imaging each plant was returned to its original culture tube and returned to the plant cultivation chamber. Plant roots were imaged every 2-4 days for 40 days; only nodules that were visible within 14 dpi were tracked, due to the increasing likelihood of cross-contamination over time.

Figure 13:
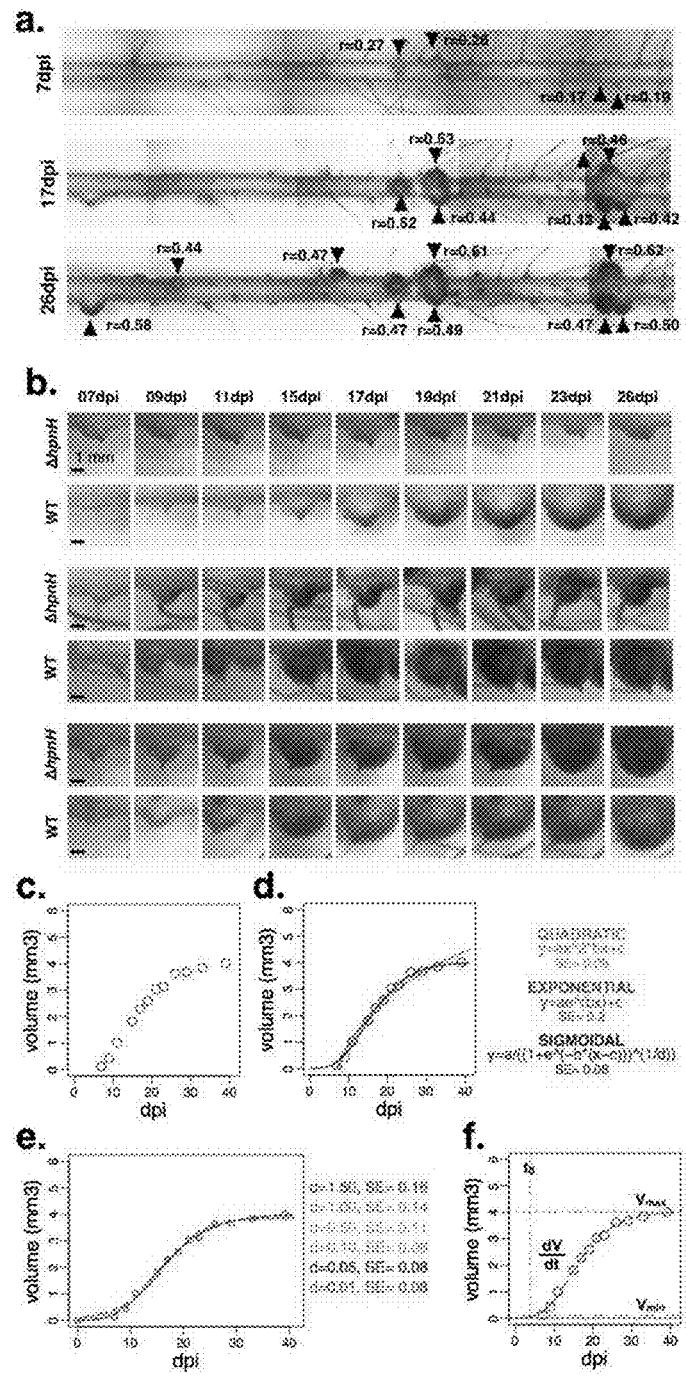
FIG. 13 shows in some embodiments sample tracking of multiple nodules on a single WT plant (with nodule radii) using digital microscopy (panel a); sample nodule growth time series for WT and ΔhpnH plants (panel b), and same nodule growth plot for a WT nodule (panels c-f). In particular, panel c shows the raw data; panel d shows the raw data fit to quadratic, exponential or sigmoidal curves; panel e shows additional parameter fits for the sigmoidal fit; and panel f shows a schematic overview of nodule growth parameters.

For each nodule, the radius was measured and the nodule volumes were estimated by approximating nodules as spheres. FIG. 13, panel a plots raw nodule volumes over time (dpi). Multiple models were tested to identify the function that best fit the nodule growth curves. FIG. 13, panel d plots nodule volumes fit to quadratic, exponential or sigmoidal curves and panel e shows additional parameter fitting for the sigmoidal fit.

The following parameters were extracted from each fitted sigmoidal curve: dV/dt, maximum nodule growth rates; $V_{min}$, the time at which a nodule was visible to the naked eye; $V_{max}$, maximum nodule volumes; and $t_0$, the time of bacterial internalization (an approximation of the nodule initiation time, e.g. when volumes surpassed 0.1 mm³).

Figure 14:
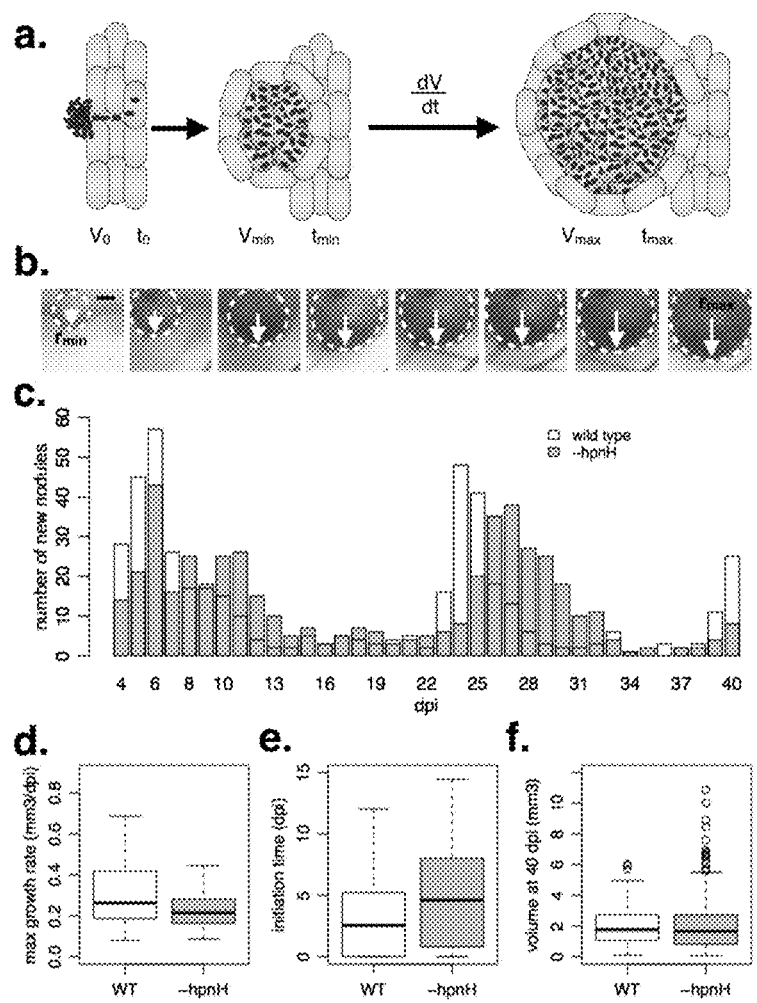
FIG. 14 illustrates a schematic overview of determinate root nodule development in panel a. Parameters describing this process include: $t_0$, the time of bacterial internalization, and $V_0$, the volume of the first infected cell; $t_{min}$, the time at which a nodule is visible by eye, and $V_{min}$, the smallest nodule volume visible by eye; $t_{max}$, the time at which nodule growth has leveled off, and $V_{max}$, the volume of the nodule when nodule growth stops; $dV/dt$, the rate of increase in nodule volume between $t_{min}$ and $t_{max}$. Panel b shows sample wild-type nodule growth time course. Nodule radii are measured directly and the nodule volume is determined by approximation of nodules as spheres. Panel c plots the distribution of newly-emerged nodules over time (in dpi) for wild-type and ΔhpnH nodules from 40 plants each. Panels d, e, and f plot the distributions of $dV/dt$, predicted $t_0$, and $V_{max}$ for wild-type (N~75) and ΔhpnH nodules (N~50).

FIG. 14 shows the results from computational modeling of root nodule development in both *B. diazoefficiens* WT and the hpnH mutant. In particular, panel a illustrates a schematic overview of determinate root nodule development. Parameters describing this process include: $t_0$, the time of bacterial internalization, and $V_0$, the volume of the first infected cell; $t_{min}$, the time at which a nodule is visible by eye, and $V_{min}$, the smallest nodule volume visible by eye; $t_{max}$, the time at which nodule growth has leveled off, and $V_{max}$, the volume of the nodule when nodule growth stops; dV/dt, the rate of increase in nodule volume between $t_{min}$ and $t_{max}$. Panel b shows sample wild-type nodule growth time course. Nodule radii are measured directly and the nodule volume is determined by approximation of nodules as spheres. Panel c plots the distribution of newly-emerged nodules over time (in dpi) for wild-type and hpnH nodules from 40 plants each.

For each nodule, a sigmoidal curve, such as the sigmoidal curve shown in FIG. 13, panel f, was generated, from which dV/dt, $t_0$, and $V_{max}$ were extracted. FIG. 14 Panels d,e,f plot the distributions of dV/dt, predicted $t_0$, and $V_{max}$ for about 75 wild-type nodules and about 50 hpnH nodules.

The results shown in FIG. 14, panels d-f suggest that both reduced nodule growth rates and more variable nodule initiation times occur for ΔhpnH nodules, and preliminary computational simulations suggest they contribute equally to nodule size defects.

Example 22: Polymerase Chain Reaction-Based Cloning of Hopanoid Synthesis Genes

In the following paragraphs, an exemplary procedure is provided that is expected to provide effective genetic modification of rhizobia incapable of producing $C_{35}$ hopanoids ($C_{35}$ hopanoid-deficient rhizobia) is described.

In some cases, genetic modification of $C_{35}$ hopanoid-deficient rhizobia can be performed by polymerase chain reaction-based cloning of $C_{35}$ hopanoid synthesis genes, based on some common approaches described in related literatures such as the method in Welander et al. (2012) [12] which is incorporated herein by reference in its entirety.

Briefly, $C_{35}$ hopanoid synthesis genes including one or more of shc, hpnH, hpnG, hpnO, hpnP, hpnC, hpnD and hpnE shown in FIG. 2, panel B are cloned into a rhizobium expression plasmid vector. A suitable plasmid vector such as those described in Welander et al (2009) [11], Ledermann et al (2015) Mol. Plant Microbe Interact. 28:959, or Vincze and Bowra (2006) [65] are used. For example, a plasmid with broad host range such as pPZP211 was engineered containing a spectinomycin resistance gene, an origin of replication recognized by the recipient rhizobium and *E. coli*, and compatible cloning sites comprising unique restriction endonuclease recognition sites. The cloning site where a $C_{35}$ hopanoid synthesis gene is inserted is downstream of a promoter recognized by the recipient rhizobium, to ensure expression of the $C_{35}$ hopanoid synthesis gene in the recipient rhizobium. Primers used to amplify a $C_{35}$ hopanoid synthesis gene comprise forward and reverse sequences complementary with 5' and 3' ends of a $C_{35}$ hopanoid synthesis gene sequence, flanked by sequences for compatible unique restriction endonuclease recognition sites that are present in the insertion site in the plasmid.

The $C_{35}$ hopanoid producing rhizobium *Bradyrhizobium diazoefficiens* can be used as donor species, from which the hopanoid biosynthesis genes are obtained. Genomic DNA from *Bradyrhizobium diazoefficiens* is isolated using a DNeasy Blood and Tissue Kit (Qiagen). Primers are designed based on the DNA sequences for genes in the hopanoid synthesis gene cluster required to amplify genes required for $C_{35}$ hopanoid biosynthesis, for example hpnH (Genbank locus tag AAV28 RS11540) as shown in Table 2, with the addition of appropriate restriction endonuclease recognition sites at the 5' and 3' ends flanking the gene Hopanoid for example, the C35 hopanoid synthesis gene hpnH is amplified using PCR and the resulting amplicon is analyzed by agarose gel electrophoresis. An amplicon band of the expected size is excised from the gel and purified using the Wizard SV Gel and PCR Clean-Up System (Promega). The purified hpnH amplicon is then cloned into the expression plasmid vector, for example pPZP211 containing an antibiotic resistance gene, for example spectinomycin to permit selection of positive clones, as follows. The plasmid and hpnH amplicon insert are digested with restriction enzymes to create compatible DNA ends for the inserting the hpnH amplicon into the pPZP211 cloning site. For ligation of the insert into the plasmid, the plasmid is mixed with the hpnH insert, ligation buffer and T4 DNA ligase, and incubated at room temperature for 30 minutes. One aliquot of $E.\ coli$ S17-1 competent cells is transformed by electroporation with the ligation mixture, and streaked onto Luria-Bertani (LB) agar plates containing antibiotic, for example spectinomycin. 12-16 hours later, colonies are picked and used to inoculate LB broth cultures containing spectinomycin. After cultures are grown, 1 mL of bacterial culture is used for preparing glycerol stocks, which is stored at −80° C. and used for starting subsequent cultures. The remainder of the transformed $E.\ coli$ S17-1 culture is used for plasmid purification using a QIAprep Spin Miniprep Kit (Qiagen). Integrity of cloned plasmids is assessed using analytical restriction endonuclease digestion and gel electrophoresis. Following identification of positive clones by analytical restriction digest analysis, clones are also analyzed by DNA sequencing, using primers designed to bind to sequences flanking the inserted amplicon in the plasmid.

Example 23: Transfer of a Plasmid Vector Comprising a hpnH Expression Plasmid into a Recipient Rhizobium that Naturally Expresses all Genes Required for C35 Hopanoid Synthesis Except hpnH, by Conjugation with $E.\ coli$ S17-1 Derivatives In one example, transfer of a plasmid vector expressing hpnH into a recipient rhizobium expressing all genes required for C35 hopanoid synthesis except hpnH, is expected to be performed by conjugation with $E.\ coli$ S-17 cells that are transformed with a plasmid vector containing the hopanoid synthesis genes, as follows.

Late log cultures of $E.\ coli$ S17-1 (DKN1) strain (5-10 ml) and a rhizobium recipient strain (10-20 ml) are harvested by centrifugation (10 min, 5000 rpm). The supernatant is discarded and cells are washed with 10-20 ml sterile 0.9% NaCl. The $OD_{600}$ of this solution is measured and cells are again centrifuged. Cells are resuspended in a volume to yield an $OD_{600}$ of approximately 4. 250 µl of $E.\ coli$ donor cells are mixed with 750 µl of a rhizobium recipient strain. The cell mixture is centrifuged (1 min, 13000 rpm, RT) and the supernatant reduced to ~50 µl in which the cells are resuspended. The resuspended cells are transferred as a drop onto a plate containing suitable growth medium, which is dried for approx. 15 min under a laminar flow bench. The plate is incubated for at least two days at 30° C. The cells paste is collected from the plate with a loop, resuspended in 2 ml 0.9% NaCl and appropriate aliquots (e.g. 50, 100, 200 µl) are streaked on selective agar plates containing suitable growth medium and appropriate selection antibiotic. $E.\ coli$ S17-1 donor cells are counter-selected with 20 µg/ml chloramphenicol which does not interfere with growth of the recipient rhizobial cells.

Colonies and grown for 48 h in the presence of appropriate selection antibiotic. Plasmid DNA is isolated from the recipient rhizobium transformants using a Qiagen plasmid preparation kit, following the manufacturer's directions. Plasmids are analyzed using restriction endonuclease digestions and gel electrophoresis and DNA sequencing.

Example 24: Preparation of Transformation-Competent $S.\ meliloti$ Cells

As an alternative to conjugation method in Example 23, transfer of plasmids containing hopanoid synthesis genes into recipient $S.\ meliloti$ cells is expected to be performable using transformation methods. Prior to transformation, $S.\ meliloti$ cells is expected to be treated to become transformation-competent, based on the protocol of Vincze and Bowra (2006) [65] as follows. PSY medium is inoculated with $S.\ meliloti$ and grown at 28° C. with vigorous shaking until it reaches the stationary growth phase.

Two milliliters from the stationary-phase cultures is used to inoculate 50 ml of PSY medium and incubated with shaking for 6 h at 28° C. Cells are harvested by centrifugation at 12,000 g for 10 min at 4° C., and the pellet is resuspended in 2 ml of ice-cold 20 mM $CaCl_2$ solution. The resulting cell suspension is placed into ice-cold 1.5-ml microcentrifuge tubes in aliquots of 100 ul before being snap-frozen in liquid $N_2$. The prepared competent cells are stored at −80° C.

Example 25. Transformation of Competent Recipient $S.\ meliloti$ Cells with Plasmid Vectors Comprising Hopanoid Synthesis Genes Using an Electroporation Method In one example, $S.\ meliloti$ are expected to be transformable with plasmid vectors containing hopanoid synthesis genes using an electroporation method, based on the method of Garg et al (1999) [66].

In particular, recipient $S.\ meliloti$ cells can be grown for 72 h at 30° C. with vigorous shaking to mid-logarithmic phase (absorbance at 600 nm of 0.4 to 0.6). Cells are prepared for electroporation by a modification of the procedure of Dower et al (1988) [67]. Cells can be chilled for 15 to 30 min on ice and then harvested by centrifugation at 9,000 rpm for 10 min at 4° C. The cell pellet is washed four times with cold sterile deionized water and finally washed with 10% glycerol. The cells can be resuspended in 10% glycerol to have an approximate concentration of $10^{10}$ to $10^{11}$ colony-forming units/ml (CFU/ml) and kept on ice. The cell suspension can be distributed in aliquots of 90 µl and mixed thoroughly with plasmid vector containing hopanoid synthesis genes (2 µg) by vortexing at high speed for 10 s and then kept on ice for 30 min. The cell-DNA mixture can be loaded in a chilled electroporation cuvette with a 0.1-cm gap (BTX Inc., San Diego, Calif.) and is subjected to a single pulse of high voltage. For pulse generation, an electrocell manipulator, model 600 (BTX Inc.), may be used that is capable of generating a field strength of up to 25 kV/cm with a 0.1-cm-gap cuvette. After the pulse is delivered, the cuvettes are kept on ice for 10 min. The electroporated cells are suspended in PSY broth and incubated for 24 h at 30° C. The cell suspension is diluted and plated on selective medium containing the appropriate antibiotic.

Colonies from the electrotransformed *S. meliloti* can be selected and grown for 48 h in the presence of appropriate selection antibiotic. Plasmid DNA is isolated from the *S. meliloti* transformants using a Qiagen plasmid preparation kit, following the manufacturer's directions. Plasmids are analyzed using restriction endonuclease digestions and gel electrophoresis and DNA sequencing.

Example 26: Transformation of Competent Recipient *S. meliloti* Cells with Plasmid Vectors Comprising Hopanoid Synthesis Genes Using a Freeze-Thaw Method In one example, transformation of competent *S. meliloti* cells with plasmid vectors containing hopanoid synthesis genes is expected to be performable following a "freeze-thaw" method based on that of Vincze and Bowra (2006) [65]. Approximately 1 ug of a vector plasmid containing cloned hopanoid synthesis genes, can be made up to a volume of 5 ul with sterile distilled water. This can be then added to a 100 ul aliquot of competent cells immediately after they are removed from −80° C. Subsequently, the mixture is kept at 37° C. for 5 min without shaking. For the recovery phase, 1 ml of the appropriate medium is added to the transformed cells before they are transferred to 10-ml tubes and incubated at 28° C. for 2 h with shaking. To determine the actual transformation efficiency, the cell suspension is diluted and plated on nonselective agar medium to count the cells. Cells without added DNA and the appropriately diluted transformation mixture are plated on selective medium to calculate the number of spontaneous resistant colonies and transformation efficiency, respectively.

Similar to the results of Vincze and Bowra (2006), it is expected that a 6-h growth period for competent-cell preparation will be sufficient to produce transformants of fast-growing species of *Sinorhizobium*. The *S. meliloti* transformants are checked for the presence of the introduced plasmid comprising cloned hopanoid synthesis genes. Colonies from the transformed *S. meliloti* are selected and grown for 48 h in the presence of appropriate selection antibiotic. Plasmid DNA is isolated from the *S. meliloti* transformants using a Qiagen plasmid preparation kit, following the manufacturer's directions. Plasmids are analyzed using restriction endonuclease digestions and gel electrophoresis and DNA sequencing Example 27: Transformation of Competent Recipient *S. meliloti* Cells with Plasmid Vectors Comprising Hopanoid Synthesis Genes Using a Thermal Shock Method In one embodiment, transformation of *S. meliloti* with plasmid vectors containing hopanoid synthesis genes is expected to be performable by a "thermal shock" method, based on a protocol by Courtois et al. (1988) [68], as follows.

The recipient *S. meliloti* is grown up in the appropriate medium in a rotary bath shaker (60 revolutions per min) at 30° C. to a density of $10^8$ CFU/ml, and it maintained static at 30° C. After 3 h of incubation, the cells are harvested by centrifugation at 3,000×g for 10 min and suspended in the appropriate medium to give a cell density of $10^9$ CFU/ml.

A 0.2-ml portion of this suspension can be added to 0.1 ml of vector plasmid containing hopanoid synthesis genes dissolved in 0.15 M NaCl (pH 7). The mixture is chilled rapidly at 0° C. After 15 min at 0° C., it is transferred for 5 min at 37° C. then at 0° C. After 40 min, the mixture is incubated for 30 min in a 30° C. water bath. Then, to allow phenotypic expression of the drug markers, the cells are diluted in appropriate medium and streaked on selective agar plates containing appropriate medium and antibiotic. After 4 days of incubation at 30° C., *S. meliloti* transformant colonies are analyzed for the presence of the plasmid vector.

Colonies from the different electrotransformed *S. meliloti* can be selected and grown for 48 h in the presence of appropriate selection antibiotic. Plasmid DNA is isolated from the *S. meliloti* transformants using a Qiagen plasmid preparation kit, following the manufacturer's directions. Plasmids are analyzed using restriction endonuclease digestions and gel electrophoresis and DNA sequencing Example 28: Assessment of the Ability of *S. meliloti* Harboring Plasmid Vectors Containing Hopanoid Synthesis Genes to Form Nodules In one embodiment, assessment of the ability of genetically modified *S. meliloti* harboring plasmid vectors containing hopanoid synthesis genes to form nodules is expected to be based on the method of Vincze and Bowra (2016) [65].

It is expected that the presence of the plasmid vector will not prevent the transformed *S. meliloti* from forming effective nodules on legumes. To confirm the stability of the plasmid in the *S. meliloti* during nodulation, bacteria and bacteroids are isolated from nodules 4 weeks after inoculation and are characterized, as follows. The bacteria are isolated on nonselective medium from the surface-sterilized nodules. The colonies are tested for antibiotic resistance on selective plates, and the restriction endonuclease digest pattern of the purified plasmid was analyzed by gel electrophoresis. It is expected that no loss of antibiotic resistance is observed, and the *S. meliloti* isolated from the nodules harbors the plasmid vector containing the hopanoid sysnthesis genes.

Example 29: Analysis of $C_{35}$ Hopanoid Production in Rhizobia

In some cases, screening of rhizobia for the production of $C_{35}$ hopanoids is expected to be performed using analysis of lipids extracted from cultured rhizobia for the presence of C35 hopanoids, based on some common approaches described in related literatures such as the method in Welander et al. (2012) [12], which is incorporated herein by reference in its entirety.

Briefly, rhizobial cells can be grown in YPS medium under aerobic conditions at 30° C. to stationary phase (3 days). Cells are harvested by centrifugation at 4° C. and lipids are extracted by sonication the cells for 15 minutes at room temperature in 10 ml of 10:5:4 (v:v:v) methanol (MeOH): dichloromethane (DCM):water. Samples are centrifuged for 10 minutes at 3000×g and the supernatant is transferred to a new tube. Cell pellets are sonicated again in 10 ml of MeOH:DCM:water (10:5:4, v/v/v), centrifuged, and the supernatant combined with the first extraction.

The samples can be separated into two phases by adding 20 ml 1:1 (v/v) DCM:water, centrifuged for 10 minutes at 3000×g, and the organic phase is transferred to a new vial. To the remaining aqueous phase, 10 ml of DCM:water (1:1, v/v) is added again, centrifuged, and the organic phase was combined with the previous extract. The organic solvents are evaporated under N2 and the total lipid extract (TLE) is redissolved in 2 ml DCM. The TLE is divided into two 1 ml aliquots. One aliquot is separated by chromatography on a silica gel column. Six fractions are eluted: F1: hexane; F2: hexane:DCM (4:1, v/v); F3: DCM; F4: DCM:ethyl acetate (EtOAC) (4:1, v/v); F5: EtOAc; F6: MeOH. Separation of the TLE facilitated the detection of diplopterol in fraction 4. Fractions 4, 5, 6 and the remaining TLEs are incubated in 100 µl of acetic anhydride:pyridine (1:1, v/v) for 1 hour at 70° C. to derivatize alcohols into acetate esters. The hydrocarbon fractions (F1 and F2), the acetylated fractions (F4, F5, and F6), and the acetylated TLEs are analyzed by high temperature gas chromatography-mass spectrometry (GC-MS) as previously described (Welander et al., 2009) [11].

The acetylated TLEs can be also analyzed by liquid chromatography-mass spectrometry (LC-MS). A Poroshell 120 EC-C18 column (2.1×150 mm, 2.7 µm; Agilent Technologies), set at 30° C., is eluted isocratically first with MeOH/water (95:5, v:v) for 2 min at a flow rate of 0.15 ml/min, then using a linear gradient up to 20% (v) of isopropyl alcohol (IPA) over 18 min at a flow rate of 0.19 ml/min, and isocratic for 10 min. The linear gradient is then set to 30% (v) of IPA at 0.19 ml/min over 10 min, and maintained for 5 min. The column is subsequently eluted using a linear gradient up to 80% IPA (v) over 1 min at a flow rate of 0.15 ml/min and isocratic for 14 min. Finally the column was eluted with MeOH/water (95:5, v:v) at 0.15 ml/min for 5 min. The APCI parameters were as follows: gas temperature 325° C., vaporizer temperature 350° C., drying gas (N2) flow 6 l/min, nebulizer (N2) flow 30 l/min, capillary voltage 1200 V, corona needle 4 µA, fragmentor 150 V. Data are recorded by scanning from m/z 100 to 1600. Identification of the hopanoids is done using their exact mass and by comparison of the retention time and the mass spectra with published data (Talbot et al., 2007; Talbot et al., 2003b) [69, 70].

Example 30: Genetic Screen of Stress-Resistant Rhizobia as a Biofertilizer

Screening of rhizobia for the production of $C_{35}$ hopanoids is expected to be performed by using a method of performing a diagnostic screen for the presence of $C_{35}$ hopanoid synthesis. Oligonucleotide primers are designed to amplify sequences of genes for $C_{35}$ hopanoid synthesis, based on the DNA sequences of of the genes.

Briefly, genomic DNA can be isolated from rhizobia and diagnostic PCR is performed using primers to amplify $C_{35}$ hopanoid synthesis genes. The resulting amplicons are analyzed by gel electrophoresis to confirm expected DNA band molecular weight. In addition, DNA sequencing is performed on genomic DNA samples to confirm the presence of hopanoid synthesis genes.

The diagnostic PCR and DNA sequencing can determine whether $C_{35}$ hopanoid synthesis genes are present in the genome of a rhizobium sample, and therefore whether the rhizobium is capable of synthesizing $C_{35}$ hopanoids, and thus to be used as biofertilizer with enhanced stress-resistance properties.

The examples set forth above are provided to give those of ordinary skill in the art a complete disclosure and description of how to make and use the embodiments of the compositions, microorganisms, systems and methods of the disclosure, and are not intended to limit the scope of what the inventors regard as their disclosure. Those skilled in the art will recognize how to adapt the features of the exemplified hopanoids, hopanoids-producing nitrogen-fixing bacteria, leguminous plants and related formulation and uses to others according to various embodiments and scope of the claims.

The examples set forth above are provided to give those of ordinary skill in the art a complete disclosure and description of how to make and use the embodiments of the compositions, microorganisms, systems and methods of the disclosure, and are not intended to limit the scope of what the inventors regard as their disclosure. Those skilled in the art will recognize how to adapt the features of the exemplified hopanoids, hopanoids-producing nitrogen-fixing bacteria, leguminous plants and related formulation and uses to others according to various embodiments and scope of the claims.

All patents and publications mentioned in the specification are indicative of the levels of skill of those skilled in the art to which the disclosure pertains.

The entire disclosure of each document cited (including patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence. Further, the computer readable form of the sequence listing of the ASCII text file P1953-US-Seq-List-ST25 is incorporated herein by reference in its entirety.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified may be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein may be excluded from a claim of this disclosure. The disclosure illustratively described herein suitably may be practiced in the absence of any element or elements, limitation or limitations which is not specifically disclosed herein.

A number of embodiments of the disclosure have been described. The specific embodiments provided herein are examples of useful embodiments of the invention and it will be apparent to one skilled in the art that the disclosure can be carried out using a large number of variations of the devices, device components, methods steps set forth in the present description. As will be obvious to one of skill in the art, methods and devices useful for the present methods may include a large number of optional composition and processing elements and steps.

In particular, it will be understood that various modifications may be made without departing from the spirit and scope of the present disclosure. Accordingly, other embodiments are within the scope of the following claims.

REFERENCES

1. Gibson, K. E., H. Kobayashi, and G. C. Walker, *Molecular determinants of a symbiotic chronic infection*. Annu Rev Genet, 2008. 42: p. 413-41.
2. Oldroyd, G. E., et al., *The rules of engagement in the legume-rhizobial symbiosis*. Annu Rev Genet, 2011. 45: p. 119-44.
3. Rohmer, M., *The Biosynthesis of Triterpenoids of the Hopane Series in the Eubacteria—a Mine of New Enzyme-Reactions*. Pure and Applied Chemistry, 1993. 65(6): p. 1293-1298.
4. Ricci, J. N., et al., *Diverse capacity for 2-methylhopanoid production correlates with a specific ecological niche*. ISME J, 2014. 8(3): p. 675-84.
5. Kannenberg, E. L., M. Perzl, and T. Hartner, *The Occurrence of Hopanoid Lipids in Bradyrhizobium Bacteria*. Fems Microbiology Letters, 1995. 127(3): p. 255-261.
6. Nalin, R., et al., *High hopanoid/total lipids ratio in Frankia mycelia is not related to the nitrogen status*. Microbiology, 2000. 146 (Pt 11): p. 3013-9.
7. Silipo, A., et al., *Covalently linked hopanoid-lipid A improves outer-membrane resistance of a Bradyrhizobium symbiont of legumes*. Nat Commun, 2014. 5: p. 5106.
8. Wu, C. H., M. Bialecka-Fornal, and D. K. Newman, *Methylation at the C-2 position of hopanoids increases rigidity in native bacterial membranes*. Elife, 2015. 4.
9. Kulkarni, G., C. H. Wu, and D. K. Newman, *The general stress response factor EcfG regulates expression of the C-2 hopanoid methylase HpnP in Rhodopseudomonas palustris TIE-1*. J Bacteriol, 2013. 195(11): p. 2490-8.
10. Schmerk, C. L., et al., *Elucidation of the Burkholderia cenocepacia hopanoid biosynthesis pathway uncovers functions for conserved proteins in hopanoid-producing bacteria*. Environ Microbiol, 2015. 17(3): p. 735-50.
11. Welander, P. V., et al., *Hopanoids play a role in membrane integrity and pH homeostasis in Rhodopseudomonas palustris TIE-1*. J Bacteriol, 2009. 191(19): p. 6145-56.
12. Welander, P. V., et al., *Identification and characterization of Rhodopseudomonas palustris TIE-1 hopanoid biosynthesis mutants*. Geobiology, 2012. 10(2): p. 163-77.
13. Welander, P. V. and R. E. Summons, *Discovery, taxonomic distribution, and phenotypic characterization of a gene required for 3-methylhopanoid production*. Proc Natl Acad Sci USA, 2012. 109(32): p. 12905-10.
14. J. N. RICCI, A.J.M.A.D.K.N., *Phylogenetic analysis of HpnP reveals the origin of 2-methylhopanoid production in Alphaproteobacteria*. Geobiology, 2015. 13: p. 11.
15. Altschul S F, M. T., Schïffer A A, Zhang J, Zhang Z, Miller W, Lipman D J., *Gapped BLAST and PSI-BLASTa new generation of protein database search programs*. Nucleic Acids Res., 1997. 25(17): p. 14.
16. Smith T F, W. M., *Identification of common molecular subsequences*. J Mol Biol, 1981. 147(1): p. 3.
17. W R, P., *Searching protein sequence libraries: comparison of the sensitivity and selectivity of the Smith-Waterman and FASTA algorithms*. Genomics, 1991. 11(3): p. 16.
18. Pearson W R, L. D., *Improved tools for biological sequence comparison*. Proc Natl Acad Sci USA, 1988. 85(8): p. 5.
19. Johnson L S, E. S., Portugaly E, *Hidden Markov model speed heuristic and iterative HMM search procedure*. BMC Bioinformatics, 2010. 11(431): p. 8.
20. Masson-Boivin, C., et al., *Establishing nitrogen-fixing symbiosis with legumes: how many rhizobium recipes?* Trends Microbiol, 2009. 17(10): p. 458-66.
21. Renier, A., et al., *Photosynthetic Bradyrhizobium Sp. strain ORS285 synthesizes 2-O-methylfucosylated lipochitooligosaccharides for nod gene-dependent interaction with Aeschynomene plants*. Mol Plant Microbe Interact, 2011. 24(12): p. 1440-7.
22. Prell, J. and P. Poole, *Metabolic changes of rhizobia in legume nodules*. Trends Microbiol, 2006. 14(4): p. 161-8.
23. Fleischman, D. and D. Kramer, *Photosynthetic rhizobia*. Biochimica Et Biophysica Acta-Bioenergetics, 1998. 1364(1): p. 17-36.
24. Kaneko, T., et al., *Complete genomic sequence of nitrogen-fixing symbiotic bacterium Bradyrhizobium japonicum USDA110*. DNA Res, 2002. 9(6): p. 189-97.
25. Giraud, E., et al., *Legumes symbioses: absence of Nod genes in photosynthetic bradyrhizobia*. Science, 2007. 316(5829): p. 1307-12.
26. Neubauer, C., et al., *Lipid remodeling in Rhodopseudomonas palustris TIE-1 upon loss of hopanoids and hopanoid methylation*. Geobiology, 2015.
27. Bligh E G, D. W., *A rapid method of total lipid extraction and purification*. Can J Biochem Physiol., 1959. 37(8): p. 7.
28. Wu C H, K. L., Bialecka-Fornal M, Park S, Thompson A L, Kulkarni G, Conway S J, Newman D K, *Quantitative hopanoid analysis enables robust pattern detection and comparison between laboratories*. Geobiology, 2015. 13(4): p. 17.
29. Kreshech, G. C., *Surfactants in Water—A Comprehensive Treatise*. 1975: Plenum, N.Y.
30. Komaniecka, I., et al., *Occurrence of an unusual hopanoid-containing lipid A among lipopolysaccharides from Bradyrhizobium species*. J Biol Chem, 2014. 289 (51): p. 35644-55.
31. Bravo, J. M., et al., *Novel methylated triterpenoids of the gammacerane series from the nitrogen-fixing bacterium Bradyrhizobium japonicum USDA 110*. Eur J Biochem, 2001. 268(5): p. 1323-31.
32. Hauser, F., et al., *Design and validation of a partial-genome microarray for transcriptional profiling of the Bradyrhizobium japonicum symbiotic gene region*. Mol Genet Genomics, 2006. 275(1): p. 55-67.

33. Markowitz, V. M. and N. C. Kyrpides, *Comparative genome analysis in the integrated microbial genomes (IMG) system*. Methods Mol Biol, 2007. 395: p. 35-56.
34. Casadaban, M. J. and S. N. Cohen, Analysis of Gene-Control Signals by DNA-Fusion and Cloning in *Escherichia-Coli*. Journal of Molecular Biology, 1980. 138(2): p. 179-207.
35. Simon, R., U. Priefer, and A. Puhler, *A Broad Host Range Mobilization System for Invivo Genetic-Engineering—Transposon Mutagenesis in Gram-Negative Bacteria*. Bio-Technology, 1983. 1(9): p. 784-791.
36. Regensburger, B. and H. Hennecke, *Rna-Polymerase from Rhizobium-Japonicum*. Archives of Microbiology, 1983. 135(2): p. 103-109.
37. Schafer, A., et al., *Small mobilizable multi-purpose cloning vectors derived from the Escherichia coli plasmids pK18 and pK19: selection of defined deletions in the chromosome of Corynebacterium glutamicum*. Gene, 1994. 145(1): p. 69-73.
38. Fischer, H. M., et al., *One member of a gro-ESL-like chaperonin multigene family in Bradyrhizobium japonicum is co-regulated with symbiotic nitrogen fixation genes*. EMBO J, 1993. 12(7): p. 2901-12.
39. Lindemann, A., et al., *Host-specific symbiotic requirement of BdeAB, a RegR-controlled RND-type efflux system in Bradyrhizobium japonicum*. FEMS Microbiol Lett, 2010. 312(2): p. 184-91.
40. Wu, C. H., et al., *Quantitative hopanoid analysis enables robust pattern detection and comparison between laboratories*. Geobiology, 2015.
41. Sessions, A. L., et al., *Identification and quantification of polyfunctionalized hopanoids by high temperature gas chromatography-mass spectrometry*. Org Geochem, 2013. 56: p. 120-130.
42. Westphal, O.a.J., J. K., *Bacterial lipopolysaccharide extraction with water-phenol and further applications of the procedure*. Methods Carbohydr Chem, 1965. 43: p. 83-91.
43. Leontein, K., B. Lindberg, and J. Lonngren, *Assignment of Absolute-Configuration of Sugars by Gic of Their Acelylated Glycosides Formed from Chiral Alcohols*. Carbohydrate Research, 1978. 62(2): p. 359-362.
44. Hakomori, S. I., *Rapid Permethylation of Glycolipid+ Polysaccharide Catalyzed by Methylsulfinyl Carbanion in Dimethyl Sulfoxide*. Journal of Biochemistry, 1964. 55(2): p. 205-&.
45. Rietschel, E. T., *Absolute configuration of 3-hydroxy fatty acids present in lipopolysaccharides from various bacterial groups*. Eur J Biochem, 1976. 64(2): p. 423-8.
46. Que, N. L. S., et al., *Purification and mass spectrometry of six lipid A species from the bacterial endosymbiont Rhizobium etli—Demonstration of a conserved distal unit and a variable proximal portion*. Journal of Biological Chemistry, 2000. 275(36): p. 28006-28016.
47. Dobro, M. J., et al., *Plunge Freezing for Electron Cryomicroscopy*. Methods in Enzymology, Vol 481: Cryo-Em, Part a—Sample Preparation and Data Collection, 2010. 481: p. 63-82.
48. Iancu, C. V., et al., *Electron cryotomography sample preparation using the Vitrobot*. Nat Protoc, 2006. 1(6): p. 2813-9.
49. Chen, S., et al., *Electron cryotomography of bacterial cells*. J Vis Exp, 2010(39).
50. Jensen, G. J., *Cryo-EM, Part A: Sample Prepration and Data Collection*. Methods Enzymol, 2010. 481: p. 2-410.
51. Ehrhardt, D. W., E. M. Atkinson, and S. R. Long, *Depolarization of alfalfa root hair membrane potential by Rhizobium meliloti Nod factors*. Science, 1992. 256 (5059): p. 998-1000.
52. Bonaldi, K., et al., *The Nod factor-independent symbiotic signaling pathway: development of Agrobacterium rhizogenes-mediated transformation for the legume Aeschynomene indica*. Mol Plant Microbe Interact, 2010. 23(12): p. 1537-44.
53. Nagata, T. and I. Takebe, *Cell wall regeneration and cell division in isolated tobacco mesophyll protoplasts*. Planta, 1970. 92(4): p. 301-8.
54. Masloboeva, N., et al., *Reactive oxygen species-inducible ECF sigma factors of Bradyrhizobium japonicum*. PLoS One, 2012. 7(8): p. e43421.
55. Welander, P. V., et al., *Identification of a methylase required for 2-methylhopanoid production and implications for the interpretation of sedimentary hopanes*. Proc Natl Acad Sci USA, 2010. 107(19): p. 8537-42.
56. Czernic, P., et al., *Convergent Evolution of Endosymbiont Differentiation in Dalbergioid and IRLC Legumes Mediated by Nodule-Specific Cysteine-Rich Peptides*. Plant Physiol, 2015.
57. Newton, B. A., *Properties and Mode of Action of the Polymyxins*. Bacteriological Reviews, 1956. 20(1): p. 14-27.
58. Tiricz, H., et al., *Antimicrobial nodule-specific cysteine-rich peptides induce membrane depolarization-associated changes in the transcriptome of Sinorhizobium meliloti*. Appl Environ Microbiol, 2013. 79(21): p. 6737-46.
59. Vasse, J., F. Debilly, and G. Truchet, *Abortion of Infection during the Rhizobium-Meliloti-Alfalfa Symbiotic Interaction Is Accompanied by a Hypersensitive Reaction*. Plant Journal, 1993. 4(3): p. 555-566.
60. Finan, T. M., J. M. Wood, and D. C. Jordan, Symbiotic Properties of C4-Dicarboxylic Acid Transport Mutants of *Rhizobium-Leguminosarum*. Journal of Bacteriology, 1983. 154(3): p. 1403-1413.
61. Lodwig, E. M., et al., *Amino-acid cycling drives nitrogen fixation in the legume-Rhizobium symbiosis*. Nature, 2003. 422(6933): p. 722-6.
62. Haag, A. F., et al., *Protection of Sinorhizobium against host cysteine-rich antimicrobial peptides is critical for symbiosis*. PLoS Biol, 2011. 9(10): p. e1001169.
63. Kannenberg, E. L. and R. W. Carlson, *Lipid A and O-chain modifications cause Rhizobium lipopolysaccharides to become hydrophobic during bacteroid development*. Mol Microbiol, 2001. 39(2): p. 379-91.
64. West, S. A., et al., *Sanctions and mutualism stability: why do rhizobia fix nitrogen?* Proc Biol Sci, 2002. 269 (1492): p. 685-94.
65. Vincze E, B. S., *Transformation of Rhizobia with broad host range plasmids using Freeze-thaw method*. Appl Environ Microbiol., 2006. 72: p. 4.
66. Garg, B., R. C. Dogra, and P. K. Sharma., *High-efficiency transformation of Rhizobium leguminosarum by electroporation*. Appl. Environ. Microbiol., 1999. 65: p. 3.
67. Dower W J, M. J., Ragsdale C W., *High efficiency transformation of E. coli by high voltage electroporation*. Nucleic Acids Res., 1988. 16: p. 19.
68. Courtois J, C. B.a.G. J., *High frequency transformation of Rhizobium meliloti*. J. Bacteriol., 1988. 170(12): p. 3.
69. Talbot H M, R. M., Farrimond P., *Structural characterisation of unsaturated bacterial hopanoids by atmospheric pressure chemical ionisation liquid chromatography/ion trap mass spectrometry*. Rapid Communications in Mass Spectrometry., 2007. 21: p. 10.
70. Talbot H M, S. R., Jahnke L, Farrimond P., *Characteristic fragmentation of bacteriohopanepolyols during atmospheric pressure chemical ionisation liquid chromatography/ion trap mass spectrometry*. Rapid Communications in Mass Spectrometry, 2003. 17: p. 9.

The invention claimed is:

1. A biofertilizer for a leguminous plant essentially consisting of one or more nitrogen-fixing rhizobia naturally incapable of producing $C_{35}$ hopanoids and genetically engineered to include a set of genes of a nitrogen-fixing rhizobia naturally capable of producing $C_{35}$ hopanoids, enabling production of $C_{35}$ hopanoids by the one or more nitrogen-fixing rhizobia naturally incapable of producing $C_{35}$ hopanoids, in a form suitable for administration to one or more leguminous plant or seed, and/or for administration to a soil surrounding the one or more leguminous plant or seed, wherein the set of genes comprises she gene encoding a squalene-hopene cyclase, hpnH gene encoding a B12 binding radical SAM, and gene hpnG encoding for a nucleosidase.

2. The biofertilizer of claim 1, the biofertilizer is in combination with suitable carrier allowing increased stability, viability and/or effectiveness of gas exchange of the one or more nitrogen-fixing rhizobia.

3. The biofertilizer of claim 1, wherein the one or more nitrogen-fixing rhizobia naturally incapable of producing $C_{35}$ hopanoids comprise at least one selected from the group consisting of *Rhizobium etli, Rhizobium leguminosarum, Mesorhizobium loti, Sinorhizobium meliloti, Azorhizobium caulinodans*, and *Ochrobactrum anthropi.*

4. A method to provide biofertilizer for a leguminous plant of claim 1, the method comprising genetically engineering a nitrogen-fixing rhizobia strain incapable of producing $C_{35}$ hopanoids to introduce $C_{35}$ synthesis genes of a nitrogen-fixing rhizobia naturally capable of producing $C_{35}$ hopanoids comprising squalene-hopene cyclase she gene, B12 binding radical SAM hpnH gene, and nucleosidase hpnG gene, thus providing a genetically engineered nitrogen-fixing rhizobia strain capable of producing $C_{35}$ hopanoids; and providing the genetically engineered nitrogen-fixing rhizobia strains in a form suitable for administration to a leguminous plant or seed, and/or a soil surrounding leguminous plant or seed thus providing the biofertilizer for the leguminous plant.

5. A biofertilizer composition for a leguminous plant, the biofertilizer composition comprising one or more biofertilizers essentially consisting of one or more genetically engineered nitrogen-fixing rhizobia capable of producing $C_{35}$ hopanoids of claim 1 together with an acceptable vehicle.

6. The biofertilizer of claim 5, wherein the acceptable vehicle is a carrier allowing increased stability, viability and/or effectiveness of the nitrogen-fixing bacteria gas exchange of the one or more nitrogen-fixing rhizobia.

7. The biofertilizer composition of claim 5, wherein the one or more nitrogen-fixing bacteria further comprise at least one *Bradyrhizobium*.

8. The biofertilizer composition of claim 5, wherein the one or more nitrogen-fixing bacteria naturally incapable of producing $C_{35}$ hopanoids comprise at least one selected from the group consisting of *Rhizobium etli, Rhizobium leguminosarum, Mesorhizobium loti, Sinorhizobium meliloti, Azorhizobium caulinodans*, and *Ochrobactrum anthropic.*

9. The biofertilizer composition of claim 5, wherein the vehicle is a carrier selected from the group consisting of peat, vermiculite, lignite powder, clay, talc, rice bran, seed, rock phosphate pellet, charcoal, soil, paddy straw compost, wheat bran, gum Arabic, methylethylcellulose, sucrose solutions, vegetable oils and a mixture thereof.

10. The biofertilizer composition of claim 5, further comprising one or more $C_{35}$ hopanoids.

11. The biofertilizer composition of claim 10, wherein the one or more $C_{35}$ hopanoids comprise the one or more $C_{35}$ hopanoids having a formula of (I)

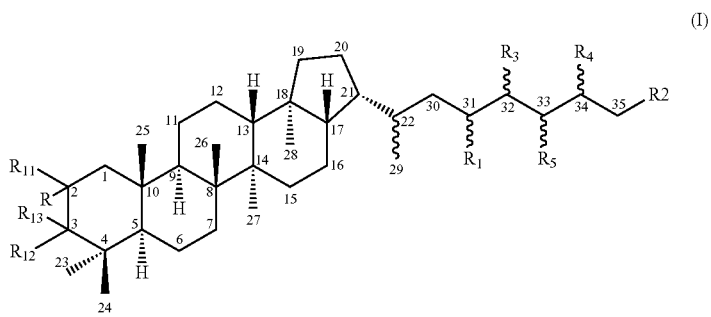

(I)

wherein

C22, C31, C33 and C34 have independently R or S chirality;

R, $R_{11}$, $R_{12}$ and $R_{13}$ are independently selected from H, D, methyl, or ethyl groups;

$R_1$, $R_3$, $R_4$, and $R_5$ are selected from H, D, methyl, hydroxymethyl, aminomethyl, hydroxyl, or amino groups, wherein at least three of the $R_1$, $R_3$, $R_4$, and $R_5$ groups each contains hydroxymethyl, aminomethyl, hydroxyl, or amino groups;

$R_2$ is selected from OH, $NH_2$, hydroxymethyl, aminomethyl, formula (II)

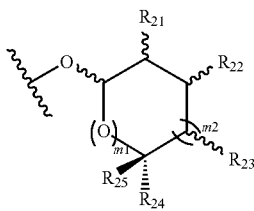

Formula (II)

in which n a wavy line on the ring carbon indicates a R or S chirality of the ring carbon, $m_1$ and $m_2$ are independently 0 or 1;

$R_{21}$, $R_{22}$, $R_{23}$, $R_{24}$ and $R_{25}$ are selected from OH, $NH_2$, hydroxymethyl, or aminomethyl groups wherein $R_{21}$, $R_{22}$, $R_{23}$, $R_{24}$ and $R_{25}$ contain at least one $NH_2$ or aminimethyl groups and one of $R_{24}$ and $R_{25}$ is hydroxymethyl, or aminomethyl groups.

12. The biofertilizer composition of claim 10, wherein the one or more $C_{35}$ hopanoids comprise at least one $C_{35}$ hopanoid selected from the group consisting of bacteriohopanetetrol (BHT) and aminobacteriohopanetriol, 2-methyl bacteriohopanetriol, aminobacteriohopanetriol, bacteriohopanetetrol, 2Me-aminobacteriohopanetriol, adenosylhopane, and 2Me-bacteriohopanetetrol.

13. A seed of a leguminous plant coated and/or inoculated with the biofertilizer of claim 1.

14. The coated seed of claim 13, wherein the leguminous plant is soybean (*Glycine max*).

15. A method of fertilizing a leguminous plant, the method comprises
    applying one or more biofertilizer of claim 1 to a leguminous plant or soil surrounding a leguminous plant for a time and under conditions to allow symbiosis of the nitrogen-fixing rhizobia with the leguminous plant,
    wherein the one or more biofertilizer is in a form suitable for administration to the leguminous plant, and/or for administration to a soil surrounding the leguminous plant.

16. The method of claim 15, wherein applying the one or more biofertilizer is performed in combination with one or more $C_{35}$ hopanoids, and wherein the applying is performed for a time and under conditions allowing interaction of the one or more $C_{35}$ hopanoids with the nitrogen-fixing rhizobia in the administered biofertilizer and/or biofertilizer compositions.

17. A method of fertilizing a leguminous plant, the method comprising
    coating and/or inoculating one or more seeds of the leguminous plant with one or more biofertilizer of claim 1, in a form suitable for administration to the one or more seeds of the leguminous plant.

18. The method of claim 17, the method further comprising
    coating and/or inoculating one or more $C_{35}$ hopanoids before the coating and/or inoculating the one or more seeds of the leguminous plant with the one or more biofertilizer.

19. A system to fertilize leguminous plants, the system comprising one or more biofertilizer essentially consisting of one or more nitrogen-fixing rhizobia naturally incapable of producing $C_{35}$ hopanoids and genetically engineered to include a set of genes of a nitrogen-fixing rhizobia naturally capable of producing $C_{35}$ hopanoids, enabling production of $C_{35}$ hopanoids by the one or more nitrogen fixing rhizobia naturally incapable of producing $C_{35}$ hopanoids, and/or biofertilizer compositions comprising said one or more biofertilizer and one or more $C_{35}$ hopanoids for simultaneous, sequential or combined use in fertilizing a leguminous plant
    wherein the set of genes comprises shc gene encoding a squalene-hopene cyclase, hpnH gene encoding a B12 binding radical SAM, and gene hpnG encoding for a nucleosidase.

20. A system to fertilize a leguminous plant, the system comprising one or more leguminous seed coated with one or more biofertilizer essentially consisting of one or more nitrogen-fixing rhizobia naturally incapable of producing $C_{35}$ hopanoids and genetically engineered to include a set of genes of a nitrogen-fixing rhizobia naturally capable of producing $C_{35}$ hopanoids, enabling production of $C_{35}$ hopanoids by the one or more nitrogen-fixing rhizobia and/or biofertilizer composition comprising said one or more biofertilizer and one or more $C_{35}$ hopanoids for simultaneous, sequential or combined use in fertilizing a leguminous plant
    wherein the set of genes comprises squalene-hopene cyclase shc gene, B12 binding radical SAM hpnH gene, and nucleosidase hpnG gene.

21. The system of claim 19, wherein the one or more nitrogen-fixing rhizobia comprise at least one selected from the group consisting of *Rhizobium etli*, *Rhizobium lequminosarum*, *Mesorhizobium loti*, *Sinorhizobium meliloti*, *Azorhizobium caulinodans*, and *Ochrobactrum anthropi*.

22. The biofertilizer of claim 10, wherein the acceptable vehicle is a carrier allowing increased stability, viability and/or effectiveness of the gas exchange of the one or more nitrogen-fixing rhizobia.

23. The biofertilizer composition of claim 10, further comprising one or more bacteria selected from the group consisting of *Bradyrhizobium* BTAi1, *Bradyrhizobium japonicum*, *Bradyrhizobium diazoefficiens*, *Bradyrhizobium* ORS278, and *Methylobacterium nodulans*.

24. The biofertilizer composition of claim 10, wherein the one or more nitrogen-fixing bacteria comprise *Rhizobium etli*, *Rhizobium leguminosarum*, *Mesorhizobium loti*, *Sinorhizobium meliloti*, *Azorhizobium caulinodans*, and *Ochrobactrum anthropi*.

25. The biofertilizer composition of claim 10, wherein the vehicle is a carrier selected from the group consisting of peat, vermiculite, lignite powder, clay, talc, rice bran, seed, rock phosphate pellet, charcoal, soil, paddy straw compost, wheat bran, gum Arabic, methylethylcellulose, sucrose solutions, vegetable oils and a mixture thereof.

26. The biofertilizer composition of claim 10, wherein the $C_{35}$ hopanoids are covalently linked to lipid A to form HoLA.

* * * * *

SEQUENCE LISTING

<160> NUMBER OF SEQ ID NOS: 32

<210> SEQ ID NO 1
<211> LENGTH: 34
<212> TYPE: DNA
<213> ORGANISM: Artificial Sequence
<220> FEATURE:
<223> OTHER INFORMATION: Synthetic polynucleotide

<400> SEQUENCE: 1
tatctagaaa gcttgcagtt tcccttcgtc gata                                34

<210> SEQ ID NO 2
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 2
accatgatac cgtagataga atacacgggg catctggctc gattactccg atagttaatt    60

<210> SEQ ID NO 3
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 3
aattaactat cggagtaatc gagccagatg ccccgtgtat tctatctacg gtatcatggt    60

<210> SEQ ID NO 4
<211> LENGTH: 34
<212> TYPE: DNA
<213> ORGANISM: Artificial Sequence
<220> FEATURE:
<223> OTHER INFORMATION: Synthetic polynucleotide

<400> SEQUENCE: 4
tatctagact gcagagcagg tccagaagaa gctc                                34

<210> SEQ ID NO 5
<211> LENGTH: 36
<212> TYPE: DNA
<213> ORGANISM: Artificial Sequence
<220> FEATURE:
<223> OTHER INFORMATION: Synthetic polynucleotide

<400> SEQUENCE: 5
tatatatagc ggccgcgcag tttcccttcg tcgata                              36

<210> SEQ ID NO 6
<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 6
tatatatatc tagacatctg gctcgattac tccgatagtt aatt                     44

<210> SEQ ID NO 7
<211> LENGTH: 43
<212> TYPE: DNA
<213> ORGANISM: Artificial Sequence
<220> FEATURE:
<223> OTHER INFORMATION: Synthetic polynucleotide

<400> SEQUENCE: 7
tatatatatc tagacccccgt gtattctatc tacggtatca tgg        43

<210> SEQ ID NO 8
<211> LENGTH: 34
<212> TYPE: DNA
<213> ORGANISM: Artificial Sequence
<220> FEATURE:
<223> OTHER INFORMATION: Synthetic polynucleotide

<400> SEQUENCE: 8
tatatatact gcagagcagg tccagaagaa gctc        34

<210> SEQ ID NO 9
<211> LENGTH: 48
<212> TYPE: DNA
<213> ORGANISM: Artificial Sequence
<220> FEATURE:
<223> OTHER INFORMATION: Synthetic polynucleotide

<400> SEQUENCE: 9
ttcgagctcg gtacccgggg atcctctaga gtggaaccgt cggacagc        48

<210> SEQ ID NO 10
<211> LENGTH: 50
<212> TYPE: DNA
<213> ORGANISM: Artificial Sequence
<220> FEATURE:
<223> OTHER INFORMATION: Synthetic polynucleotide

<400> SEQUENCE: 10
ttgtcagatc gagacgctca ctggtttaca atcgtttgga caggaagagc        50

<210> SEQ ID NO 11
<211> LENGTH: 50
<212> TYPE: DNA
<213> ORGANISM: Artificial Sequence
<220> FEATURE:
<223> OTHER INFORMATION: Synthetic polynucleotide

<400> SEQUENCE: 11
gctcttcctg tccaaacgat tgtaaaccag tgagcgtctc gatctgacaa        50

<210> SEQ ID NO 12
<211> LENGTH: 50
<212> TYPE: DNA
<213> ORGANISM: Artificial Sequence
<220> FEATURE:
<223> OTHER INFORMATION: Synthetic polynucleotide

<400> SEQUENCE: 12
acggccagtg ccaagcttgc atgcctgcag gctgatccac aaggagatcg        50

<210> SEQ ID NO 13
<211> LENGTH: 34
<212> TYPE: DNA
<213> ORGANISM: Artificial Sequence
<220> FEATURE:
<223> OTHER INFORMATION: Synthetic polynucleotide

<400> SEQUENCE: 13
tatatatagc ggccgcgtgg aaccgtcgga cagc        34

```
<210> SEQ ID NO 14
<211> LENGTH: 44
<212> TYPE: DNA
<213> ORGANISM: Artificial Sequence
<220> FEATURE:
<223> OTHER INFORMATION: Synthetic polynucleotide

<400> SEQUENCE: 14
tatatatatc tagactggtt tacaatcgtt tggacaggaa gagc                44

<210> SEQ ID NO 15
<211> LENGTH: 34
<212> TYPE: DNA
<213> ORGANISM: Artificial Sequence
<220> FEATURE:
<223> OTHER INFORMATION: Synthetic polynucleotide

<400> SEQUENCE: 15
tatatatatc tagatgagcg tctcgatctg acaa                          34

<210> SEQ ID NO 16
<211> LENGTH: 34
<212> TYPE: DNA
<213> ORGANISM: Artificial Sequence
<220> FEATURE:
<223> OTHER INFORMATION: Synthetic polynucleotide

<400> SEQUENCE: 16
tatatatact gcaggctgat ccacaaggag atcg                          34

<210> SEQ ID NO 17
<211> LENGTH: 32
<212> TYPE: DNA
<213> ORGANISM: Artificial Sequence
<220> FEATURE:
<223> OTHER INFORMATION: Synthetic polynucleotide

<400> SEQUENCE: 17
tatctagact gcagaacacc atcgggctga ag                            32

<210> SEQ ID NO 18
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 18
ggaagcctcg cgcagccgga tcgaatagtt catagcgtaa tgctgtcgcc ggaatttctc    60

<210> SEQ ID NO 19
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 19
gagaaattcc ggcgacagca ttacgctatg aactattcga tccggctgcg cgaggcttcc    60

<210> SEQ ID NO 20
<211> LENGTH: 34
<212> TYPE: DNA
<213> ORGANISM: Artificial Sequence
<220> FEATURE:
<223> OTHER INFORMATION: Synthetic polynucleotide
```

<400> SEQUENCE: 20
tatctagagg atccttttcg agcatgcctt atcc                               34

<210> SEQ ID NO 21
<211> LENGTH: 34
<212> TYPE: DNA
<213> ORGANISM: Artificial Sequence
<220> FEATURE:
<223> OTHER INFORMATION: Synthetic polynucleotide

<400> SEQUENCE: 21
tatctagaaa gcttaacttt gaagcggatt ggtg                               34

<210> SEQ ID NO 22
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 22
tttttgttcg tggtgctgtt tctcgcctta cattacacgt ttctttctgg gcttgaaatt   60

<210> SEQ ID NO 23
<211> LENGTH: 60
<212> TYPE: DNA
<213> ORGANISM: Artificial Sequence
<220> FEATURE:
<223> OTHER INFORMATION: Synthetic polynucleotide

<400> SEQUENCE: 23
aatttcaagc ccagaaagaa acgtgtaatg taaggcgaga acagcacca cgaacaaaaa   60

<210> SEQ ID NO 24
<211> LENGTH: 34
<212> TYPE: DNA
<213> ORGANISM: Artificial Sequence
<220> FEATURE:
<223> OTHER INFORMATION: Synthetic polynucleotide

<400> SEQUENCE: 24
tatctagact gcagcctgat tgcaacacag aacg                               34

<210> SEQ ID NO 25
<211> LENGTH: 879
<212> TYPE: DNA
<213> ORGANISM: Rhodopseudomonas palustris

<400> SEQUENCE: 25
atgacgtctg cgagcgagct tcgatcgggc aagacccacc gggacgagaa tttcccggtc    60
gcgtcgtgga tcatccatcc gcggcatcgc gacctgattc tggcgttcta caatttcgtc   120
cggaccgcgg acgacatcgc cgatcacgag atgctcgatg cgacaccaa gctcgaatat    180 ctcgatctgc tcgaagccga gctgctcggc gcggcgaga cccagcccga ggcggtgcat    240
ctgcgtcggg cgctggccga acgcggcatg ccgccgcgcc atgcgctcga tctgctgacc    300
gcgtttcgga tggacgtcac caagctgcgc tacgaggatt gggacgaggt cattcactac    360
tgccgctact cggcgatgcc ggttggccgc ttcatgctcg acgtccacgg cgaaagcacc    420
acgacctggc aggcctccga cgcgctgtgc gcggggcttc agatcaacaa tcacctgcag    480
gactgcggca aggactatcg caccctcaat cgcgtgtatc tgccacgcga cgtgctcgat    540
gccgccggcg ccaaggtcga agacctcggc ctgcagaagt cgtcaccggc gctgctgaaa    600

| | |
|---|---|
| tgcctgcagg gtcttgcggt ccgcaccgcg tcgctgctcg gcgacggccg gccgctcgcc | 660 |
| gccgagatca aggattatcg cctcggtctc gaagtctcgg tgatccaggc ctatgccgat | 720 |
| cgcatcgtgc ggatgctgca gacccgcgat ccgctcagcg agcgcgtgca tctgaagccg | 780 |
| atcgaattcg tgatcgccag cttcggcgcg atgagttcgg agatcgtccg tcgtagcttc | 840 |
| ggaaagggc cggtgtcgca tccggcgccg cgcgcatga | 879 |

<210> SEQ ID NO 26
<211> LENGTH: 840
<212> TYPE: DNA
<213> ORGANISM: Rhodopseudomonas palustris

<400> SEQUENCE: 26

| | |
|---|---|
| atgaccgttc acgccacgcc agagccggcc gcacatcaag gtgtcgcgct cggcagttcg | 60 |
| ttctacgccg cgatgcgcat cctgccgcgt ccgcagcgcg aggcgatgtt ccaggtctac | 120 |
| agcttctgcc gcttcgtcga cgacatcgcc gattccgatc ggccgcgcga gcagcgggtc | 180 |
| gccgagctgc agcaatggcg cgacgacatc gccgcgctgt atcgcggtgc gccgccgccg | 240 |
| cggctcgccg actatcagga gtcgctgcgc actttcgggc tgaagcgcga ggacttcgag | 300 |
| gcgatcatcg acggcatgga gatggatgtc gacgccgaca tccgcgcgcc cgatgaggcc | 360 |
| acgctcgatc tgtactgcga ccgcgtcgcc agcgcggtgg gacggctgtc ggtgcggatc | 420 |
| ttcggccttc cggaagccga cggcatcgag ctgtcgcatc atctcggacg cgcgctgcag | 480 |
| ctcaccaaca tcctgcgcga catcgacgag gacaccggca tcggccggct gtatctgccg | 540 |
| agcgagctgc tgcacaaggt cggtatcacc gcaaccgatc cgcgcgtggt cgcggcggat | 600 |
| tctgcgctgc cgagcgtctg cgcgccgctg gtcgagcgtg cgctcgcgca ttttgccgcc | 660 |
| gccgacaagg tgatgaaccg taatccgcgc cgggtggtga agctccccg tatcatgggc | 720 |
| aagtactact actcgatctt gcagcttttg atcgcgcgcg gtttcgcagc cgcgcgcgcc | 780 |
| ccggtgaagc tcggcaaggc ttcgaagatc gccatcctgc tgcaatacgc gatcgtgtga | 840 |

<210> SEQ ID NO 27
<211> LENGTH: 1257
<212> TYPE: DNA
<213> ORGANISM: Rhodopseudomonas palustris

<400> SEQUENCE: 27

| | |
|---|---|
| atgtcgaaaa cagttcacgt cattggtgcg ggaatctccg gcttgcggc gcgatccgg | 60 |
| ctcgcccgcg ccggcctcac cgtccatgtt cacgaagcga tgcagcaggc cggtggccgc | 120 |
| tgccgctcgt atttcgacgc ccagaccggg cttgtcatcg acaacggcaa tcacctgctg | 180 |
| ctgtcgggta atcacgccgc ctgcgactac gcgcggacga tcggcaccga ggcgggcctc | 240 |
| gtcggcccgg agcgcgccga gttcgacttc atcgatctgc cggctaatgc gcgctggcgg | 300 |
| ctgaagctcg gcggcggcaa gctgccgctg tggctgtttg atgccaatag ccgcgtgccg | 360 |
| gacacgtcga tcggcgatta cctcggcttg atgccgctgc tgtgggcgcc gaccaccaaa | 420 |
| ctgatcggcg acaccatcaa ctgctccggc ccgctgtacg accgcttggt ggcgccgctg | 480 |
| ctgctcgccg cgctcaacgt cgatccgccg gaaggctcgg ccgggcttgc cggcgcggtg | 540 |
| gttcgtgaga cgctgctggc cggcggcaag gcctgccggc cgctgatcgc ccgcgatggc | 600 |
| ctgtcggcgt gctggtcga gcggccgtg gcgcagctcg ccgccgcgg tccaggagtg | 660 |
| cagttcggcc acgagctgcg ggcgctgacc ccggccggcg accgcgtcgg cgcgctgcag | 720 |
| ttcggcggtg aggatgtcgt caccctcggg ccggatgatg cggtggtgct ggcggtgccg | 780 |

| | |
|---|---|
| ccgcgcccgg ccgcttcgct gctgcccggg ctgaagacgc cacaggaata ccgcgcgatc | 840 |
| gtgaacgcgc acttcaatta cgcgccgccg cctggcatgc cggccctgac cggggtgatc | 900 |
| ggcggggtgg tggagtggct gttcgcgttc ccgaaccggc tgtccgtgac gatcagcaac | 960 |
| ggcgaccggc tggtggacgc cccgcgcgag cagcttgcgg ccgaaatttg gggcgaaatc | 1020 |
| tgtaaaattg cggggatctc ggccaatctg ccgccgtggc aaattgtccg cgagcgccgc | 1080 |
| gccacgttcg ccgctacacc ggcgcagaac gccctgcgcc cgggccggt cacccagtgg | 1140 |
| agaaacctat atctcgcagg cgattggact gatacggggt taccggcgac catcgaggga | 1200 |
| tcggtccggt ccggcaaccg tgccgcggac ctggtgctgg ccgctggccg cgcctga | 1257 |

<210> SEQ ID NO 28
<211> LENGTH: 1962
<212> TYPE: DNA
<213> ORGANISM: Rhodopseudomonas palustris

<400> SEQUENCE: 28

| | |
|---|---|
| atggattccg gcagctacac gactggtgtg gagcgcaacg cgctcgaagc ttcgatcgat | 60 |
| gcggcgcgca gcgcgctgct gaattatcgt cgcgacgatg ccattgggt gttcgaactc | 120 |
| gaggccgatt gcaccattcc tgccgaatac gtgctgctgc ggcattacct cggcgagccg | 180 |
| gtcgatgccg agctcgaagc caagatcgcg gtttatctgc cgcatcca gggtgcccat | 240 |
| ggcggctggc cgctggtgca cgacggcgac ttcgacatga cgccagcgt gaagggttac | 300 |
| ttcgcgctga agatgatcgg cgacagcatc gatgccccgc atatggtgcg ggcgcgcgag | 360 |
| gcgatccgtt cgcgcggcgg cgcgatccac tccaacgtct tcacccggtt tctgctcacg | 420 |
| ttgtacggcg ttacgacctg gcgcgcggtt ccggtactgc cggtcgagat catgctgctg | 480 |
| ccgagctggt cgccgttcac actgaccaag atctcgtatt gggcgcgtac cacgatggtg | 540 |
| ccgctgctcg tgctgtgcgc gctgaagccg caggccaaga tccgaaggg cgtcggcatc | 600 |
| gacgaactat tccttcagga cccgaagacg atcgggatgc cggtcaaggc gccgcatcag | 660 |
| aactgggcgc tgttcaagct gttcggatcg atcgacgcgg tgctgcgcgt gatcgagcct | 720 |
| gtgatgccca aaggcatccg caagcgcgcg atcgacaagg cgctcgcctt catcgaggag | 780 |
| cggctcaacg gcgaggacgg catgggcgcg atcttcccgc cgatggccaa cgccgtgatg | 840 |
| atgtacgagg cgctcggcta tcccgaggac tatccgccgc gccagcca gcgccgcggc | 900 |
| attgatctct tgctggtcga tcgcggcgac gaagcctact gccagccctg cgtgtcgccg | 960 |
| gtgtgggaca ccgcgctcgc cagccatgcg gtgctcgagg cggacggtca cgagggcgcc | 1020 |
| aagtcggtgc ggccggcgct cgactggctg ctcccgcgcc aggtgctcga cgtcaagggc | 1080 |
| gactgggccg tcaaggcccc gaacgtccgc ccggcggct gggcgttcca gtacaacaac | 1140 |
| gcccactatc cggatctcga cgataccgcg gtggtggtga tggcgctcga ccgcgcccgc | 1200 |
| aaggaccagc cgaatcccgc ctacgatgcc gcgattgccc cgcccgcga gtggatcgag | 1260 |
| gggatgcaga gcgacgatgg cggctggggt gccttcgaca tcaacaacac tgagtattat | 1320 |
| ttgaacaaca tcccgttctc ggaccatggc gcgatgctcg atccgccgac cgaggacgtc | 1380 |
| accgcgcgct gcgtctcgat gctggctcag ctcggtgaga ccatggacag cagcccggcg | 1440 |
| ctggcccgcg ccgtcggcta tctgcgcgac acccagctcg ccgagggctc ctggtacggc | 1500 |
| cgctggggca tgaattacat ctacggcacc tggtcggtgc tgtgcgccct caacgccgcc | 1560 |
| ggcgttcccc atgccgatcc gatgatccgc aaggcggtcg cctggctgga gtcggtgcag | 1620 |
| aatcgcgacg gcggctgggg cgaggacgcg gtcagctacc gactggatta ccgcggctac | 1680 |

```
gaaagtgcac cttcgaccgc ctctcagacg gcatgggctt tgcttgctct gatggctgcg    1740
ggtgaggtcg atcatcccgc cgtggcacgg ggcatcgagt acctgaaaag cacacagacc    1800
gaaaaaggac tgtgggacga gcagcgttac acggcgacgg gcttcccgcg ggtgtttat     1860 ctgcggtatc atggctattc gaagttcttc ccactctggg cgctcgcccg gtatcggaac    1920
ttgcaggcca cgaacagcaa ggtggtaggg gtcggaatgt ga                       1962

<210> SEQ ID NO 29
<211> LENGTH: 744
<212> TYPE: DNA
<213> ORGANISM: Rhodopseudomonas palustris

<400> SEQUENCE: 29
gtgattctgg gggcagtgga cgaccaggcc gcggcgcttc gccaagatcc gcggccggta      60
ctgattgtga cgggcctgat tcaggaagca cgtatcgcgg cggggccggg cctcaccgtt     120
atctgcagca gcagtgaccc caagcaattg cgcgcgatca tggccgactt cgacgcatcg     180
tcgatccggg gcgtgatcag cttcggcgtc gccgggggc tggatccctc tctcgaggca      240
ggtgacatcg tcatcgccac cgaggttgtg gcgggtgaac gccgctggac gtcggaagtt     300
gcactgaccg acgaattatt gcgaagcgcc gggctcggcc gtcagcgcgt cgtgcgcggc     360
ggtctggtcg gcgccgagca ggtgatcgca gcgcgctccg ccaaggcggc gctgcgctcg     420
gagaccggtg cggctgcggt cgatatggaa agccacatcg ccgccgattt cgccgccgcc     480
gccaagctgc cgttcgcggc gctccgggtg atcagcgatc cggcgaatcg cagcctgccg     540
cagatcgtgt cgagcgcgat caagccgaac ggcgatatcg acctgcgcaa ggtgctgcgc     600
ggcatcgccc gtcacccgac ctcgatccgc tcgctggtgt cgaccggcat cgacttcaac     660
cgcgcgctgc gctccctgcg cggctgtcgg aactttgtgc aggacgccgt gctcggccgc     720
ggcggtctcg tcgccgagat ctga                                            744

<210> SEQ ID NO 30
<211> LENGTH: 1161
<212> TYPE: DNA
<213> ORGANISM: Rhodopseudomonas palustris

<400> SEQUENCE: 30
atggctattc cgtttcacaa ggaactggtg atcggcggtt atctgctgaa gcagaagctg      60
ctcgggcgga agcgttatcc gctggtactg atgctggagc cgctgttccg ctgtaacctc     120
gcctgcgccg gctgcggcaa gatcgactat cccgacgcga tcctgaaccg ccggatgacc     180
gcacaagagt gctgggacgc cgccgaggaa tgcggcgcgc cgatggttgc gatcccgggc     240
ggcgaaccgc tgatccacaa ggagatcggc gagatcgtgc gcggcctggt ggcgcgcaag     300
aagttcgtgt cgctgtgcac caacgcgctg ctgctcgaga agaagctgca tctgttcgag     360
ccgtcgccct acctgttctt ctcggtgcat ctcgacggcc tgaaggagca ccacgacaag     420
gcggtgtcgc agcagggcgt gttcgaccgc gcagtcgcgg cgatcaaggc cgccaaggcc     480
aagggcttca ccgtcaacgt caactgcacg gtgttcgacg gctacgccgc cgaagacatc     540
gccaagttca tggacttcac cgaggaactc ggcgtcggcg tctcgatctc gccgggctac     600
gcctatgagc gcgctccgga ccaggagcac ttcctcaacc gcaccaagac caagaacctg     660
ttccgcgagg tgttcgcgcg cggcaagggc aagaagtgga gcttcatgca ctccagcatg     720
ttcctcgact tcctggccgg caatcaggag ttcgagtgca cgccgtgggg tatgccggcg     780
cgcaacattt tcggctggca gaagccctgc tacctgctcg gcgaaggcta cgccaagact     840
```

```
ttccaggagc tgatggaaac caccgattgg gattcctacg gcaccggcaa gtacgagaag      900
tgcgccgact gcatggcgca ttgcggctac gaaccgaccg cggcgatggc ctctctcaac      960
aatccgctga aggccgcctg ggtggcgctc cgcggcatca agacctcggg cccgatggcg     1020
ccggagatcg acatgtcgaa gcagcgcccg gcgcagtact tgttctccga gcaggtccag     1080
aagacgctga cgcagatccg ccaggacgag gccgccgagg ccaaggacaa gcggcaggcg     1140
gaaaggtcga cggcggcctg a                                               1161

<210> SEQ ID NO 31
<211> LENGTH: 2607
<212> TYPE: DNA
<213> ORGANISM: Rhodopseudomonas palustris

<400> SEQUENCE: 31
gtgctgaaaa gtgccatcgt ctccattgtc agagccagca cccgttttgc ggcttttact       60
gtgctgatcg gcgtatttct cgcagttgca gcaggtttct atacttacca acatttcggg      120
atcaacacag acatcaatca tttgatctcg tctgatctcg actggcgcaa acgtgatatc      180
gcgttcgaga aggcattcga ccaggaacgg ctgatcctgg ccgtcgtcga ggccccgacg      240
ccggaattcg ccaatgccgc ggcggccaag ctcacgcccg aattgtccaa gaataacatc      300
aacttcgact cggtgaagcg gctcggcggc gggccgtttt tcgaccgcag cgggctgctg      360
ttcctgccca aggacgaggt cgccaaggcc accggcagt tccagcaggc ggttcccctg      420
atcgagatca tggccggcga tccgtcgatc cgcggcctga cggcggcact cgagaccggt      480
ctggtcgggt tgaaacgcgg ggaactgacc ctcgacgcca ccgcgaaacc tttcaataca      540
gtcgccgcga ccgtcgagga cgtgctcggc aagcagcagg cgttcttctc ctggcgcggc      600
ctggtcaatc cggaaccgct gaccgatggc gacaagcgcg ccttcatcga ggtcaagccg      660
atcctcgact tcaaggcgct cgaacccggc aaggcggcga ccgacgcgat ccgtcaggcg      720
gcagtcgatc tcaagatcga gcaggatttc ggcgcccggg tgcggctgac cggcccggtg      780
ccgatcgcca acgaggaatt cgctaccgtt aaggacggcg ccgtggtcaa cggcatcggg      840
accgtcgtgg tggtgctgct gatcctctgg atggcgctgc attcctccaa gatcatcttc      900
gcggtggcgg ccaatctggt gatcggcctg tcgatcacca ccgcggtcgg cctgatgctg      960
gtggattcgc tcaacctgct gtcgatcgcg ttcgcggtgc tgttcgtcgg cctcggcgtc     1020
gatttcggca tccaattcag cgtccgctat cgatcggaac gccacaagac cggggacctc     1080
gagaaggccc tggtccaggc cgccgaatac tccgcggtgc cgctgtcact ggcggcgatg     1140
tcgaccacgg ccggcttcct gtcgttcctg ccgacgtcct acaaaggcat ttccgaactc     1200
ggcgagatcg ccggtgccgg catggcgatc gcgttcttca ccagcatcac cgtgctgccg     1260
gcgctgctga agctgctgaa cccggcgggt gagaaggaac gcttggcta cgccttcctg     1320 gcgccggtcg atcacttcct ggagaagcac cgcatcgcca tcatcgtcgg cacgatcggt     1380
gtcgcgctgg ccgcctgcc actgctgtac ttcatgcatt cgacttcaa cccgatcaat     1440 ctgcgcagcc cgaaggtcga gtcgatcgcg acgttccttg acctgcgcaa ggatccgaat     1500
accggtgcca acgccgtcaa cgtgatggcg ccgaacgagc aggcggctcg tgagatcgaa     1560
gccaagctcg ccaagctgcc gcaggtatcg cgcaccatct cgctcgacac tttcgtgccg     1620
ccggaccagc cggagaagct gaagctgatc caggccggcg ccaaggtgct ggagcccgcg     1680
ctcaatcccg agcagatcga tccgccgccg tccgatcagg acaatatcgc gtcgctgaag     1740
agctcggccg aagcgctgcg ccgcgccgcc ggcgaggcca ctggacccgg cgccgacgcc     1800
```

| | |
|---|---|
| tcgcgccggc tcgctaccgc gctgaccaag cttgcgggcg ccgatcaggc gatgcgcgag | 1860 |
| aaggcccagg acgtgttcgt gcggccgctg ctgctcgact tcgaactgct gcgcaacatg | 1920 |
| ctgaaagcgc agccggtgac gctcgacaac ctgccggccg acatcgtgtc gtcgtggaag | 1980 |
| accaaggacg tcagatccg cgtcgaggtg ctgccgagcg gcgaccccaa cgacaacgat | 2040 |
| acgctgcgca agttcgccgc cgccgtgctg caggccgagc cgttggcgac cggcggtccg | 2100 |
| gtgtcgatcc tgaagtcggg cgataccatc gtggcctcgt tcatccaggc cgggctgtgg | 2160 |
| gcgttattgt cgatctcgat cctgctgtgg atcacgctgc gccggatttc cgacgtggcg | 2220 |
| ctgaccctgg tgccgctgct ggtggccggt gcggtgacgc tggagatctg cgtgctgatc | 2280 |
| gatctgccgc tgaacttcgc caacatcgtc gccttgccgc tgctgctcgg cgtcggcgtc | 2340 |
| gcgttcaaga tctattacgt gaccgcctgg cgctccggcc gcaccaacct gctgcagtcg | 2400 |
| gcgctgaccc gggcgatttt cttcagcgcc ctgaccaccg ccaccgcatt cggcagcctg | 2460 |
| tggctgtcga gccatccggg aacgccagc atgggcaagc tgctggcgct gtcgttgctc | 2520 |
| accacgctcg gtgccgtgct gctgttccag ccggccctga tgggcaagcc gcgccacatc | 2580 |
| gacgagtccg gcgacaccga tctgtga | 2607 |

<210> SEQ ID NO 32
<211> LENGTH: 1392
<212> TYPE: DNA
<213> ORGANISM: Rhodopseudomonas palustris

<400> SEQUENCE: 32

| | |
|---|---|
| atgtatcagc cgaatttaga ccttgccgag atgtttgcgg cgcgcgaagc gaaccgcagt | 60 |
| tcgatgcacg cccggcatct caacgagcag ctcgtccgcg tcctcaaaac catcggctac | 120 |
| gacgtcggct tccagaaggg caccggtcag tacctctacg accgcgacgg cgcccgctat | 180 |
| ctcgacctgc tcagcggctt tggcgtcttc gcgctcggcc gcaaccatcc ggtggtgcgc | 240 |
| aaggcgttgc agagcgtgct cgatgccgac ctgcccaatc tggtgcagct cgacgtctcg | 300 |
| acgctcgccg gtatcctggc tgagcggctg ctcgagcagg tgccgtatct cgacaaggtg | 360 |
| ttcttcgcca attccggcgc cgagagcgtc gaggccgcga tcaagttcgc gcgcggtgca | 420 |
| acgggacgca acggtatcgt caattgcgac cacagctacc atggcctgac ctacggcgcg | 480 |
| ctgtcgctga ccgacgacca gaatttccag ggtggctttg gccgctgct gccgggtgtc | 540 |
| accaccatcc cgttcaacga tctcgaagcg ctggagaagg tgctgtcgac ccgcgaggtc | 600 |
| gccgccttca tcgtcgagcc gatccagggc aagggcgtca acatgcccac cgacgagttc | 660 |
| ctgccggggcg ccgccgcgct gtgcaaacgc tacggcacgt tgttcgtcgc cgacgaaatc | 720 |
| cagaccggca tgggccgcac cggccgcttc ctcgcgggtcg agcactggaa tgtcgaaccc | 780 |
| gacatggtgc tgctgtcgaa ggcgctgtcg ggcggccacg taccggtcgg cgcggtgctg | 840 |
| acccgcaagt cgatcttcga caagatcttc aaccgcatgg atcgcgccgt ggtgcacggc | 900 |
| tcgaccttcg ccaagaacga tctggcgatg gctgccggca ttgcgacgct ggaagtcctc | 960 |
| aaagccgaga agctggtcga ggccgccgcc aagcgcggcg ccgaattgcg gctggcgctc | 1020 |
| acgcgcatgt tccccggcta cgaactgctc aaggaagtgc gcggcaaggg gctgatgatc | 1080 |
| ggcgtcgaat tcggcccgcc gcaatcgctg cggctgaagg cgtcgtggac gatgctggag | 1140 |
| accgccaaca agggcctgtt cgtccagctg atcaccgtgc cgctgttcaa ggatcacaag | 1200 |
| atcctgacgc aggtcgcggg ccatgggctg cacaccatca gctgctgcc gccgctgacc | 1260 |
| atcaccgaag acgactgcgc ctggatcgaa cgcgccttcg acgacaccat cgctgccagc | 1320 |

```
cacaaggtgc cgggcgcgat ctggtcgctc ggcaagaccc tggtcgacaa cgcggtgcgt    1380
aagtcggcgt aa                                                        1392
```